US012161843B2

United States Patent
Appy et al.

(10) Patent No.: US 12,161,843 B2
(45) Date of Patent: Dec. 10, 2024

(54) AUTOMATIC DRUG DELIVERY DEVICE

(71) Applicant: Novartis AG, Basel (CH)

(72) Inventors: Jacques Appy, Schlierbach (FR); Andrew Bryant, Buggingen (DE); Neil Cammish, Manchester (GB); Congyi Huang, Klagenfurt (AT); John Palmer-Felgate, Horsham (GB); Claudio Rossi, Elinsbach (CH); Oliver Shergold, Bolligen (CH); Gianluca Tordi, Derendingen (CH); Adrian Francios Von Muralt, Basel (CH); Mark Horlock, Cheshire (GB)

(73) Assignee: Novartis AG, Basel (CH)

( * ) Notice: Subject to any disclaimer, the term of this patent is extended or adjusted under 35 U.S.C. 154(b) by 871 days.

(21) Appl. No.: 17/057,558

(22) PCT Filed: May 23, 2019

(86) PCT No.: PCT/IB2019/054298
§ 371 (c)(1),
(2) Date: Nov. 20, 2020

(87) PCT Pub. No.: WO2019/224782
PCT Pub. Date: Nov. 28, 2019

(65) Prior Publication Data
US 2021/0196894 A1  Jul. 1, 2021

(30) Foreign Application Priority Data

May 24, 2018 (EP) ..................................... 18174181
May 24, 2018 (EP) ..................................... 18174183
(Continued)

(51) Int. Cl.
*A61M 5/20* (2006.01)
*A61M 5/19* (2006.01)
(Continued)

(52) U.S. Cl.
CPC ............ *A61M 5/2033* (2013.01); *A61M 5/19* (2013.01); *A61M 5/20* (2013.01); *A61M 5/24* (2013.01);
(Continued)

(58) Field of Classification Search
CPC ........ A61M 5/2033; A61M 5/19; A61M 5/20; A61M 5/24; A61M 5/3157; A61M 5/3202;
(Continued)

(56) References Cited

U.S. PATENT DOCUMENTS 3,220,412 A   11/1965  McConnaughey et al.
5,681,291 A   10/1997  Galli
(Continued)

FOREIGN PATENT DOCUMENTS

AU   2010201665 B2   5/2013
AU   2018202115 B2   11/2019
(Continued)

*Primary Examiner* — Phillip A Gray
*Assistant Examiner* — Rachel T. Smith
(74) *Attorney, Agent, or Firm* — Frost Brown Todd LLP

(57) ABSTRACT

An automatic drug delivery device, for dispensing a fluid medicament, includes: a longitudinal housing; a removable cap; a syringe assembly having a hollow syringe body and an injection needle; and a drive mechanism. The loaded drive mechanism is operatively coupled with a safety shield movable within the longitudinal housing. The safety shield is biased into a proximal position in which it protrudes out of the proximal end of the longitudinal housing in order to cover a needle tip of the injection needle. The safety shield is movable into a distal position in which the injection needle is exposed for injection. The device includes a feedback mechanism providing a visual feedback to the user indicating an actual state of operation. The feedback mecha-
(Continued)

nism includes a visual indicator which appears in a transparent window on the distal end of the housing.

20 Claims, 46 Drawing Sheets

(30) Foreign Application Priority Data

May 24, 2018 (EP) ..................................... 18174190
May 24, 2018 (GB) ..................................... 1808598

(51) Int. Cl.
    *A61M 5/24*     (2006.01)
    *A61M 5/315*     (2006.01)
    *A61M 5/32*     (2006.01)

(52) U.S. Cl.
    CPC ........ *A61M 5/3157* (2013.01); *A61M 5/3202* (2013.01); *A61M 5/3204* (2013.01); *A61M 5/3234* (2013.01); *A61M 2005/2013* (2013.01); *A61M 2005/3267* (2013.01); *A61M 2205/581* (2013.01); *A61M 2205/582* (2013.01); *A61M 2205/583* (2013.01); *A61M 2207/00* (2013.01)

(58) Field of Classification Search
    CPC ............... A61M 5/3204; A61M 5/3234; A61M 2005/2013; A61M 2005/3267; A61M 2205/581; A61M 2205/582; A61M 2205/583; A61M 2207/00; A61M 2005/2407; A61M 2005/2414; A61M 2005/2492; A61M 2205/192; A61M 2005/3247; A61M 5/3243
    See application file for complete search history.

(56) References Cited

U.S. PATENT DOCUMENTS

| | | | |
|---|---|---|---|
| 5,988,452 | A | 11/1999 | Dent et al. |
| 7,141,286 | B1 | 11/2006 | Kessler et al. |
| 7,566,322 | B2 | 7/2009 | Brand et al. |
| 8,048,035 | B2 | 11/2011 | Mesa et al. |
| 8,398,594 | B2 | 3/2013 | Streit et al. |
| 8,641,668 | B2 | 2/2014 | Matusch |
| 8,979,807 | B2 | 3/2015 | Grunhut et al. |
| 8,992,477 | B2 | 3/2015 | Raday et al. |
| 9,125,996 | B2 | 9/2015 | Takemoto |
| 9,205,199 | B2 | 12/2015 | Kemp et al. |
| 9,227,017 | B2 | 1/2016 | Buchine et al. |
| 9,265,892 | B2 | 2/2016 | Segal |
| 9,327,084 | B2 | 5/2016 | Evans |
| 9,333,305 | B2 | 5/2016 | McLoughlin et al. |
| 9,522,231 | B2 | 12/2016 | Schneider et al. |
| 9,526,845 | B2 | 12/2016 | Roberts et al. |
| 9,579,459 | B2 | 2/2017 | Jennings et al. |
| 9,579,460 | B2 | 2/2017 | Marshall et al. |
| 9,604,011 | B2 | 3/2017 | Roberts et al. |
| 9,744,306 | B2 | 8/2017 | Cowe |
| 9,757,524 | B2 | 9/2017 | McLoughlin et al. |
| 9,789,253 | B2 | 10/2017 | Fabien et al. |
| 9,789,257 | B2 | 10/2017 | Travanty |
| 9,795,734 | B2 | 10/2017 | McLoughlin et al. |
| 9,821,115 | B2 | 11/2017 | Wozencroft |
| 9,861,751 | B2 | 1/2018 | Iio et al. |
| 9,974,904 | B2 | 5/2018 | Burk et al. |
| 9,999,734 | B2 | 6/2018 | Cowe |
| 10,010,680 | B2 | 7/2018 | Limaye et al. |
| 10,080,846 | B2 | 9/2018 | Sonderegger et al. |
| 10,105,499 | B2 | 10/2018 | Schwirtz et al. |
| 10,137,248 | B2 | 11/2018 | Holmqvist et al. |
| 10,183,121 | B2 | 1/2019 | Cowe |
| 10,188,799 | B2 | 1/2019 | Saussaye et al. |
| 10,207,052 | B2 | 2/2019 | Saussaye |
| 10,220,160 | B2 | 3/2019 | Ruan et al. |
| 10,232,117 | B2 | 3/2019 | Halseth |
| 10,232,124 | B2 | 3/2019 | Cowe |
| 10,238,804 | B2 | 3/2019 | Young et al. |
| 10,238,805 | B2 | 3/2019 | Carmel et al. |
| 10,265,471 | B2 | 4/2019 | Kapas et al. |
| 10,279,130 | B2 | 5/2019 | Mosebach et al. |
| 10,293,120 | B2 | 5/2019 | Cabiri et al. |
| 10,300,218 | B2 | 5/2019 | Stefanov et al. |
| 10,307,539 | B2 | 6/2019 | Alexandersson |
| 10,335,549 | B2 | 7/2019 | Edwards et al. |
| 10,350,362 | B2 | 7/2019 | Dennis, Jr. et al. |
| 10,350,371 | B2 | 7/2019 | Bates et al. |
| 10,363,377 | B2 | 7/2019 | Atterbury et al. |
| 10,384,009 | B2 | 8/2019 | Olson et al. |
| 10,384,015 | B2 | 8/2019 | Brereton et al. |
| 10,391,244 | B2 | 8/2019 | Schweikert et al. |
| 10,391,257 | B2 | 8/2019 | Piehl et al. |
| 10,398,842 | B2 | 9/2019 | Niven et al. |
| 10,406,280 | B2 | 9/2019 | Cronenberg |
| 10,420,898 | B2 | 9/2019 | Daniel |
| 10,420,899 | B2 | 9/2019 | Draper et al. |
| 10,485,933 | B2 | 11/2019 | Vogt et al. |
| 10,518,033 | B2 | 12/2019 | Takabatake et al. |
| 10,518,041 | B2 | 12/2019 | Brereton et al. |
| 10,543,322 | B2 | 1/2020 | Benito et al. |
| 10,583,260 | B2 | 3/2020 | Kemp |
| 2007/0265568 | A1 | 11/2007 | Tsals |
| 2009/0118677 | A1 | 5/2009 | Walton et al. |
| 2010/0286611 | A1 | 11/2010 | Schraga |
| 2011/0270161 | A1 | 11/2011 | Harrison et al. |
| 2013/0144218 | A1 | 6/2013 | Daniel |
| 2013/0281938 | A1 | 10/2013 | Ekman et al. |
| 2013/0310746 | A1 | 11/2013 | Wozencroft |
| 2013/0331796 | A1 | 12/2013 | Wozencroft |
| 2014/0025006 | A1* | 1/2014 | Takemoto ........... A61M 5/2033 604/110 |
| 2014/0025013 | A1 | 1/2014 | Dowds et al. |
| 2014/0135303 | A1 | 5/2014 | Wotton et al. |
| 2014/0343504 | A1 | 11/2014 | Bicknell et al. |
| 2016/0015897 | A1 | 1/2016 | Swanson et al. |
| 2016/0074584 | A1 | 3/2016 | Carmel et al. |
| 2016/0089503 | A1 | 3/2016 | Olson |
| 2016/0220764 | A1 | 8/2016 | Durvasula et al. |
| 2016/0317751 | A1 | 11/2016 | Andersen |
| 2016/0331900 | A1 | 11/2016 | Wei |
| 2016/0361496 | A1 | 12/2016 | Guillermo et al. |
| 2017/0065763 | A1 | 3/2017 | Rossitto et al. |
| 2017/0143893 | A1 | 5/2017 | Hasumi et al. |
| 2017/0239424 | A1 | 8/2017 | Wei |
| 2017/0246389 | A1 | 8/2017 | Stillman |
| 2017/0246400 | A1* | 8/2017 | Stefanov ........... A61M 5/31585 |
| 2017/0274150 | A1 | 9/2017 | Takabatake et al. |
| 2017/0354779 | A1 | 12/2017 | Atterbury et al. |
| 2018/0001025 | A1 | 1/2018 | Sarkinen et al. |
| 2018/0036492 | A1 | 2/2018 | Schader et al. |
| 2018/0117264 | A1 | 5/2018 | Hirobe |
| 2018/0161504 | A1 | 6/2018 | Kemp et al. |
| 2018/0169338 | A1 | 6/2018 | Mosebach et al. |
| 2018/0296768 | A1 | 10/2018 | Gould et al. |
| 2018/0339114 | A1 | 11/2018 | Wendland et al. |
| 2019/0001070 | A1 | 1/2019 | Wendland et al. |
| 2019/0009025 | A1 | 1/2019 | Chakrabarti et al. |
| 2019/0009037 | A1 | 1/2019 | Wendland et al. |
| 2019/0022317 | A1 | 1/2019 | Uddin et al. |
| 2019/0046735 | A1 | 2/2019 | Ingerslev et al. |
| 2019/0111214 | A1 | 4/2019 | Gillespie, III |
| 2019/0151561 | A1 | 5/2019 | Bernhard et al. |
| 2019/0151564 | A1 | 5/2019 | Schrul et al. |
| 2019/0151565 | A1 | 5/2019 | Groetzbach et al. |
| 2019/0184093 | A1 | 6/2019 | Sjolund et al. |
| 2019/0184101 | A1 | 6/2019 | Wendland et al. |
| 2019/0209786 | A1 | 7/2019 | Tschirren et al. |
| 2019/0224416 | A1 | 7/2019 | Dugand et al. |
| 2019/0250070 | A1 | 8/2019 | Fetzer et al. |
| 2019/0282767 | A1 | 9/2019 | Pedersen et al. |
| 2019/0298928 | A1 | 10/2019 | Shaw et al. |
| 2019/0328968 | A1 | 10/2019 | Giambattista |
| 2019/0336700 | A1 | 11/2019 | Nober et al. |

(56) References Cited

U.S. PATENT DOCUMENTS

| | | |
|---|---|---|
| 2019/0351139 A1 | 11/2019 | Sarkorov et al. |
| 2019/0374722 A1 | 12/2019 | Corrigan et al. |
| 2019/0381238 A1 | 12/2019 | Stonecipher et al. |
| 2020/0009314 A1 | 1/2020 | Helmer |
| 2020/0023144 A1 | 1/2020 | Burkett |
| 2020/0030540 A1 | 1/2020 | Watts et al. |
| 2020/0030547 A1 | 1/2020 | Wang et al. |
| 2020/0038598 A1 | 2/2020 | Chu et al. |
| 2020/0046901 A1 | 2/2020 | Alexandersson |
| 2020/0046907 A1 | 2/2020 | Schader et al. |
| 2020/0061302 A1 | 2/2020 | Alexandersson |
| 2021/0085884 A1 | 3/2021 | Liniger et al. |

FOREIGN PATENT DOCUMENTS

| | | |
|---|---|---|
| BR | PI0815136 B1 | 1/2019 |
| CA | 2823739 C | 5/2019 |
| CH | 712459 A2 | 11/2017 |
| CH | 714525 A2 | 6/2019 |
| CH | 714526 A2 | 6/2019 |
| CH | 714527 A2 | 6/2019 |
| CH | 714528 A2 | 6/2019 |
| CN | 103596612 A | 2/2014 |
| CN | 104780906 A | 7/2015 |
| CN | 109331295 A | 2/2019 |
| CN | 209575432 U | 11/2019 |
| CN | 209734664 U | 12/2019 |
| EP | 1044698 A1 | 10/2000 |
| EP | 1715903 B1 | 11/2006 |
| EP | 2043711 A2 | 4/2009 |
| EP | 1755706 B1 | 3/2010 |
| EP | 2162170 B1 | 3/2011 |
| EP | 2438947 A1 | 4/2012 |
| EP | 2324875 B1 | 4/2014 |
| EP | 2455124 B1 | 6/2014 |
| EP | 2745866 B1 | 10/2016 |
| EP | 2903670 B1 | 4/2017 |
| EP | 2680906 B1 | 11/2017 |
| EP | 2691134 B1 | 1/2018 |
| EP | 3030287 B1 | 1/2018 |
| EP | 3446734 A1 | 2/2019 |
| EP | 2903667 B1 | 7/2019 |
| EP | 3325051 B1 | 7/2019 |
| EP | 2023983 B1 | 8/2019 |
| EP | 3368101 B1 | 9/2019 |
| EP | 3374008 B1 | 9/2019 |
| EP | 3407939 B1 | 10/2019 |
| EP | 3416706 B1 | 6/2020 |
| EP | 3552642 B1 | 1/2021 |
| EP | 2918299 B1 | 9/2021 |
| EP | 2695630 B1 | 1/2022 |
| EP | 3618904 B1 | 1/2022 |
| GB | 257031 A | 8/1926 |
| GB | 2321051 A | 7/1998 |
| GB | 2493432 B | 4/2013 |
| GB | 2538068 A | 11/2016 |
| GB | 2570319 B | 1/2021 |
| IT | 920120 A1 | 5/1994 |
| JP | 6456820 B2 | 1/2019 |
| WO | 9117783 A1 | 11/1991 |
| WO | WO1994011041 | 5/1994 |
| WO | 0062848 A1 | 10/2000 |
| WO | 2005070481 A1 | 8/2005 |
| WO | 2005115508 A1 | 12/2005 |
| WO | 2006017732 A2 | 2/2006 |
| WO | 2006057604 A1 | 6/2006 |
| WO | 2006079064 A1 | 7/2006 |
| WO | 2007066152 A2 | 6/2007 |
| WO | 2007132353 A2 | 11/2007 |
| WO | 2008016381 A1 | 2/2008 |
| WO | 2009007229 A1 | 1/2009 |
| WO | 2009019440 A1 | 2/2009 |
| WO | 2009040605 A1 | 4/2009 |
| WO | 2009102596 A2 | 8/2009 |
| WO | 2010007395 A1 | 1/2010 |
| WO | 2010136076 A1 | 12/2010 |
| WO | 2011047298 A2 | 4/2011 |
| WO | 2011078851 A1 | 6/2011 |
| WO | 2011123024 A1 | 10/2011 |
| WO | 2011149455 A1 | 12/2011 |
| WO | 2012003516 A2 | 1/2012 |
| WO | 2012085017 A2 | 6/2012 |
| WO | 2012085034 A2 | 6/2012 |
| WO | 2012101629 A1 | 8/2012 |
| WO | 2012103140 A1 | 8/2012 |
| WO | 2012117255 A1 | 9/2012 |
| WO | 2012129174 A1 | 9/2012 |
| WO | 2012137803 A1 | 10/2012 |
| WO | 2013012745 A1 | 1/2013 |
| WO | 2013016832 A1 | 2/2013 |
| WO | 2013089620 A1 | 6/2013 |
| WO | 2013152323 A1 | 10/2013 |
| WO | 2013167494 A1 | 11/2013 |
| WO | 2013169800 A1 | 11/2013 |
| WO | 2013169804 A1 | 11/2013 |
| WO | 2013078771 | 12/2013 |
| WO | 2013178512 A1 | 12/2013 |
| WO | 2014009705 A1 | 1/2014 |
| WO | 2014053451 A1 | 4/2014 |
| WO | 2014124427 A1 | 8/2014 |
| WO | 2014124464 A1 | 8/2014 |
| WO | 2014146209 A1 | 9/2014 |
| WO | 2014146210 A1 | 9/2014 |
| WO | 2014150201 A1 | 9/2014 |
| WO | 2015004049 A1 | 1/2015 |
| WO | 2015018578 A1 | 2/2015 |
| WO | 2015075399 A1 | 5/2015 |
| W@ | 2015078866 A1 | 6/2015 |
| WO | 2015090320 A2 | 6/2015 |
| WO | 2015110533 A2 | 7/2015 |
| WO | 2015113172 A1 | 8/2015 |
| WO | 2016075254 A1 | 5/2016 |
| WO | 2016087187 A1 | 6/2016 |
| WO | 2016174245 A1 | 11/2016 |
| WO | 2016177390 A1 | 11/2016 |
| WO | 2016193343 A1 | 12/2016 |
| WO | 2016193349 A1 | 12/2016 |
| WO | 2016193374 A1 | 12/2016 |
| WO | 2017029032 A1 | 2/2017 |
| WO | 2017051113 A1 | 3/2017 |
| WO | 2017078166 A1 | 5/2017 |
| WO | 2016025327 A1 | 6/2017 |
| WO | 2017089256 A1 | 6/2017 |
| WO | 2017089259 A1 | 6/2017 |
| WO | 2017186435 A1 | 11/2017 |
| WO | 2017186472 A1 | 11/2017 |
| WO | 2017191159 A1 | 11/2017 |
| WO | 2017191177 A1 | 11/2017 |
| WO | 2017207224 A1 | 12/2017 |
| WO | 2017211628 A1 | 12/2017 |
| WO | 2017223354 A1 | 12/2017 |
| WO | 2018010947 A1 | 1/2018 |
| WO | 2018018164 A1 | 2/2018 |
| WO | 2018065708 A1 | 4/2018 |
| WO | 2018068959 A1 | 4/2018 |
| WO | 2018077672 A1 | 5/2018 |
| WO | 2018091257 A1 | 5/2018 |
| WO | 2018142167 A1 | 8/2018 |
| WO | 2018167490 A1 | 9/2018 |
| WO | 2018215270 A2 | 11/2018 |
| WO | 2018224637 A1 | 12/2018 |
| WO | 2019043502 A1 | 3/2019 |
| WO | 2019046436 A1 | 3/2019 |
| WO | 2019058382 A1 | 3/2019 |
| WO | 2019086376 A1 | 5/2019 |
| WO | 2019126454 A1 | 6/2019 |
| WO | 2019141573 A1 | 7/2019 |
| WO | 2019160933 A1 | 8/2019 |
| WO | 2019179895 A1 | 9/2019 |
| WO | 2019189278 A1 | 10/2019 |
| WO | 2019191110 A1 | 10/2019 |
| WO | 2019224782 | 11/2019 |
| WO | 2019224783 A1 | 11/2019 |
| WO | 2019224784 | 11/2019 |

(56) References Cited

FOREIGN PATENT DOCUMENTS

| | | |
|---|---|---|
| WO | 2019224785 | 11/2019 |
| WO | 2019238806 A1 | 12/2019 |
| WO | 2020006751 A1 | 1/2020 |
| WO | 2020015985 A1 | 1/2020 |
| WO | 2020015986 A1 | 1/2020 |
| WO | 2020016158 A1 | 1/2020 |
| WO | 2020023444 A1 | 1/2020 |
| WO | 2022130338 | 6/2022 |

* cited by examiner

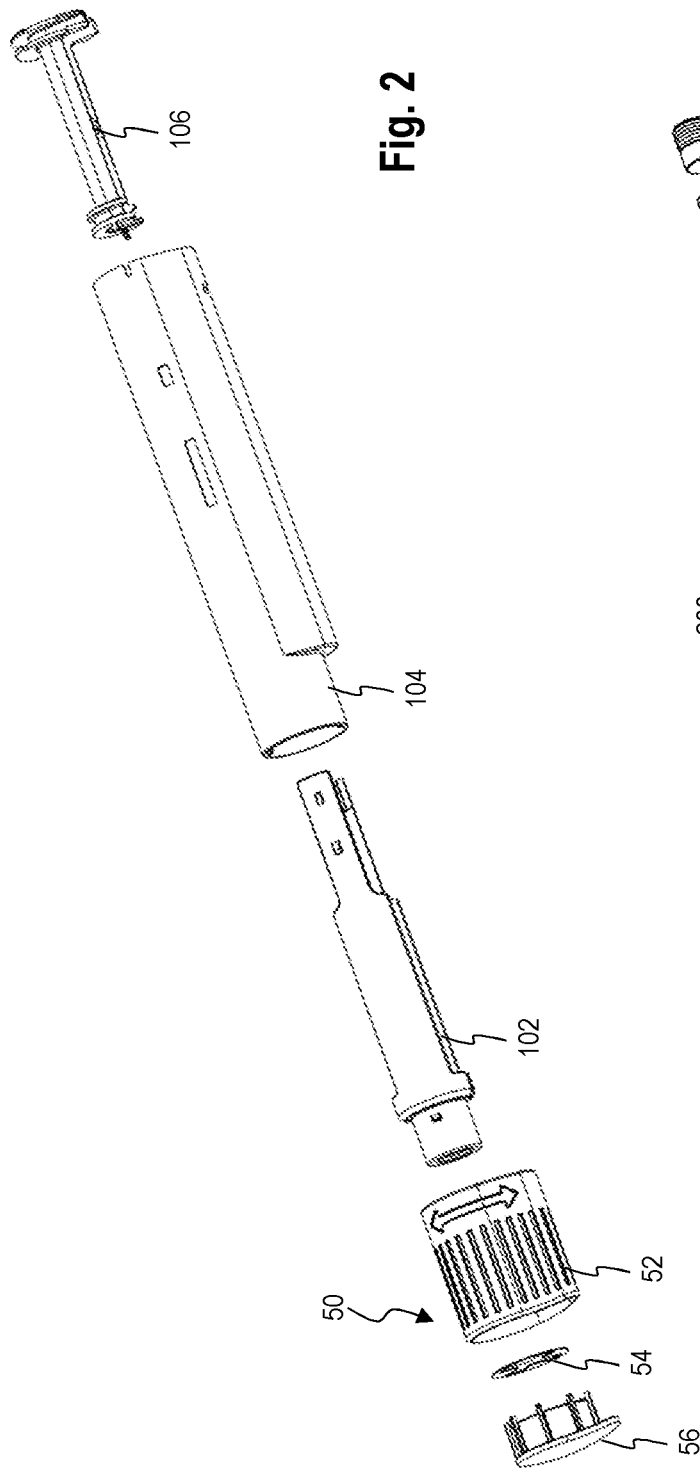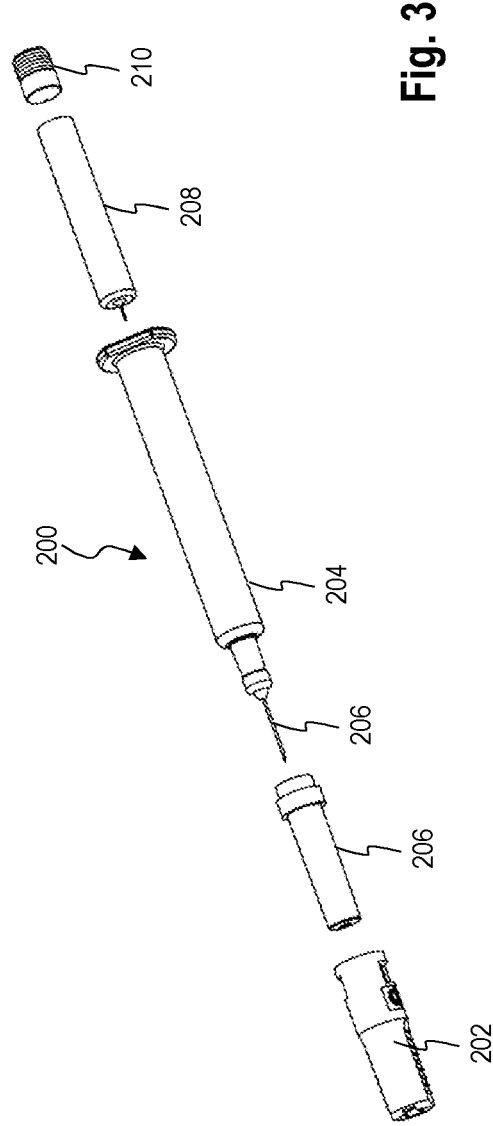

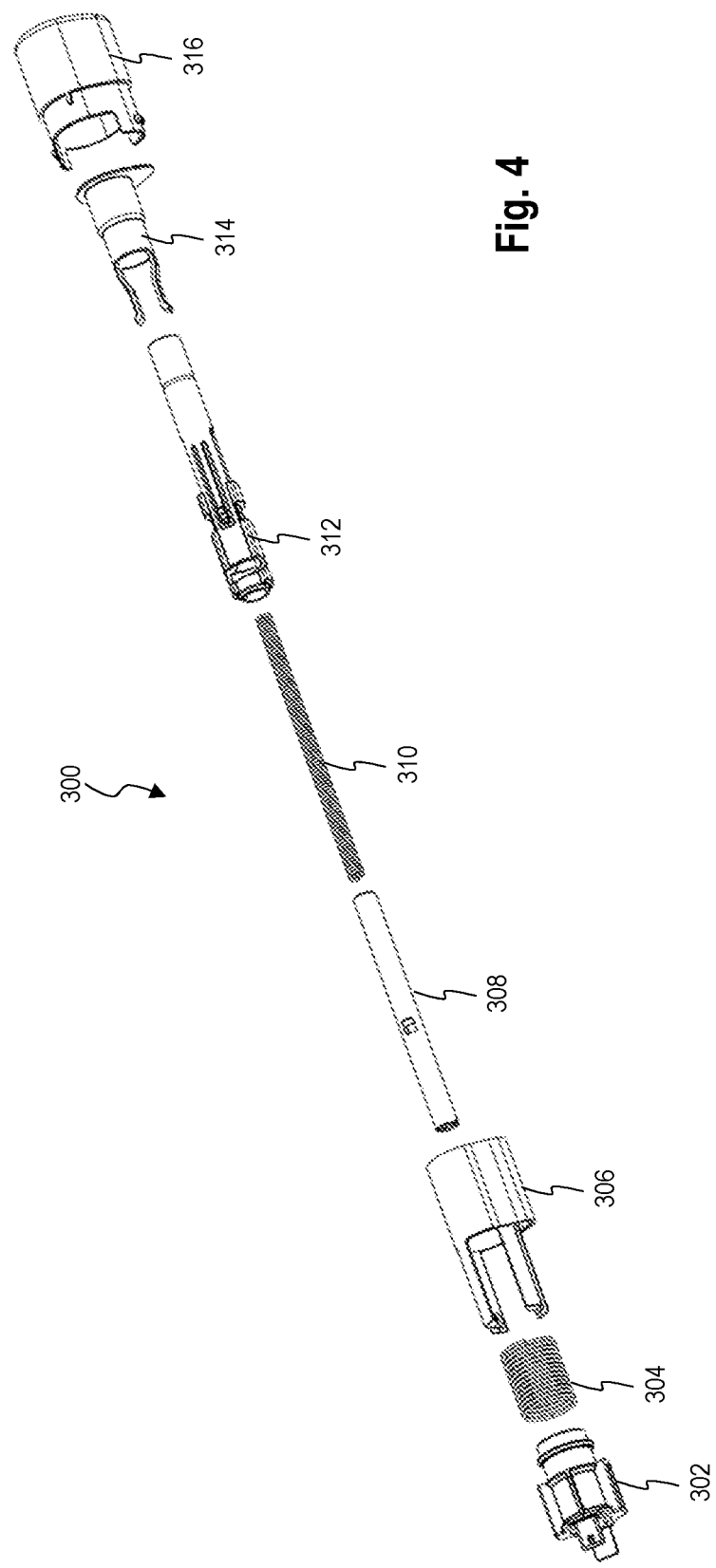

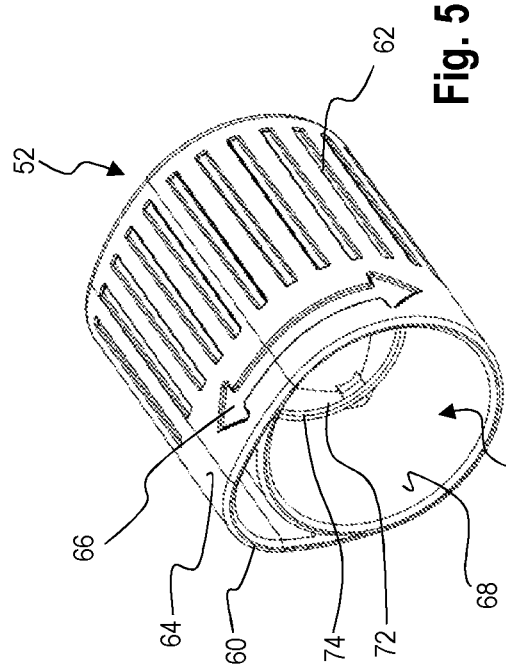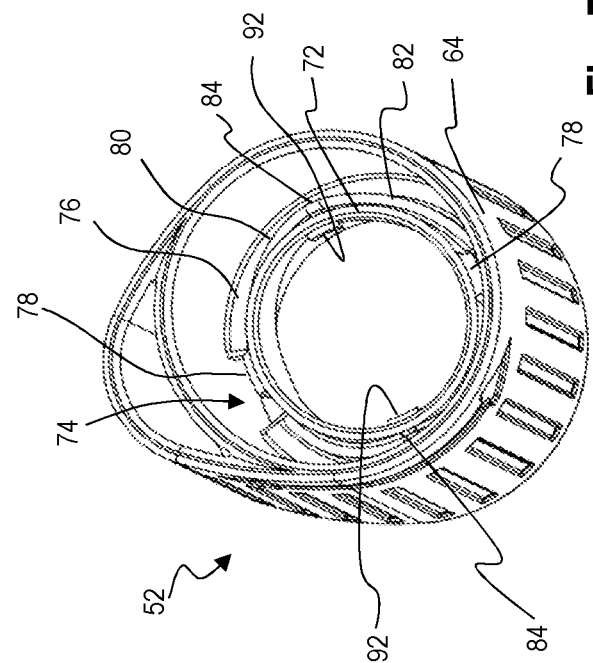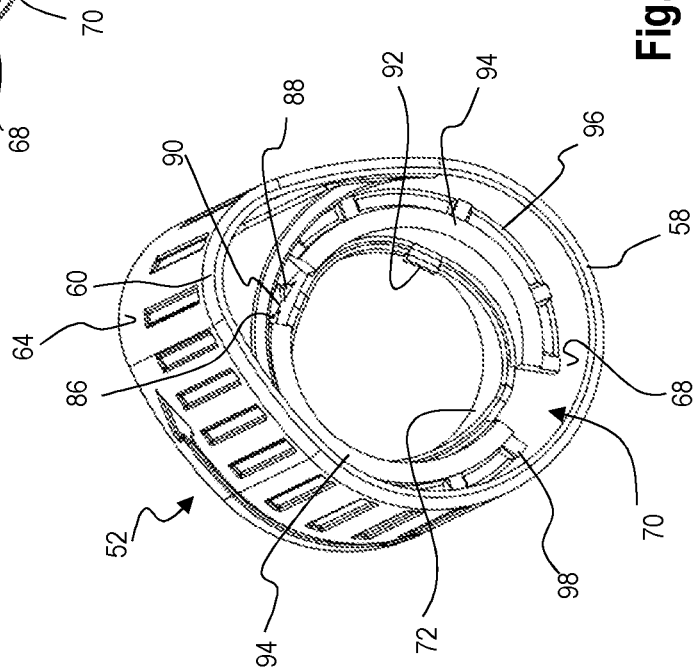

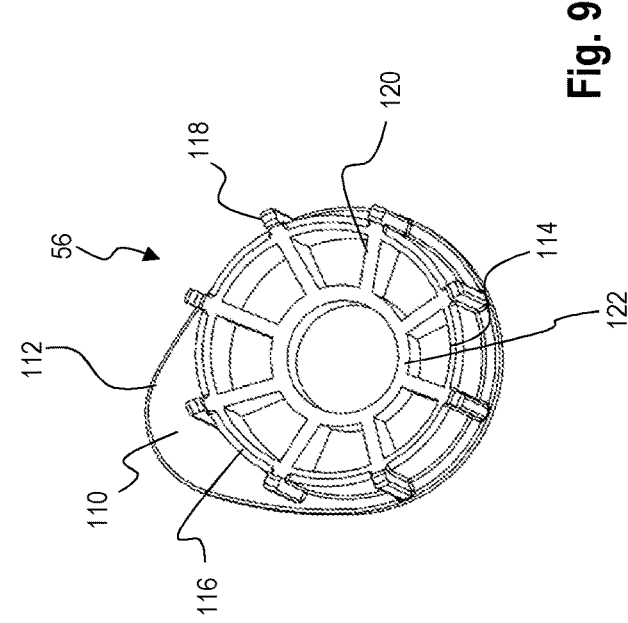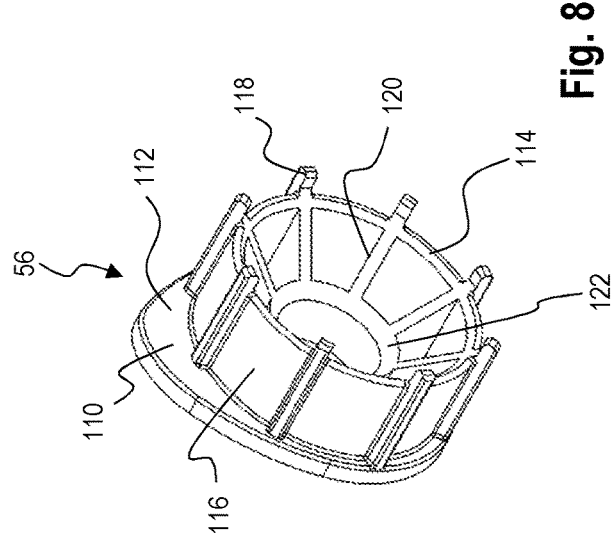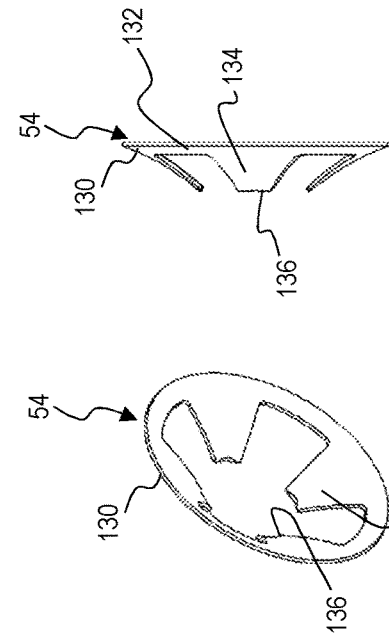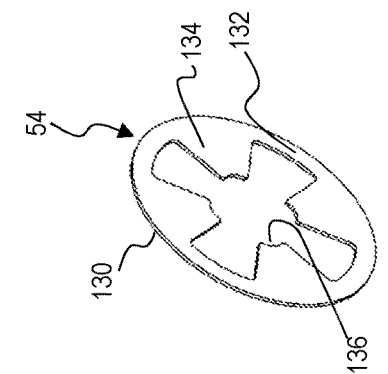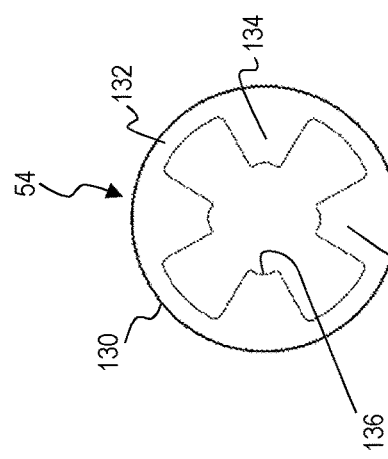

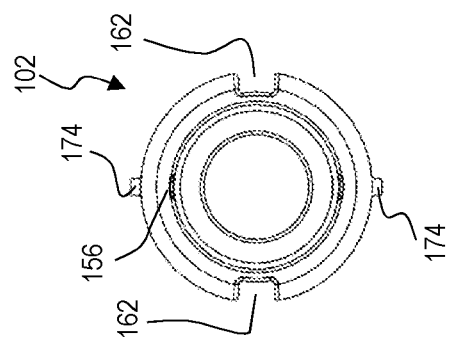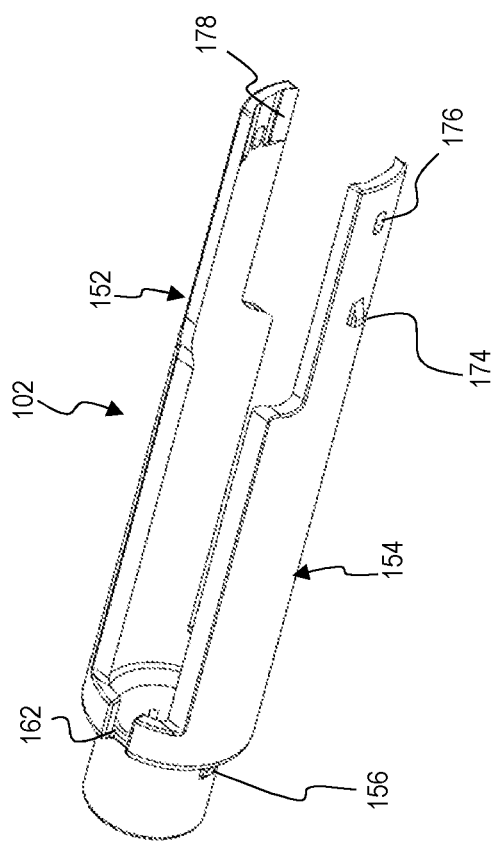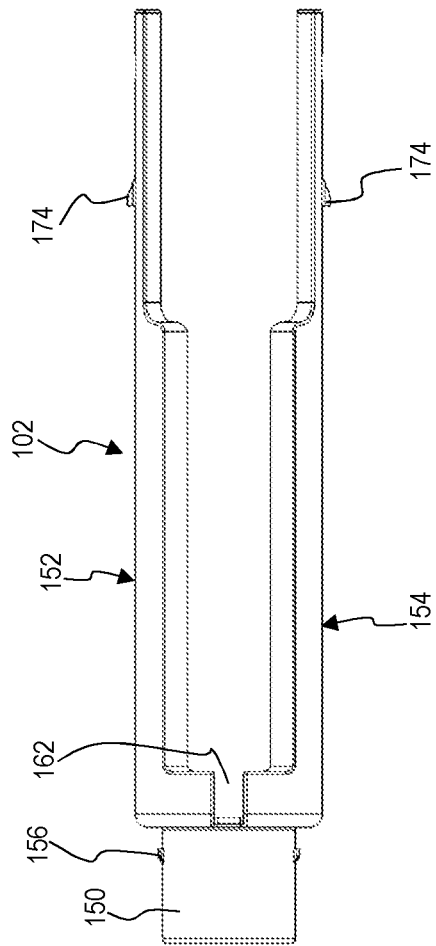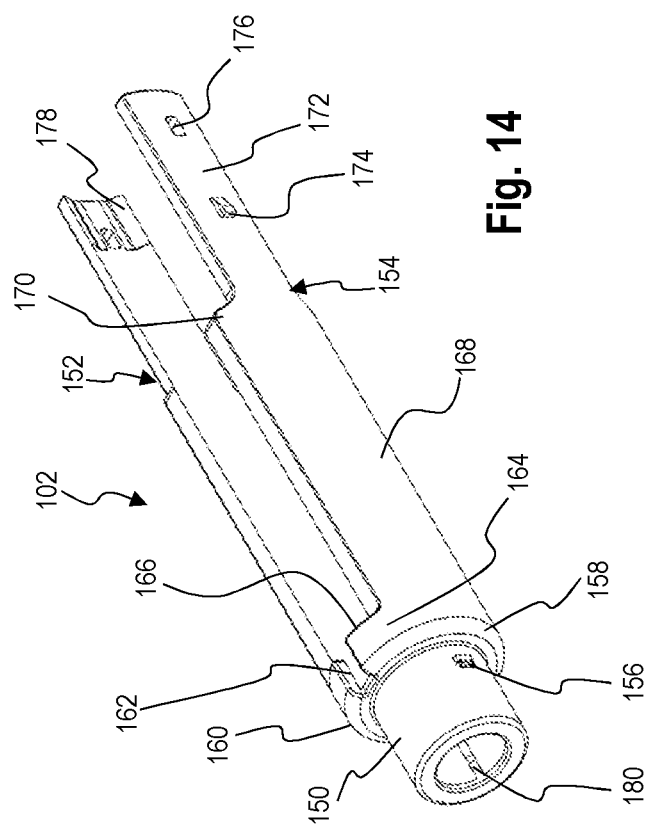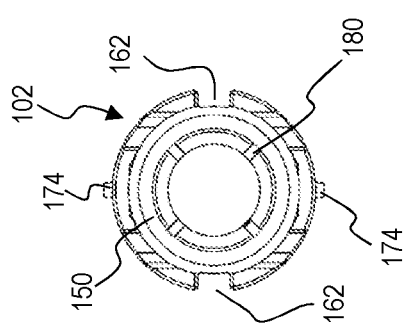

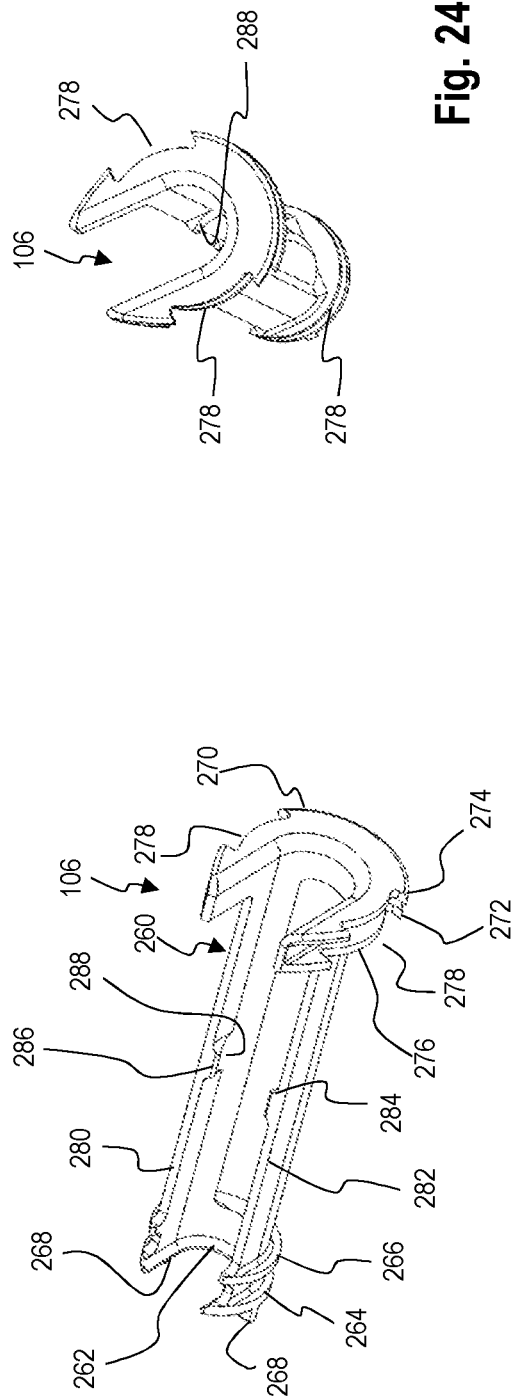
Fig. 24
Fig. 23
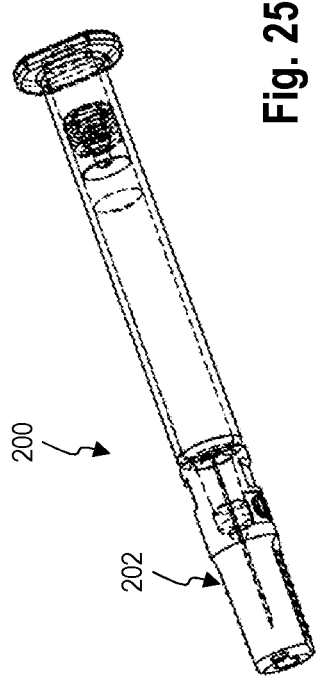
Fig. 25

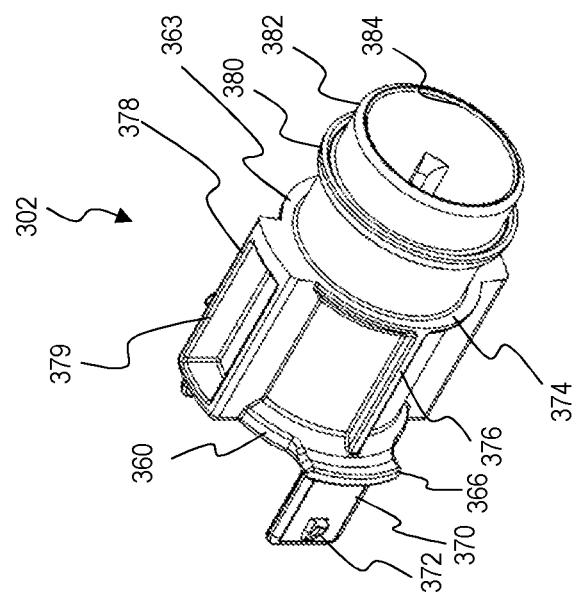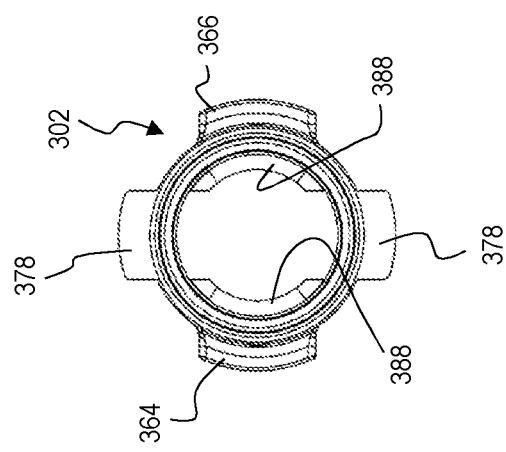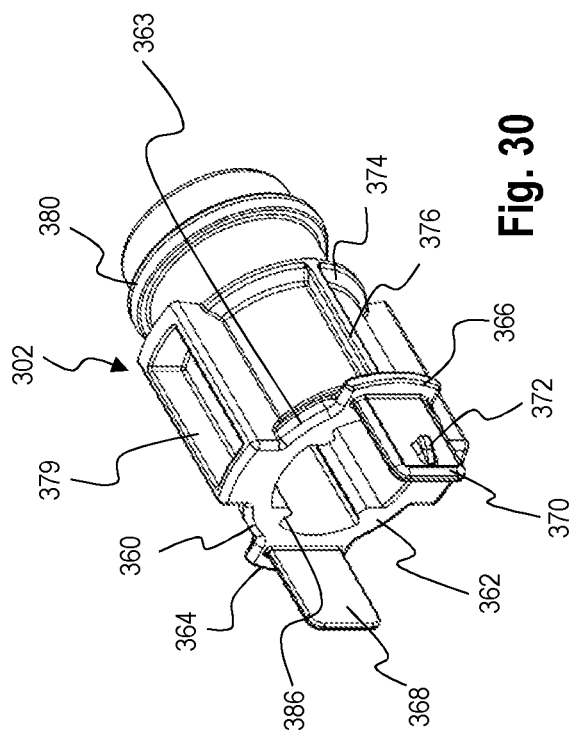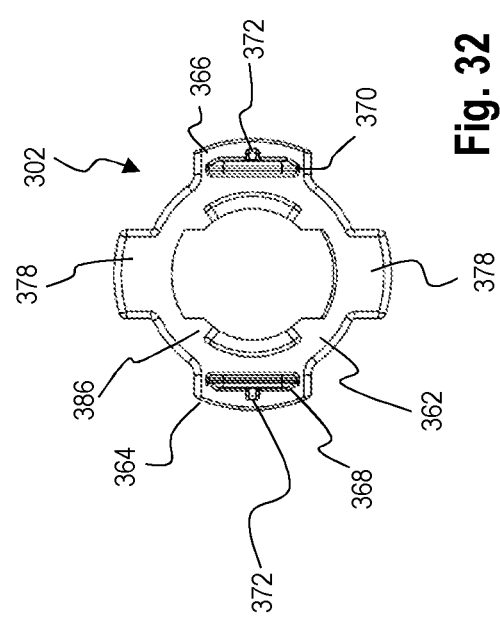

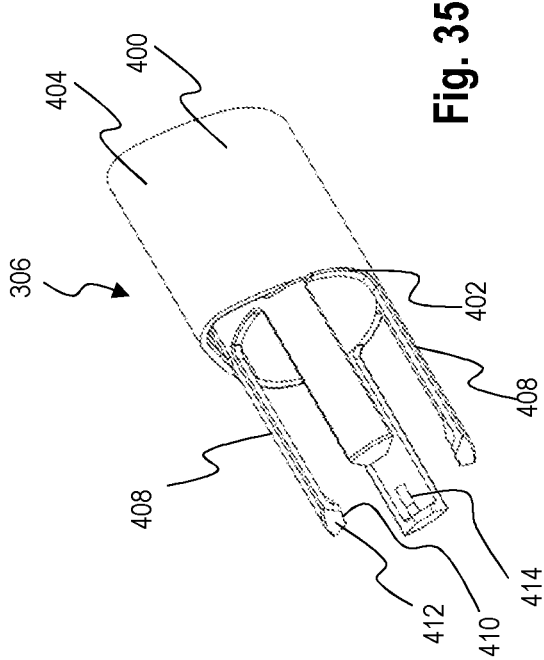
Fig. 35
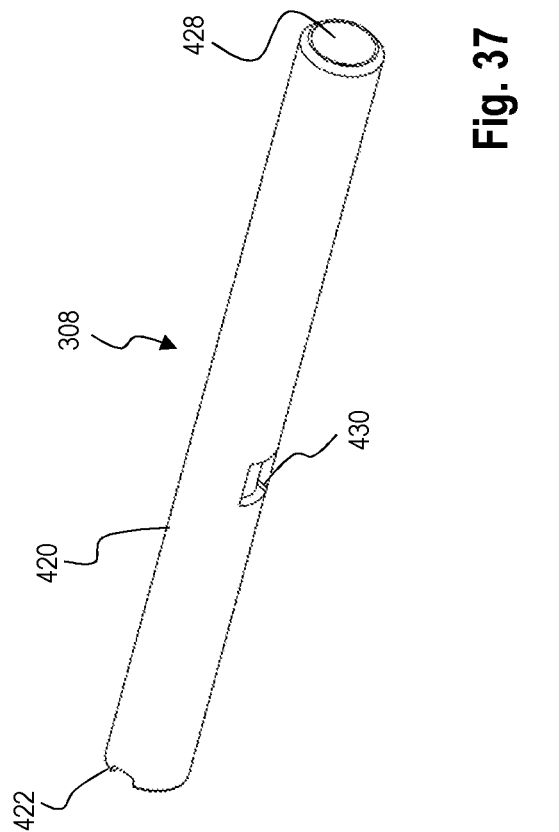
Fig. 37
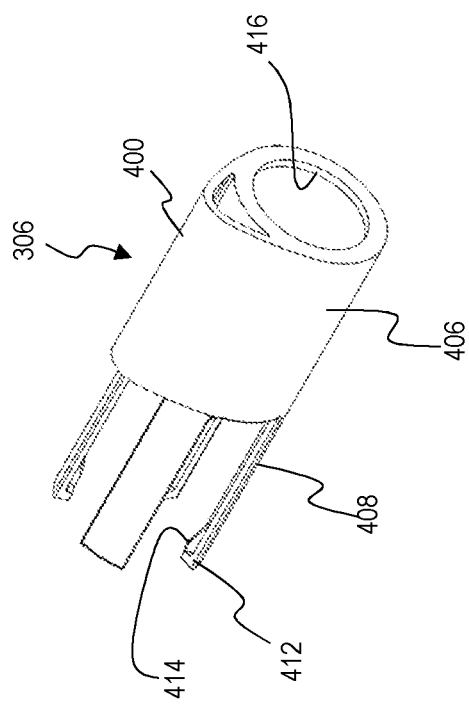
Fig. 34
Fig. 36

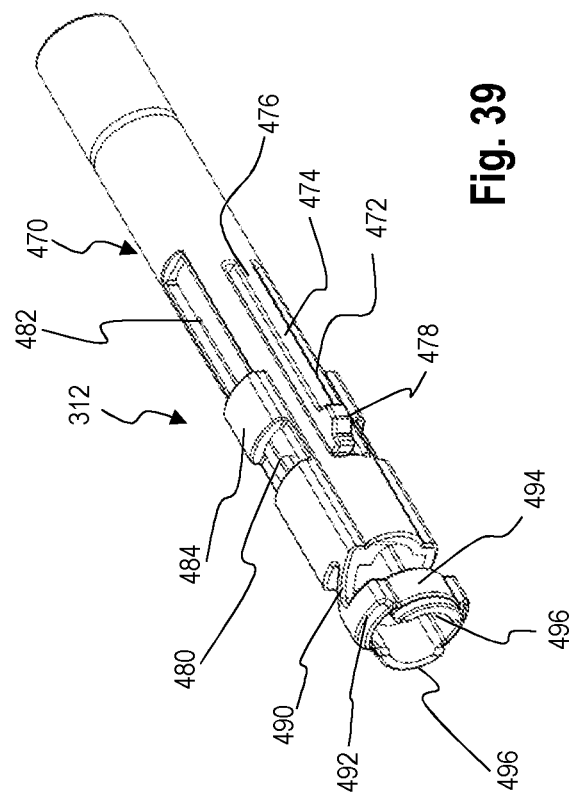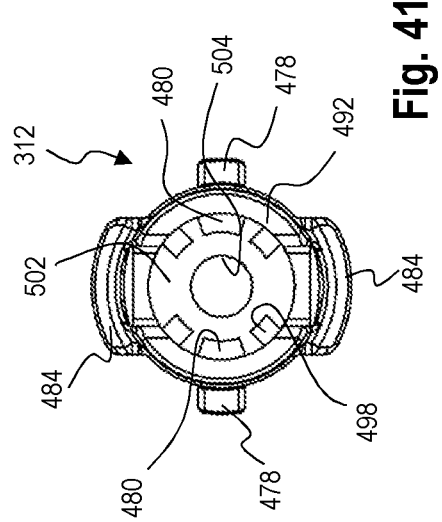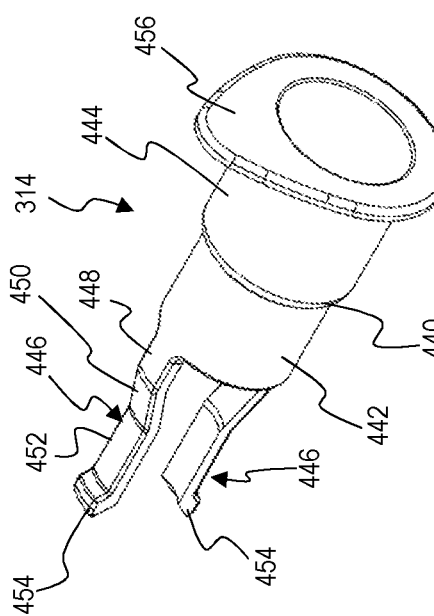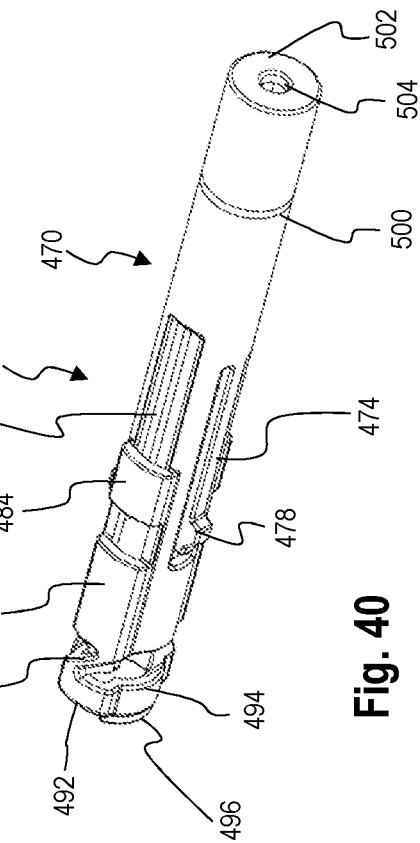

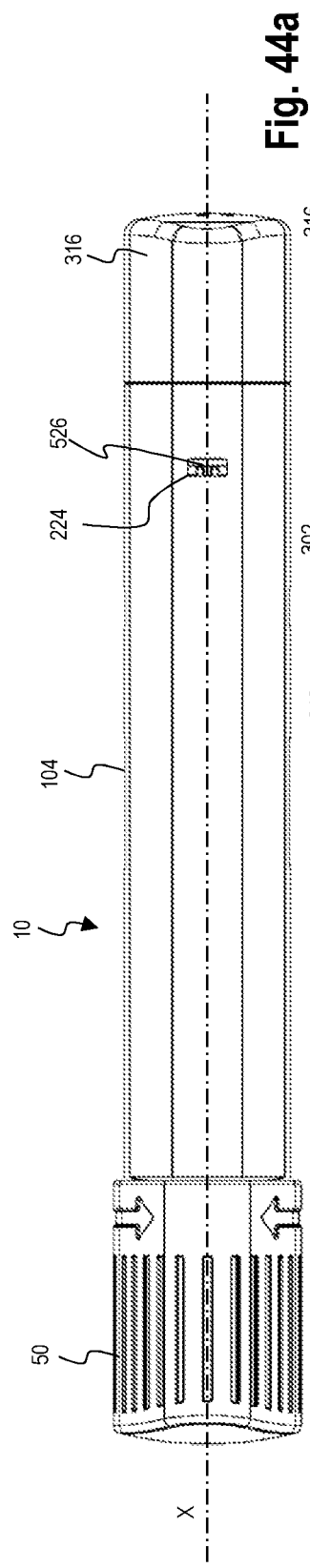
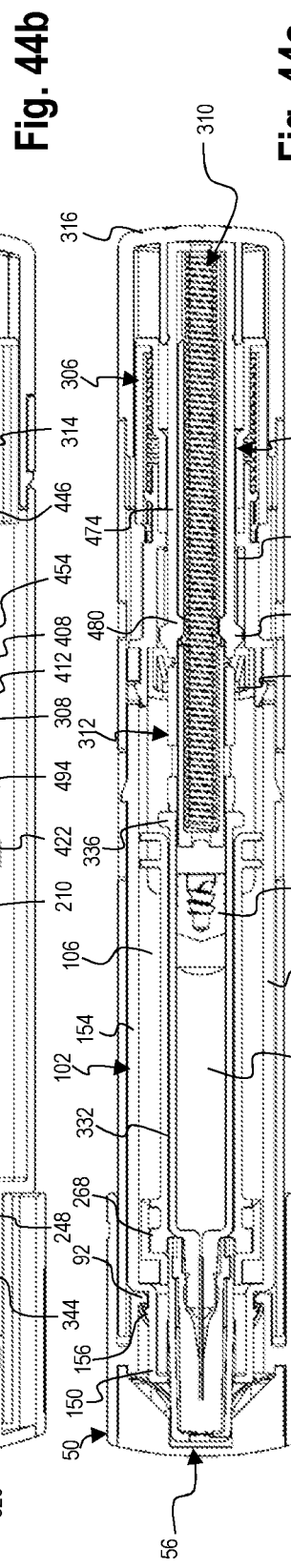
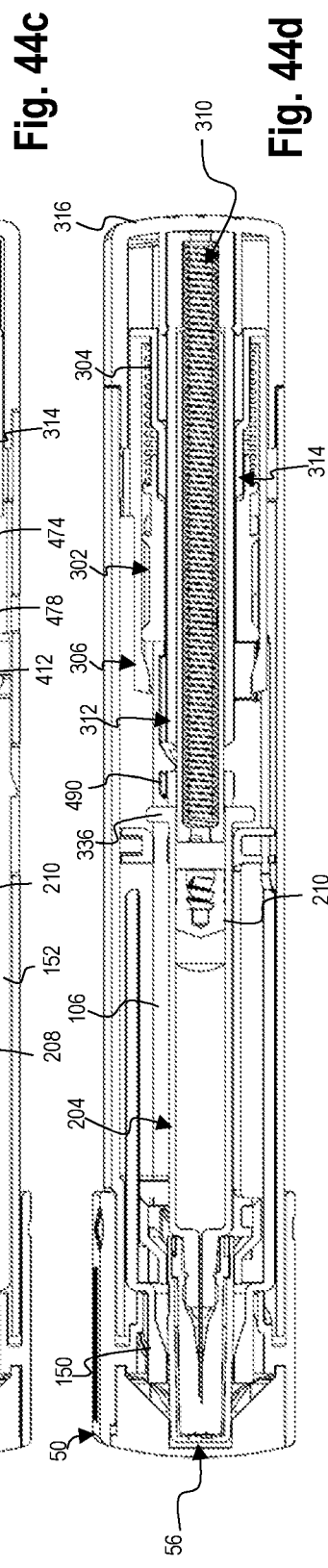
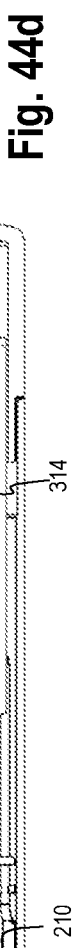
Fig. 44a
Fig. 44b
Fig. 44c
Fig. 44d

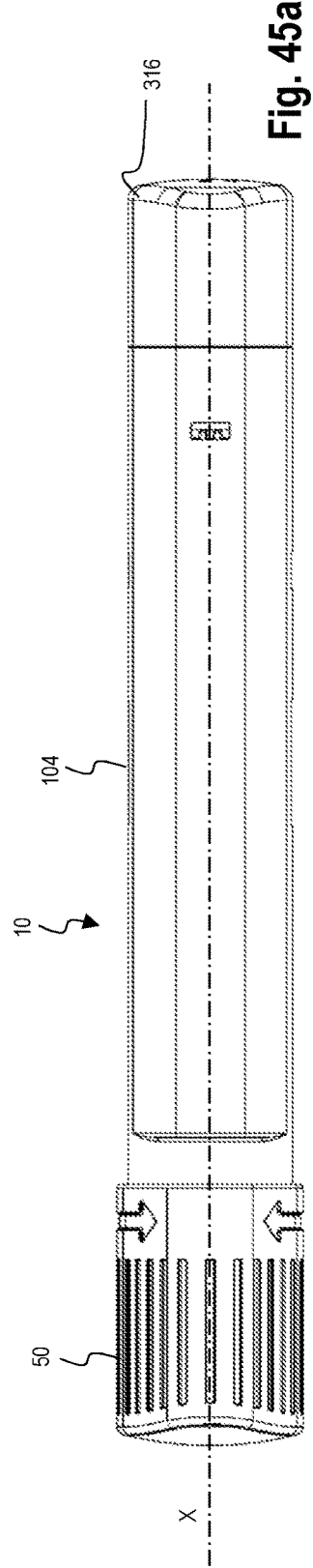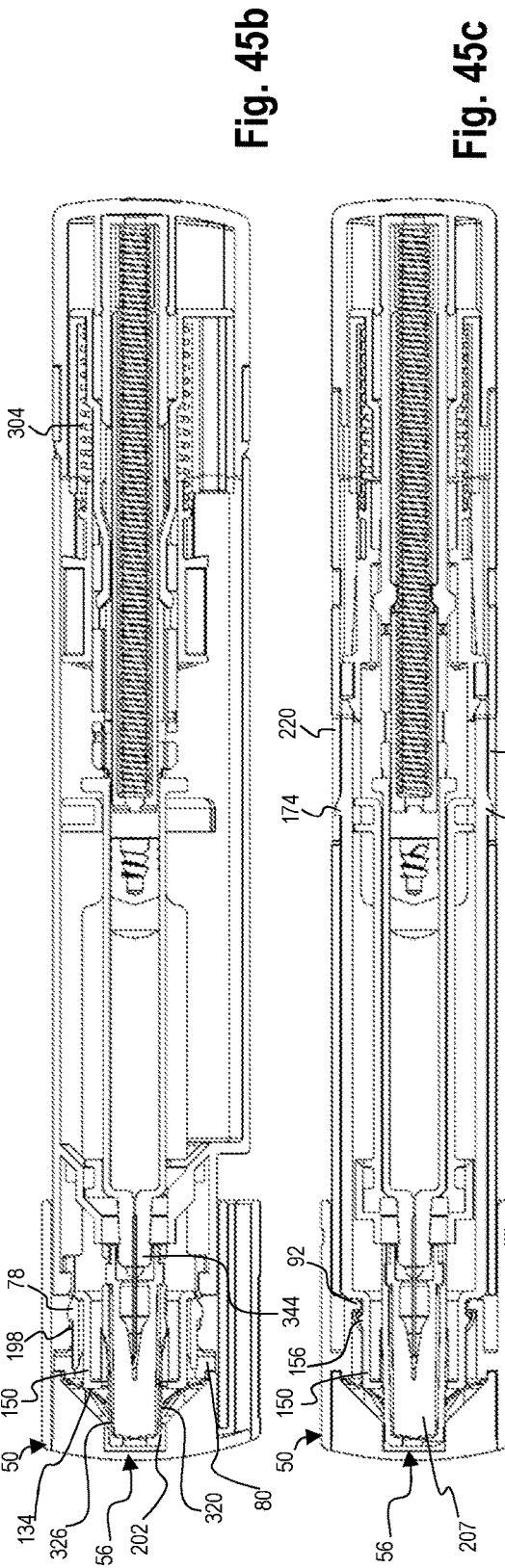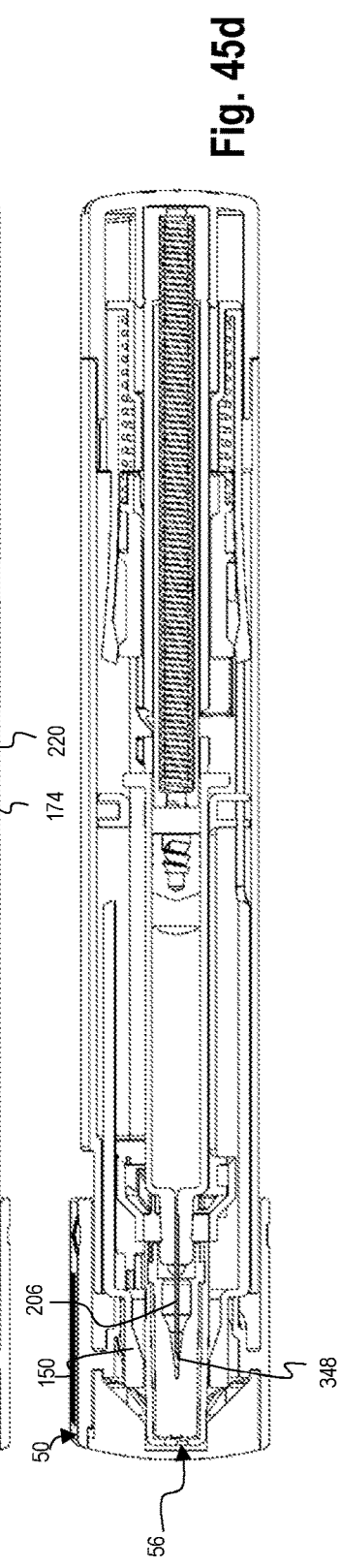

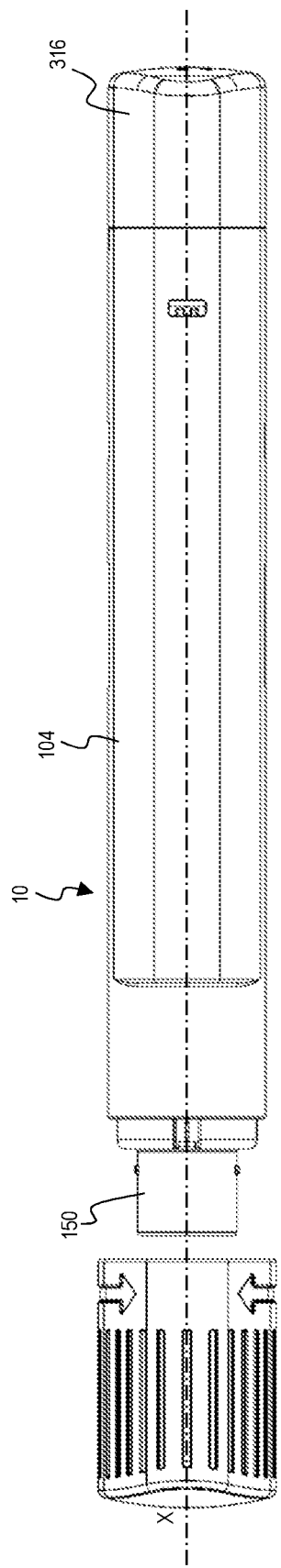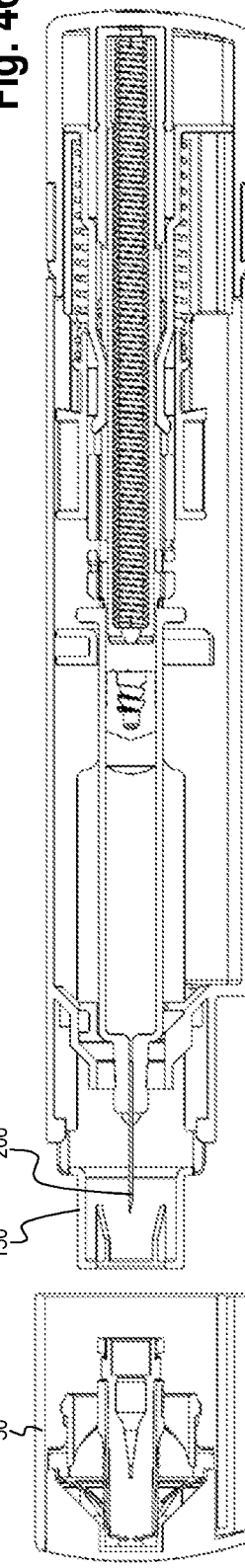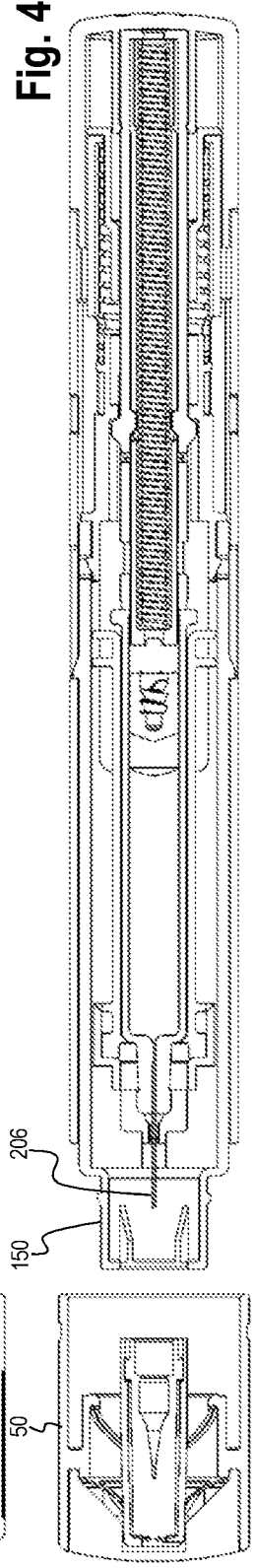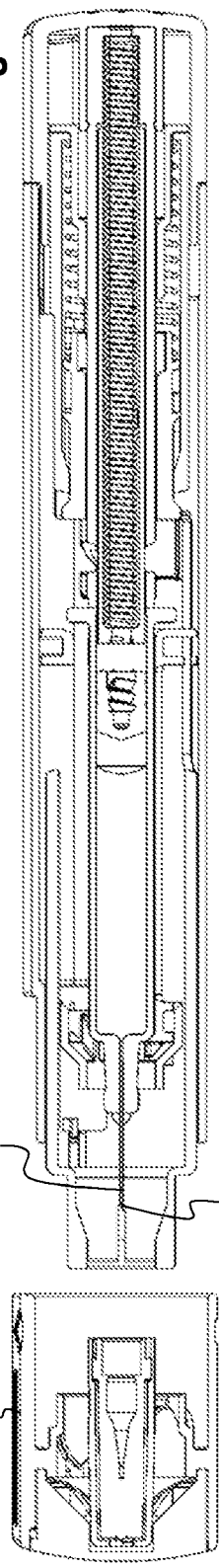

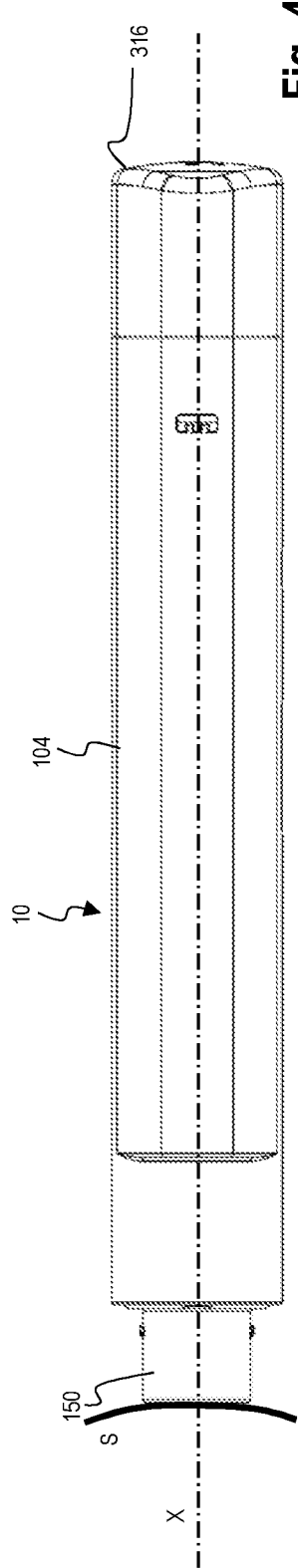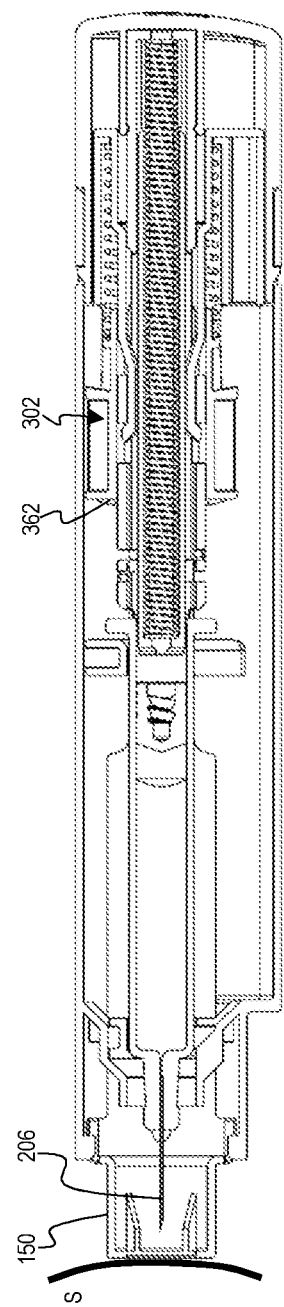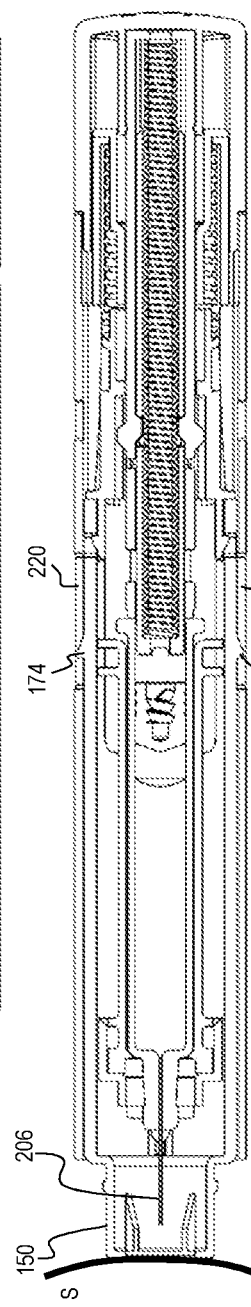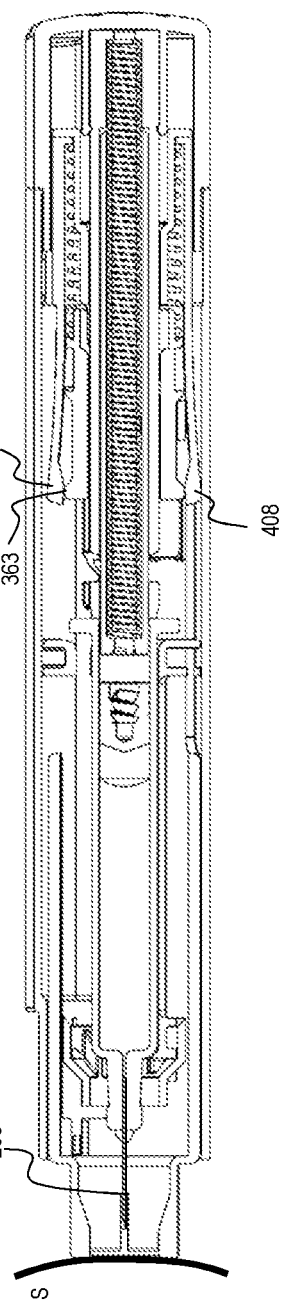

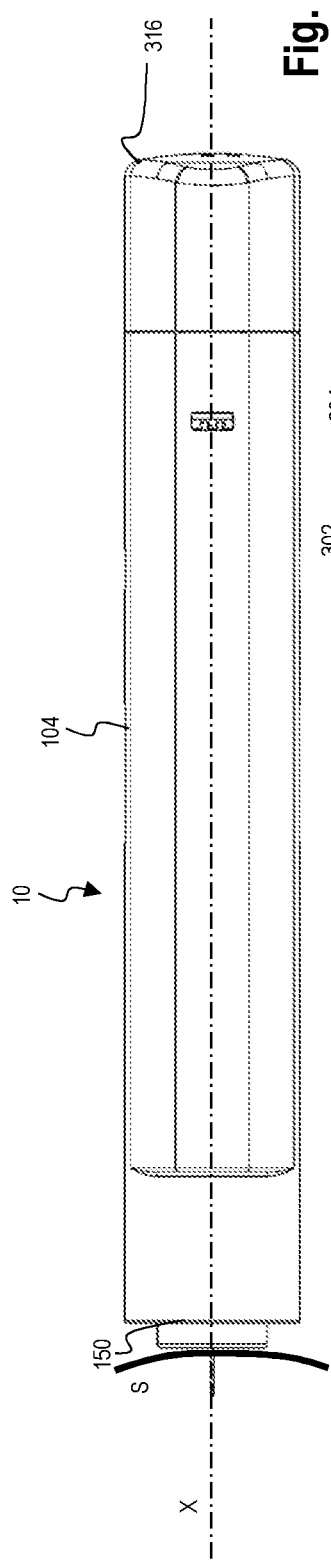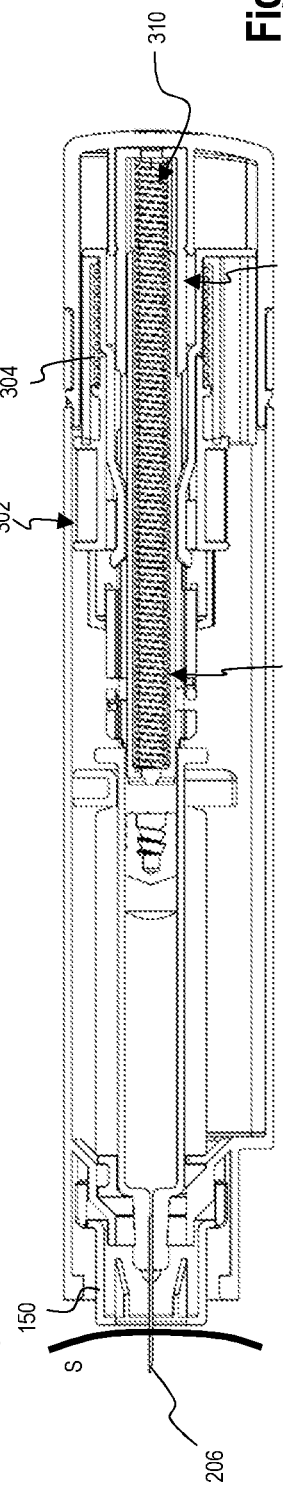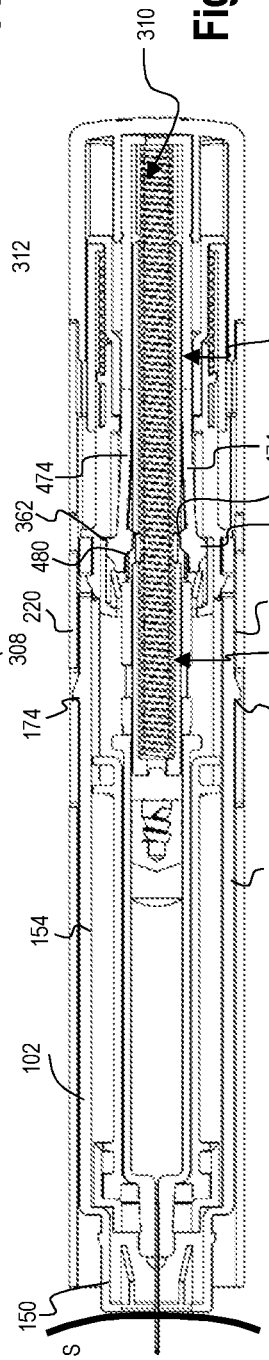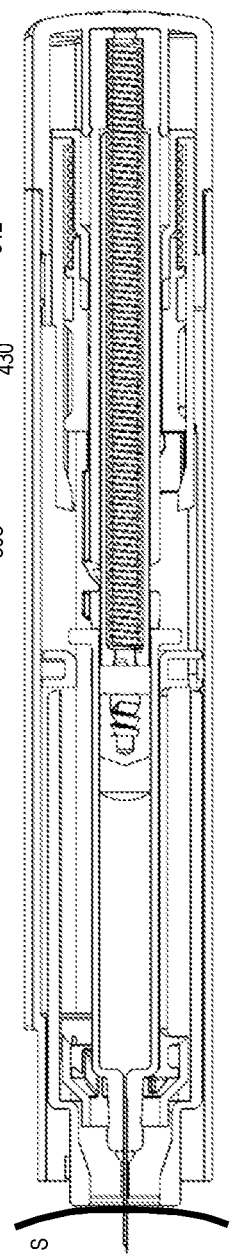

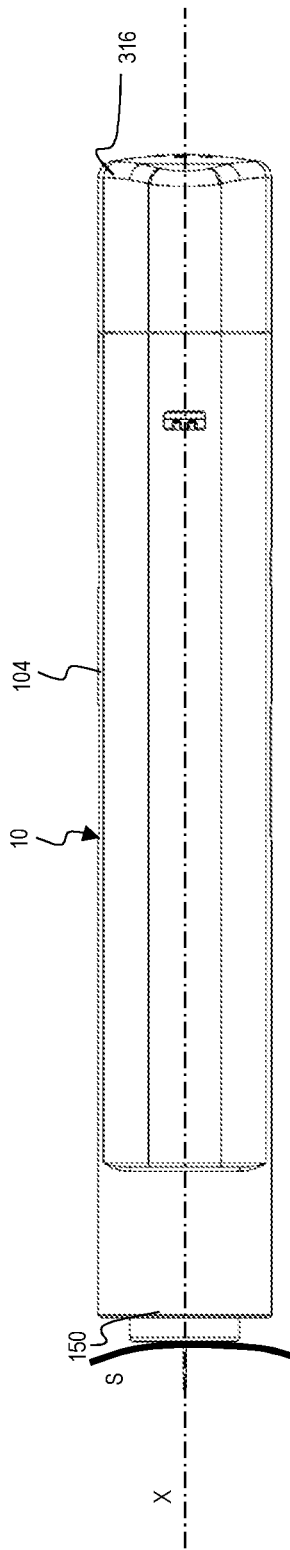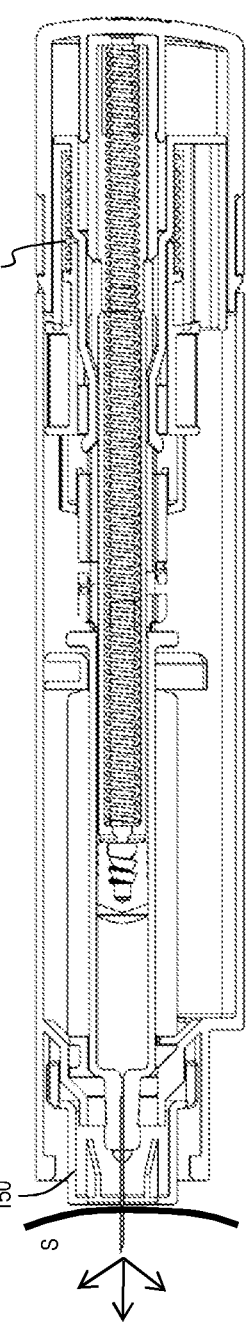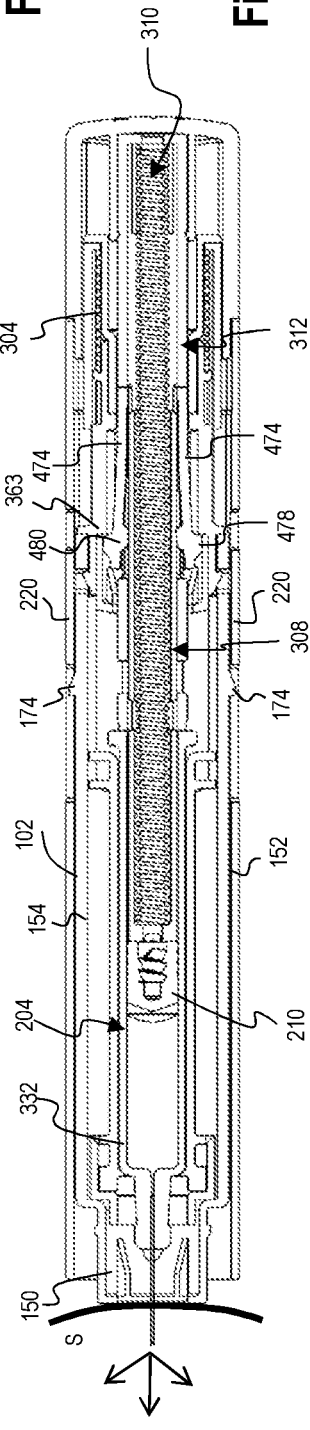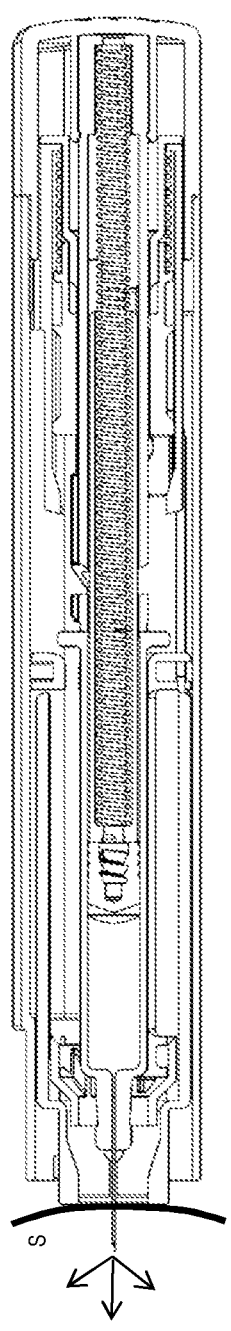

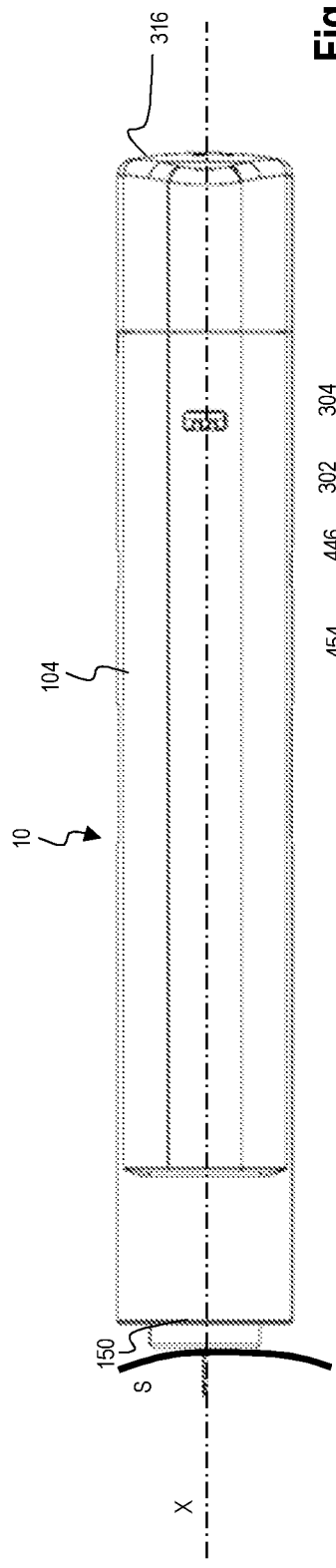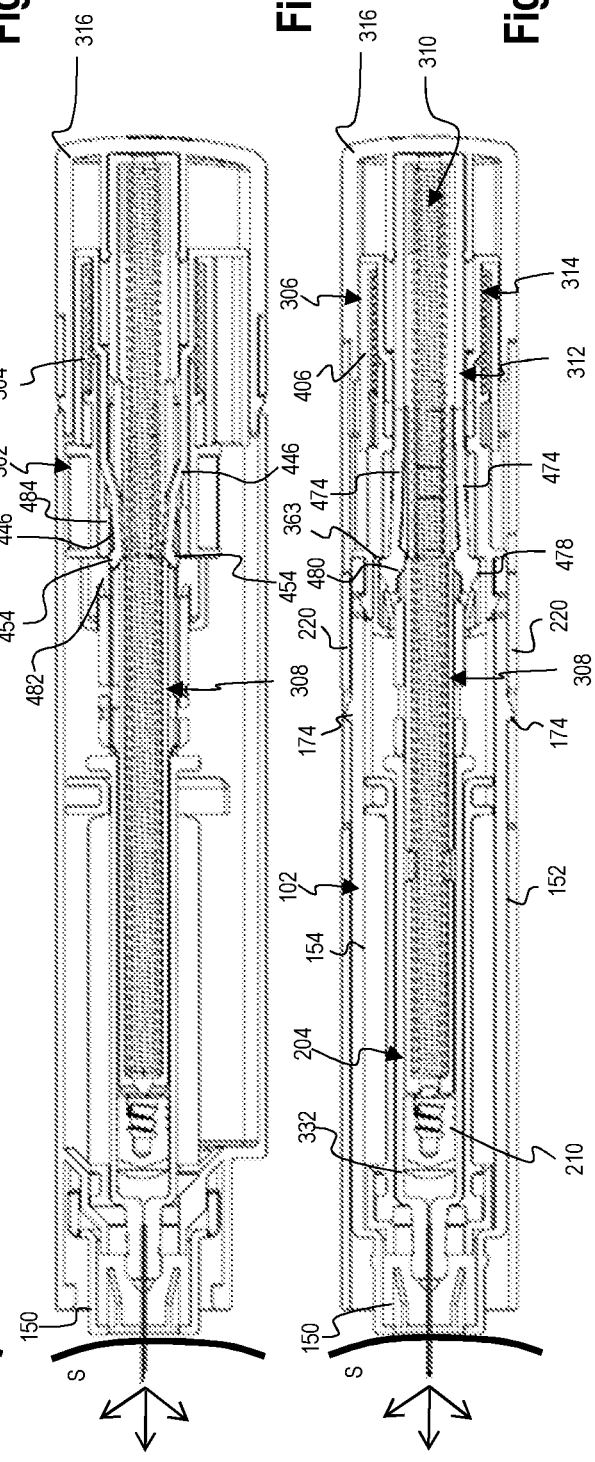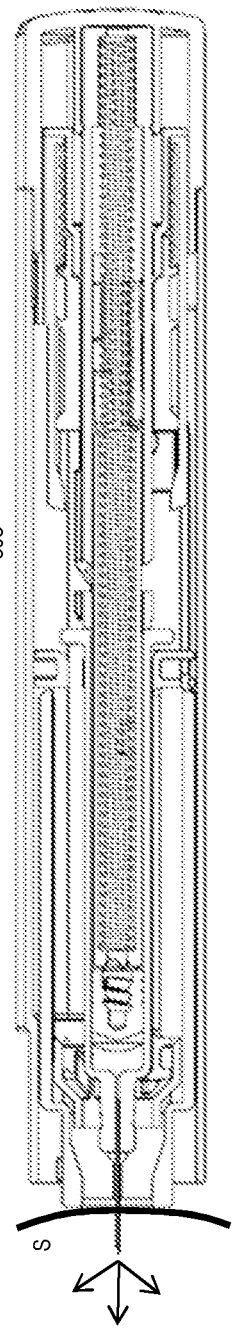

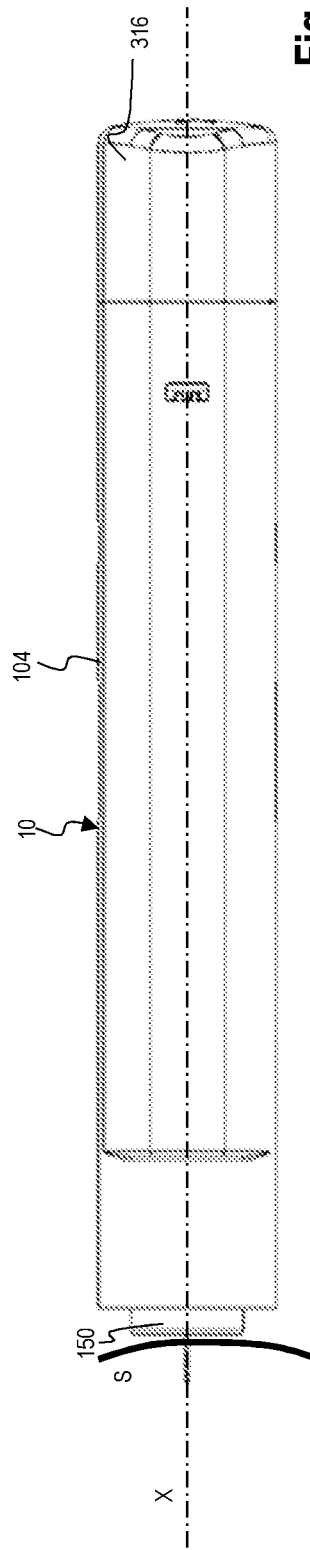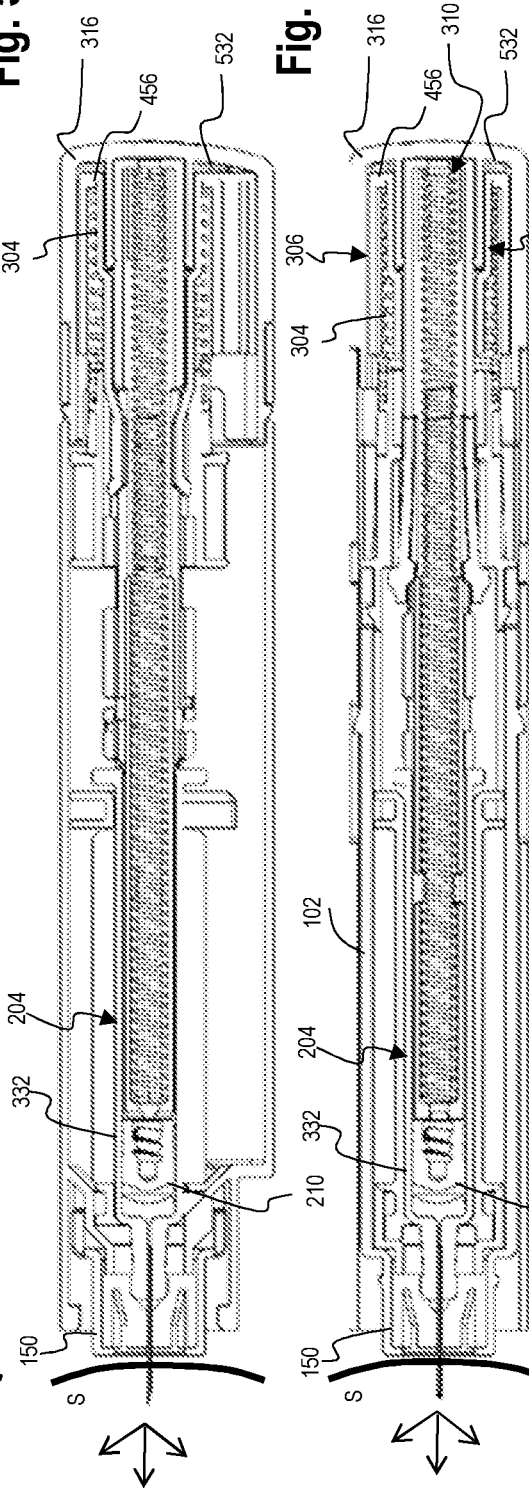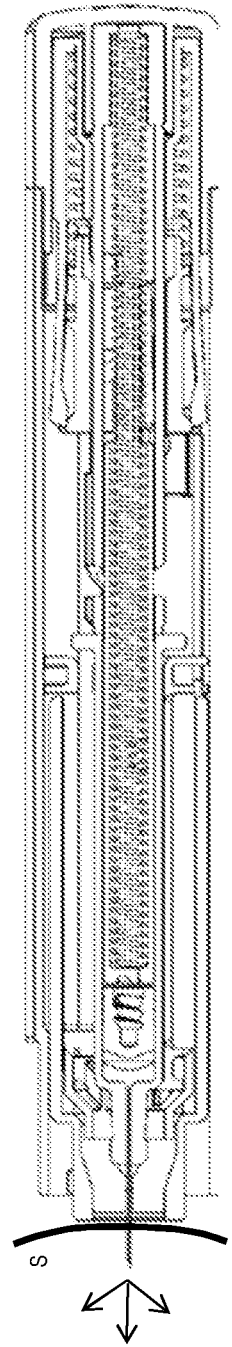

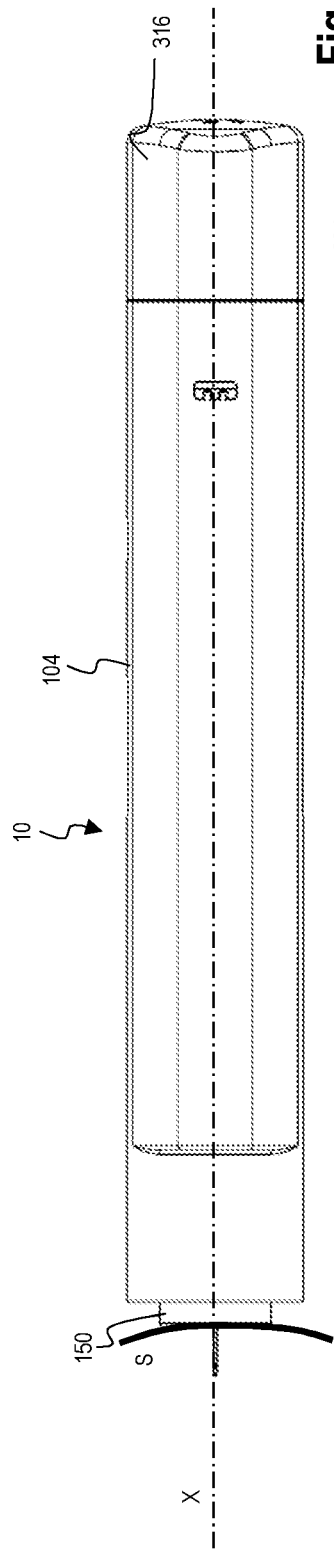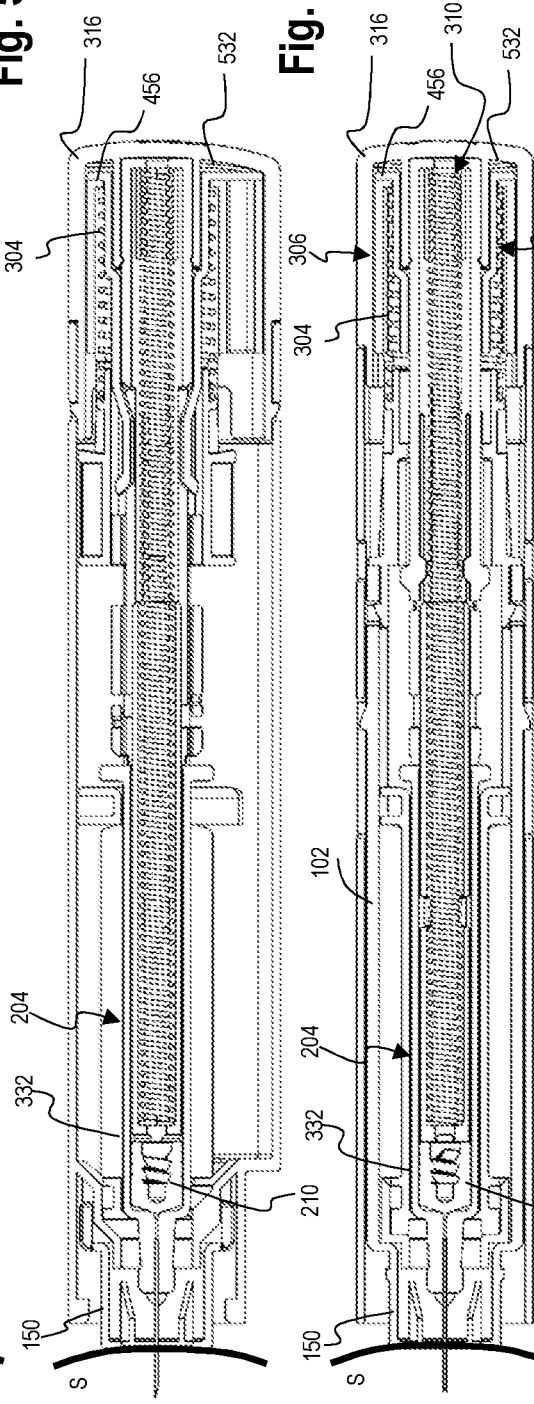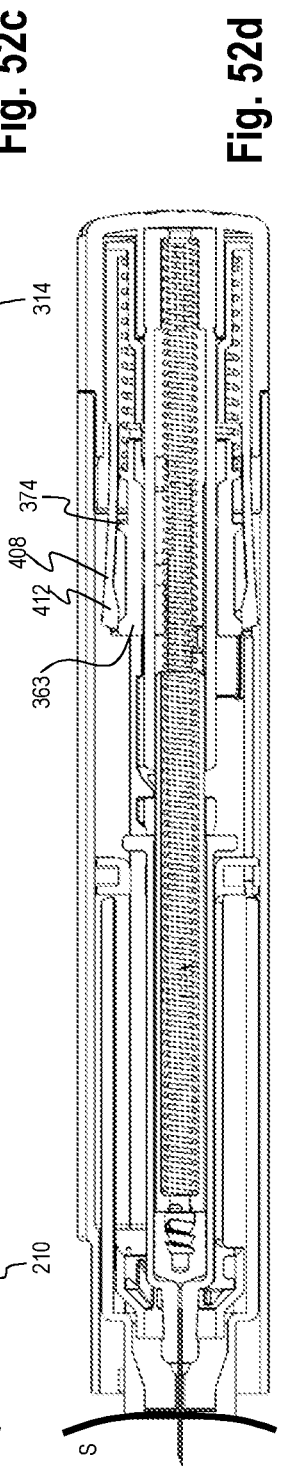

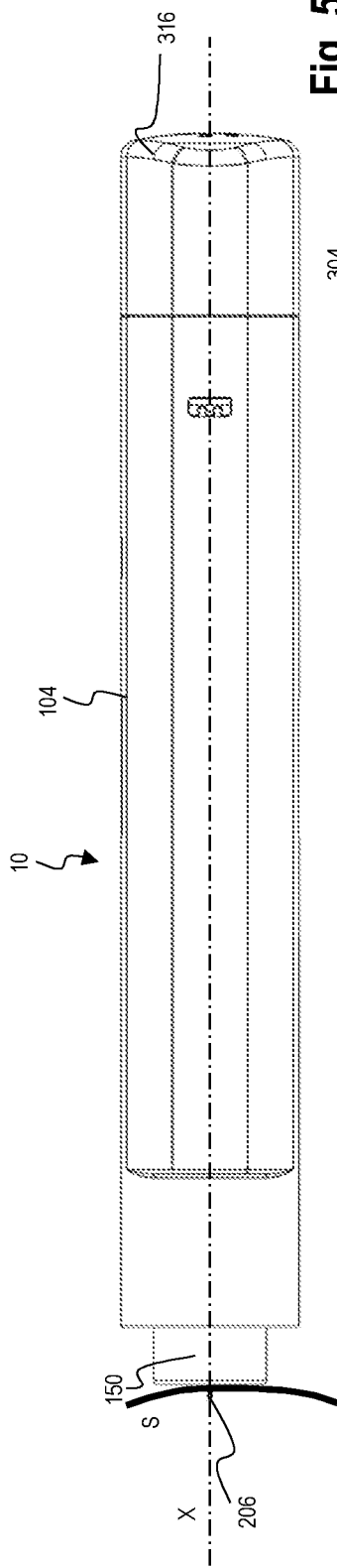
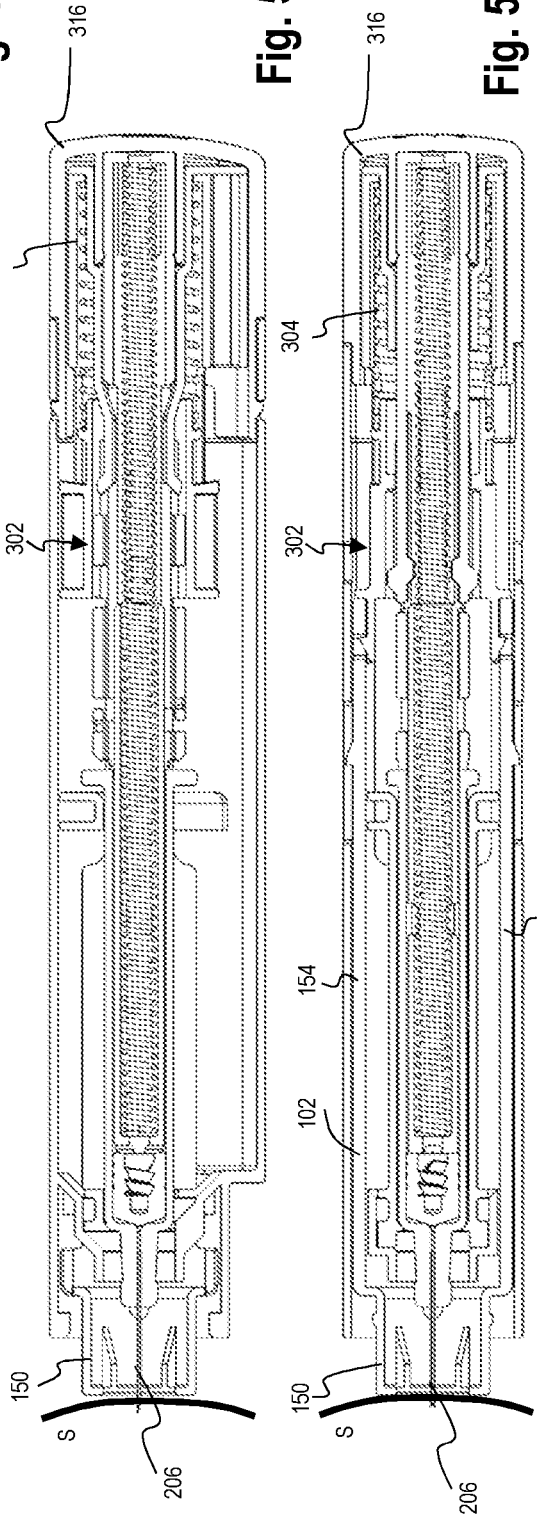
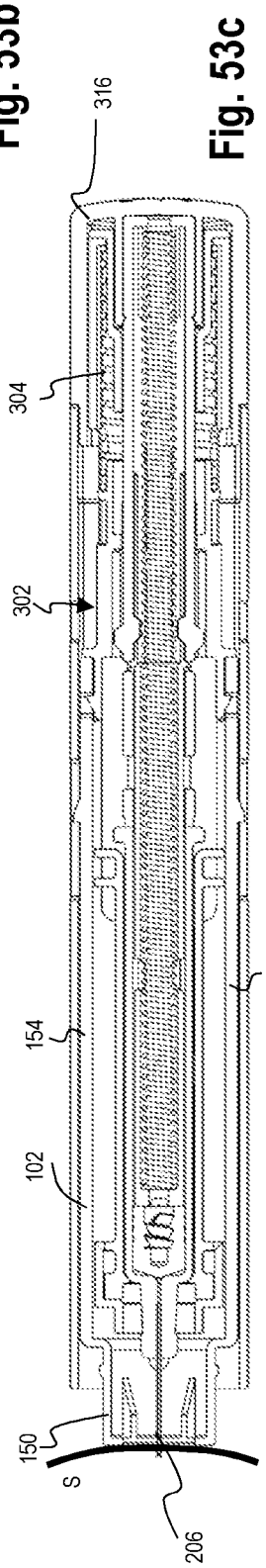
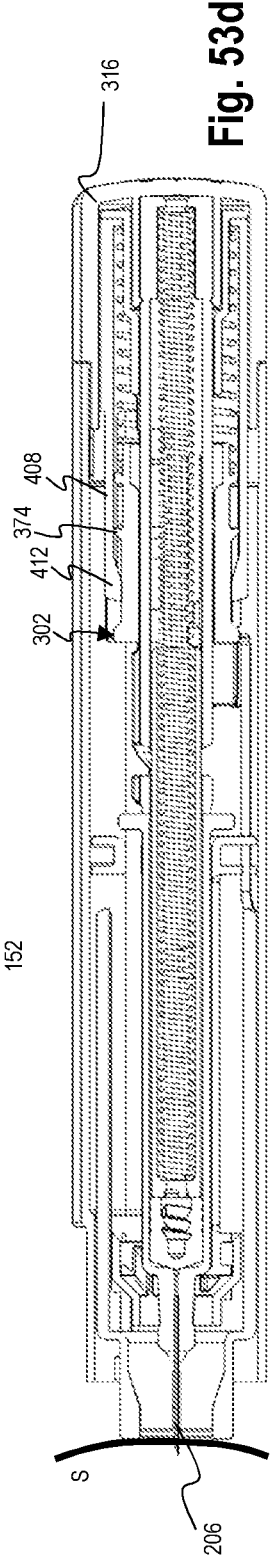

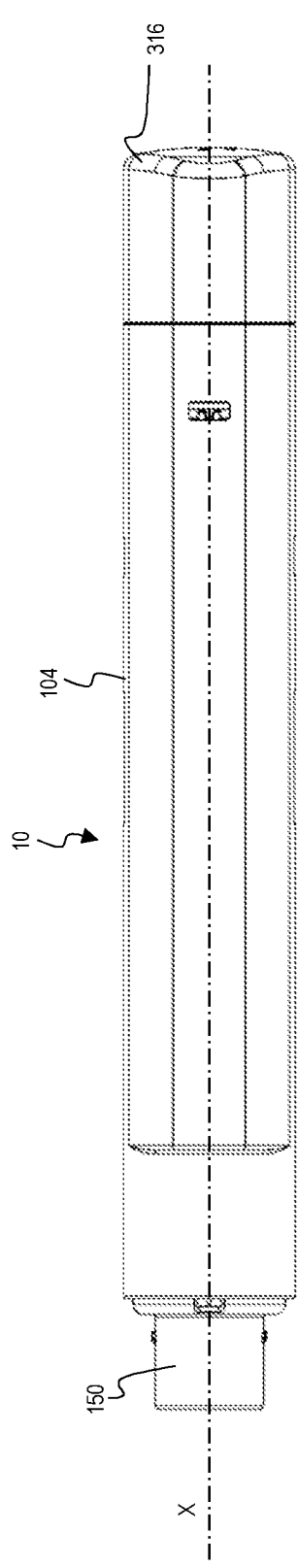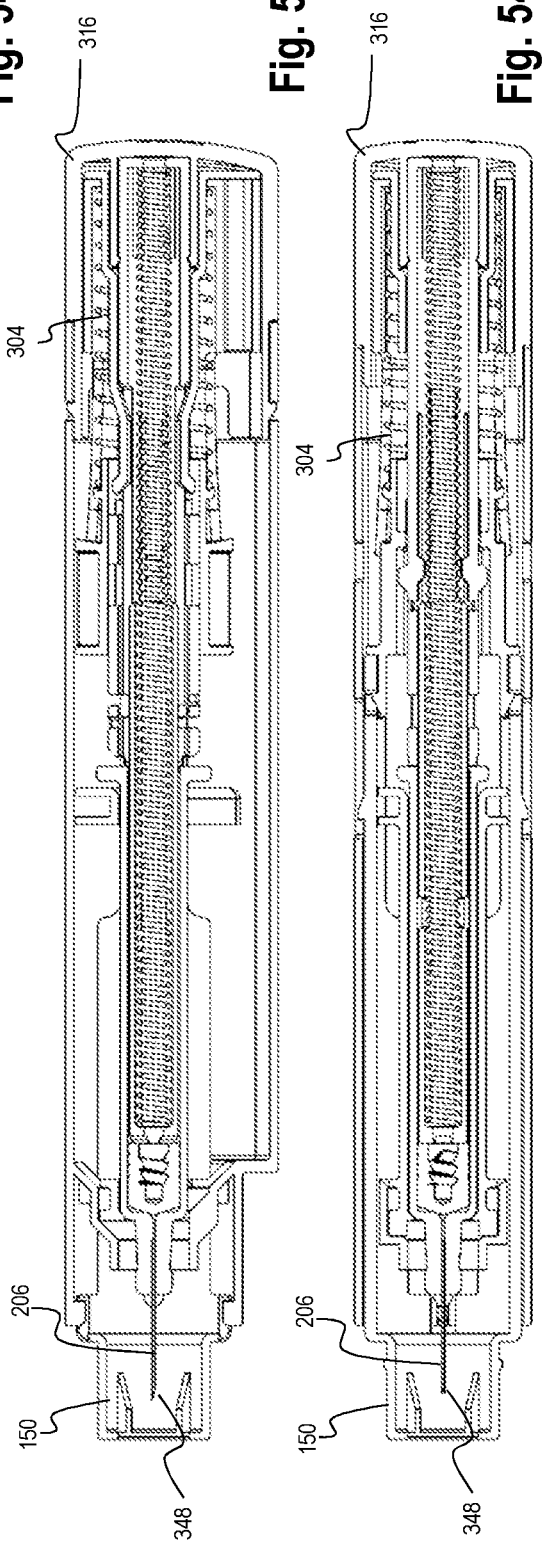

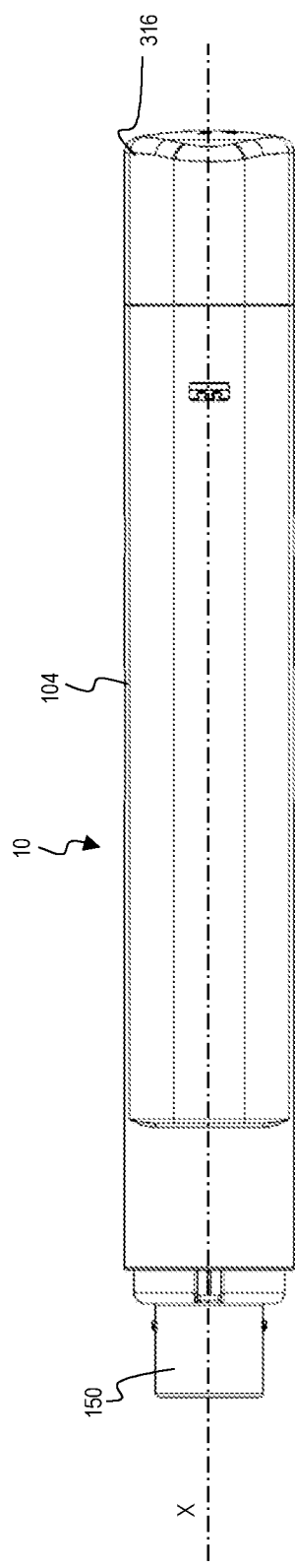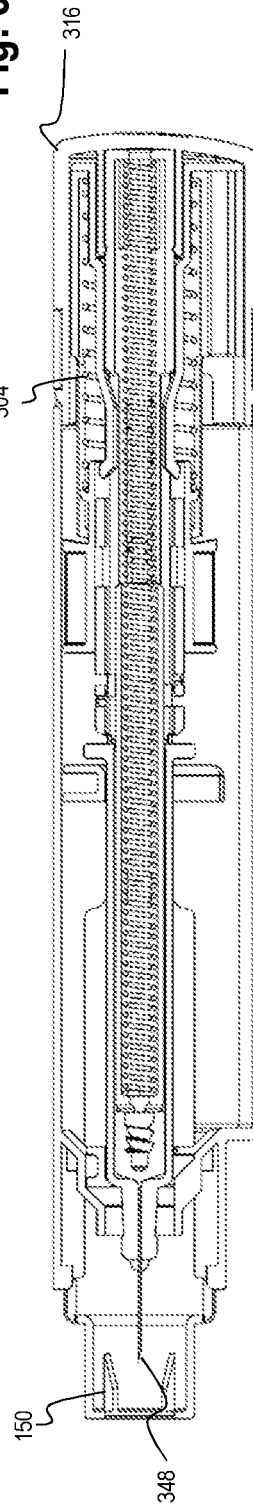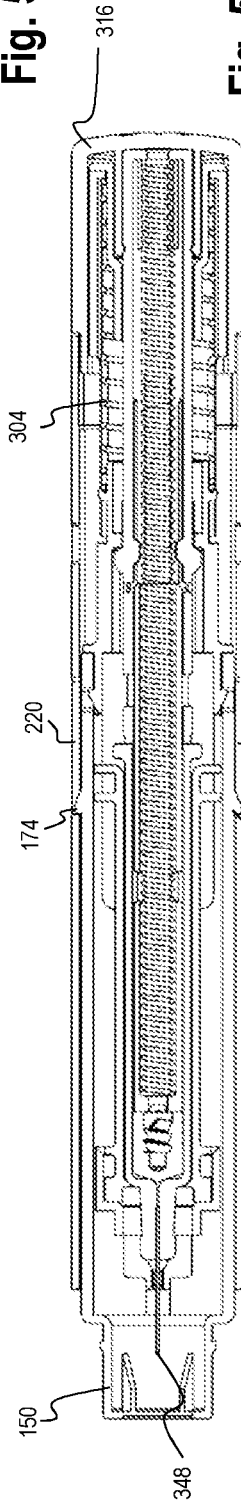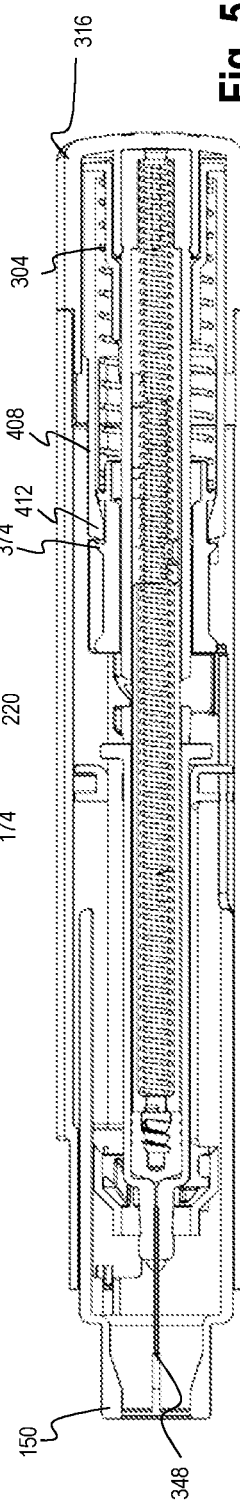

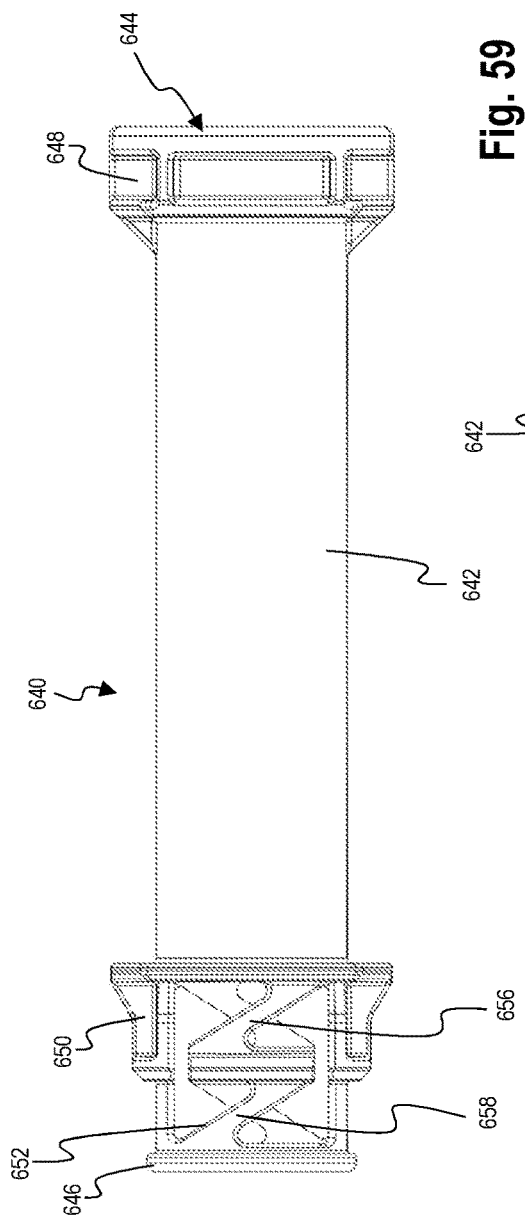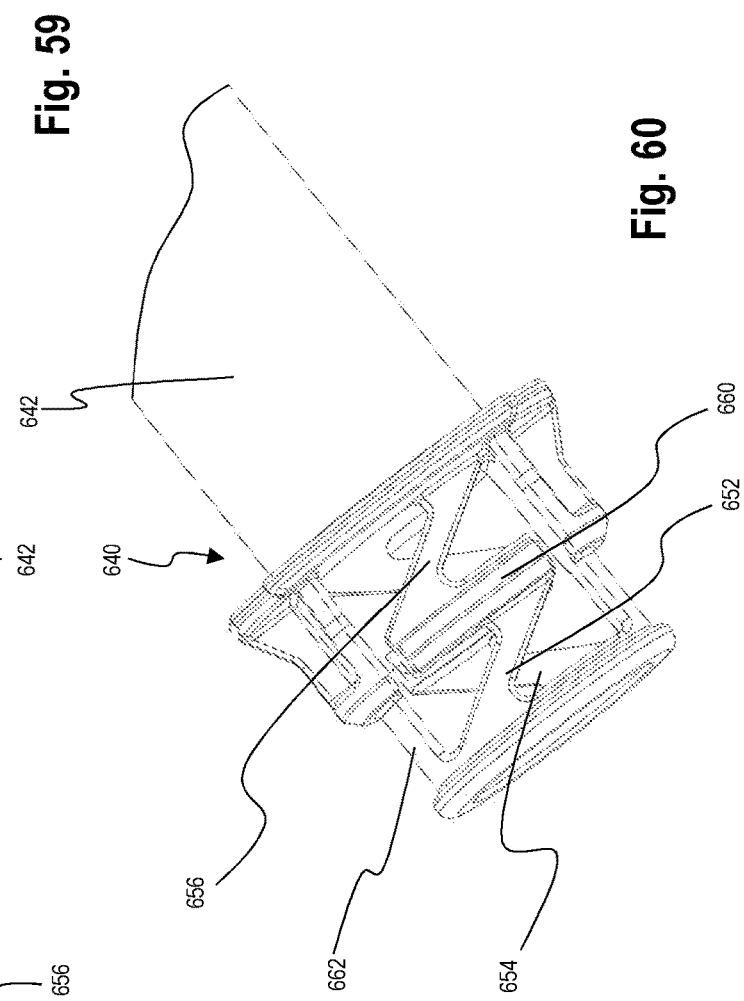

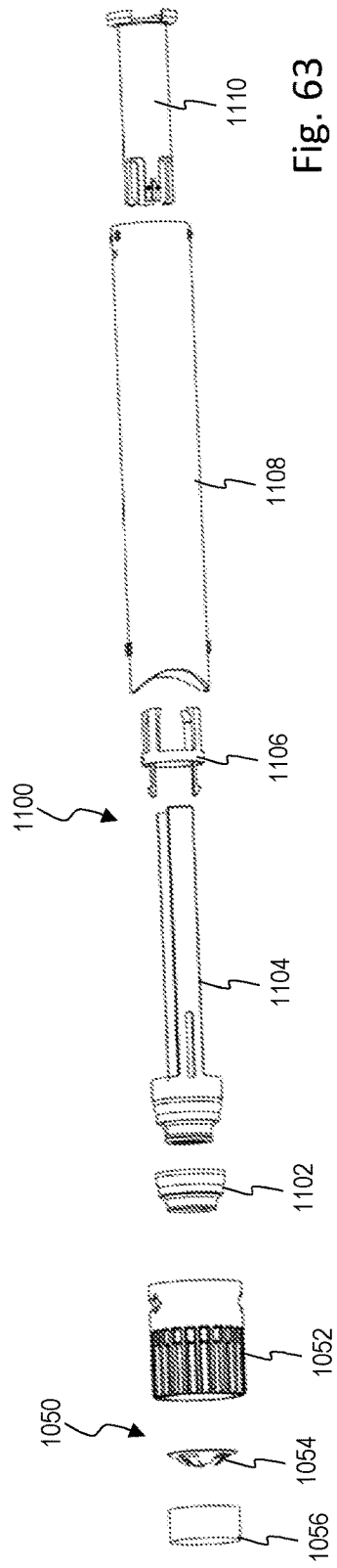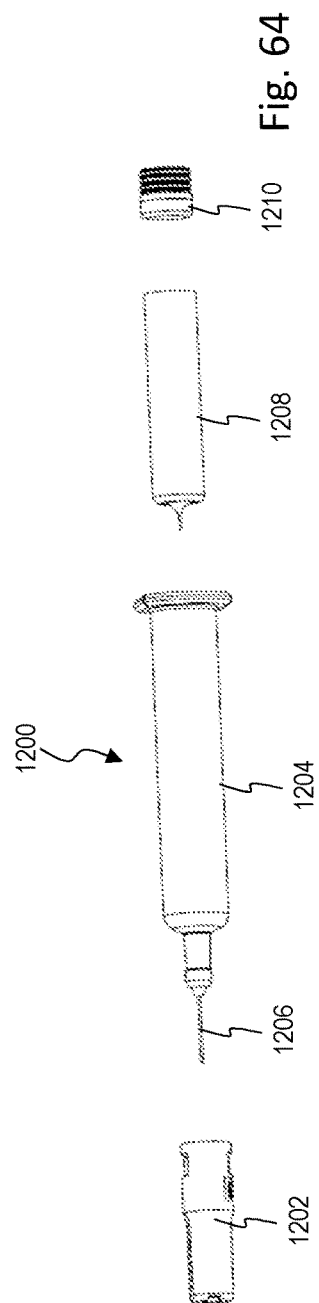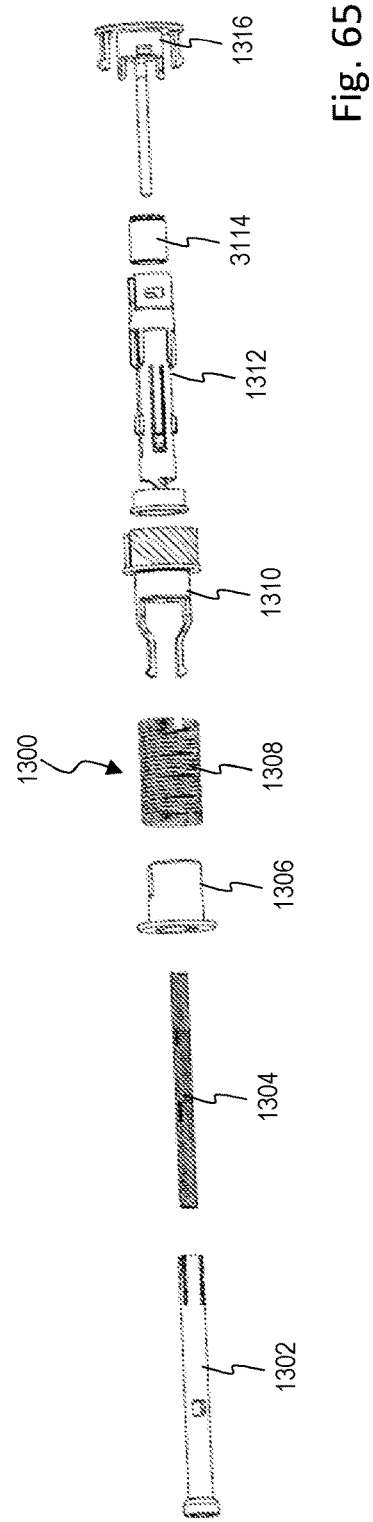

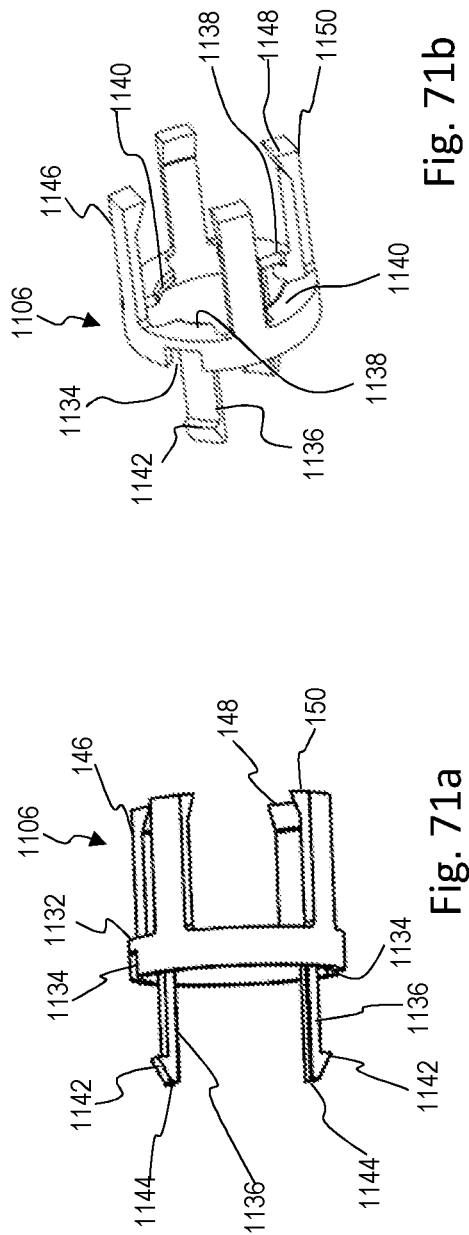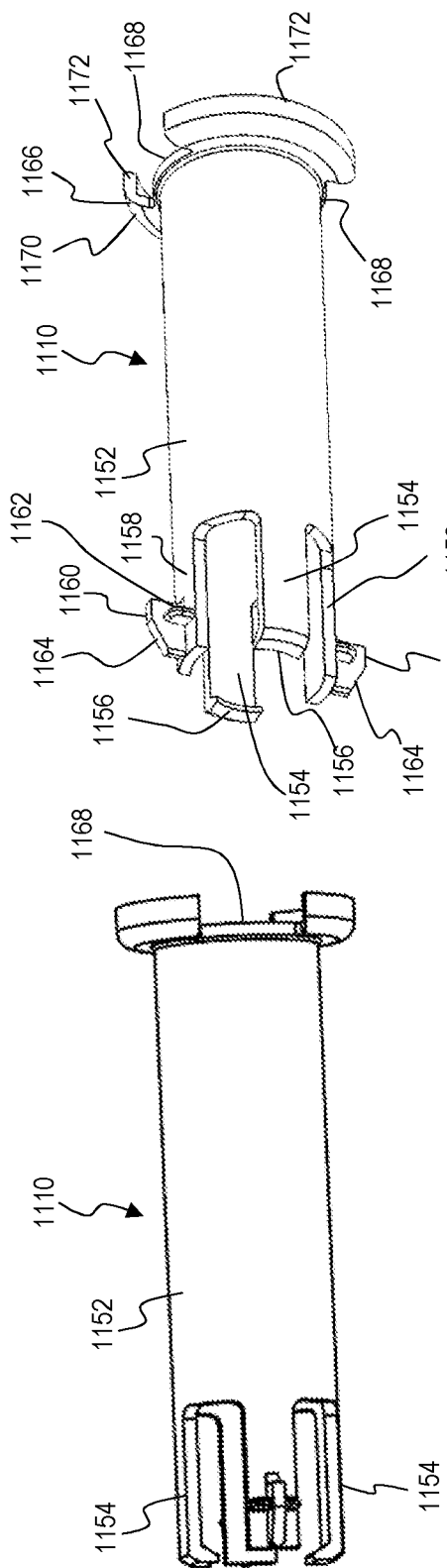

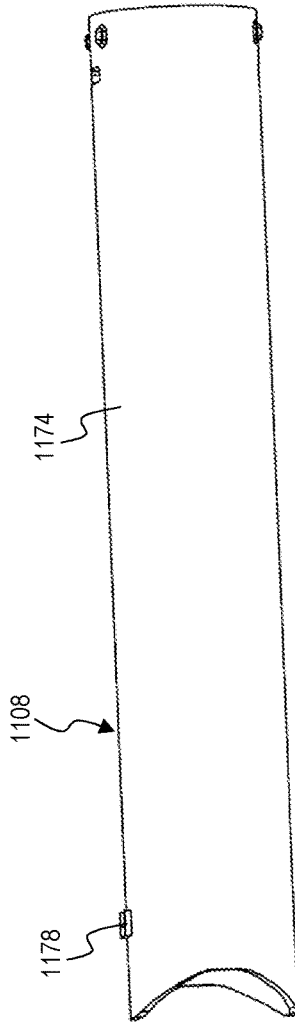
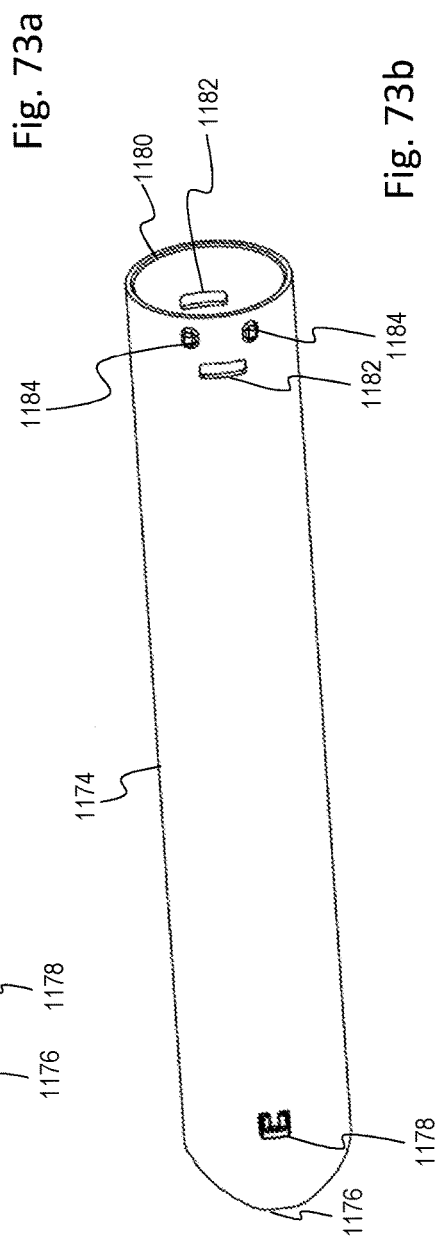
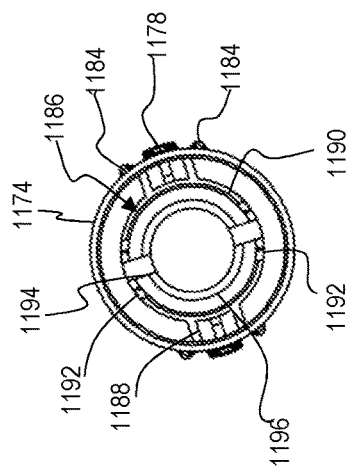
Fig. 73a
Fig. 73b
Fig. 73c

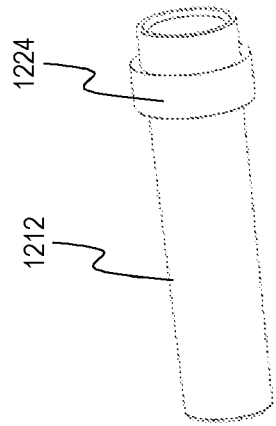
Fig. 75
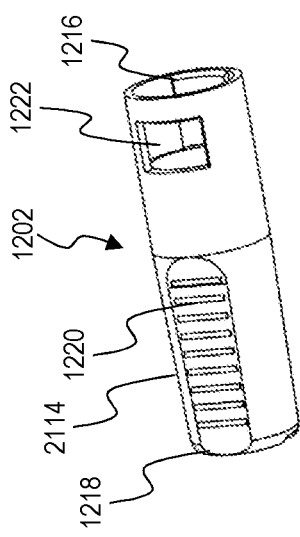
Fig. 74
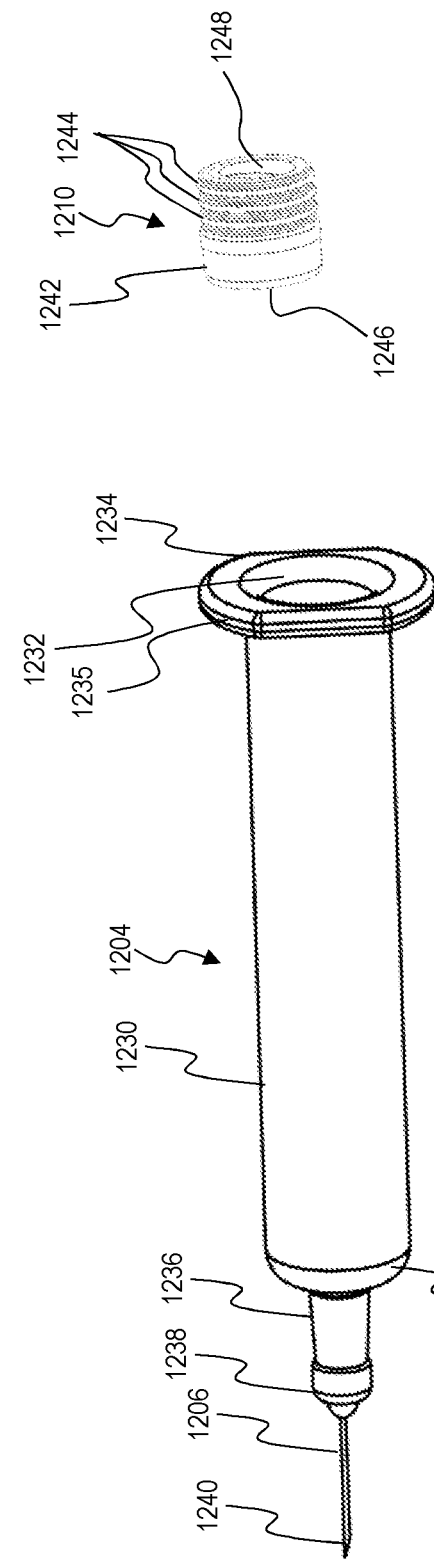
Fig. 77
Fig. 76

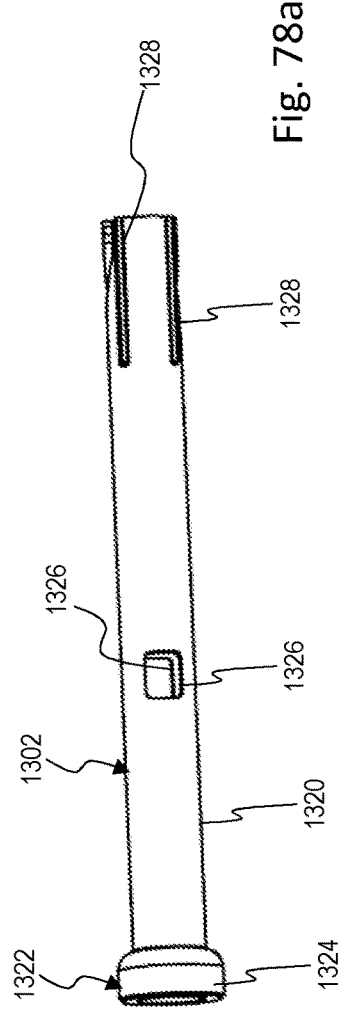
Fig. 78a
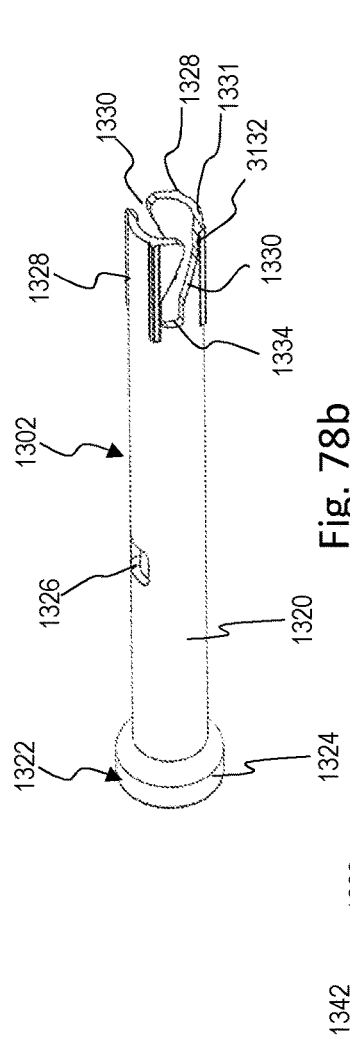
Fig. 78b
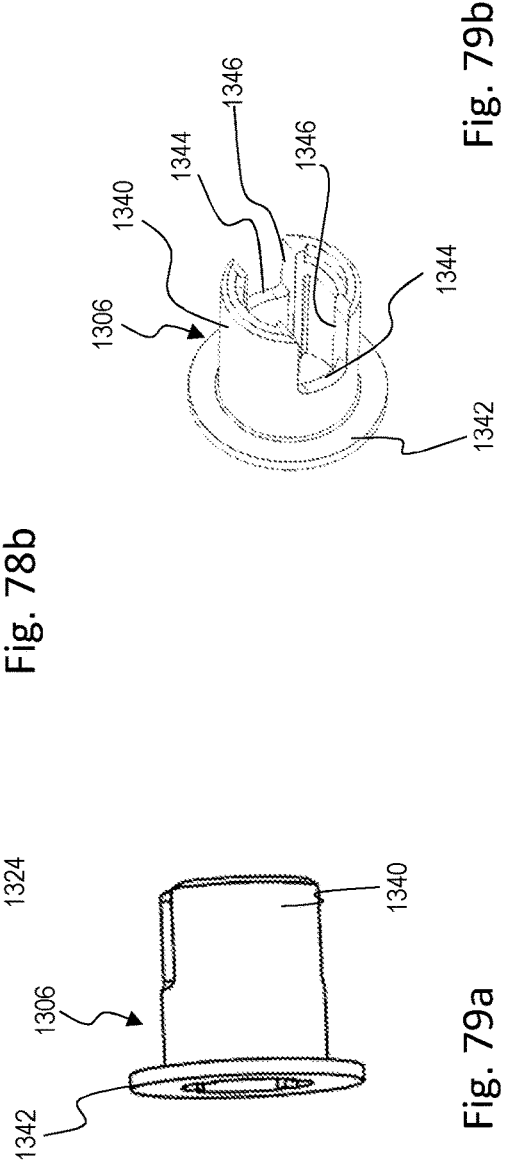
Fig. 79a
Fig. 79b

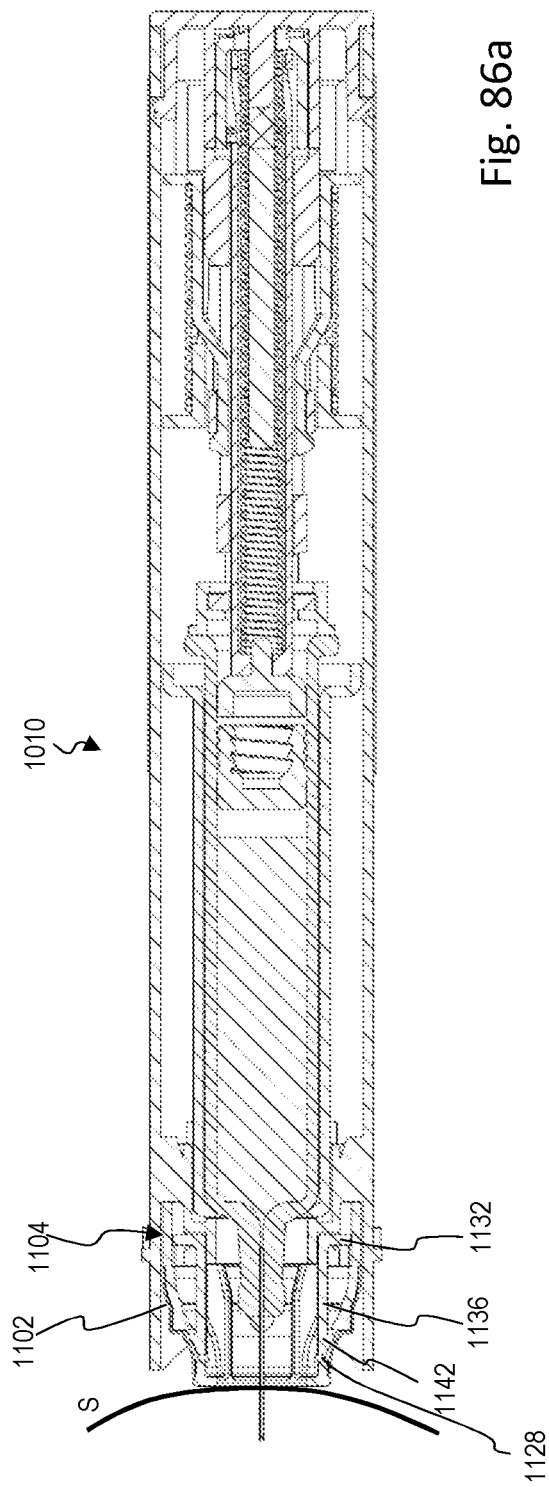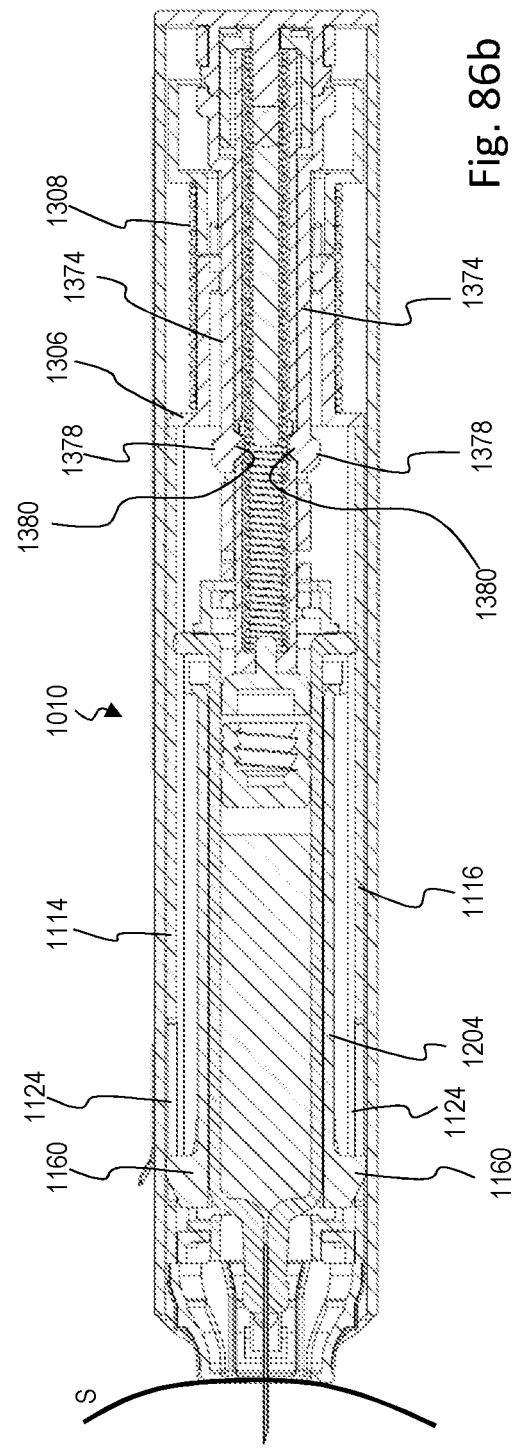

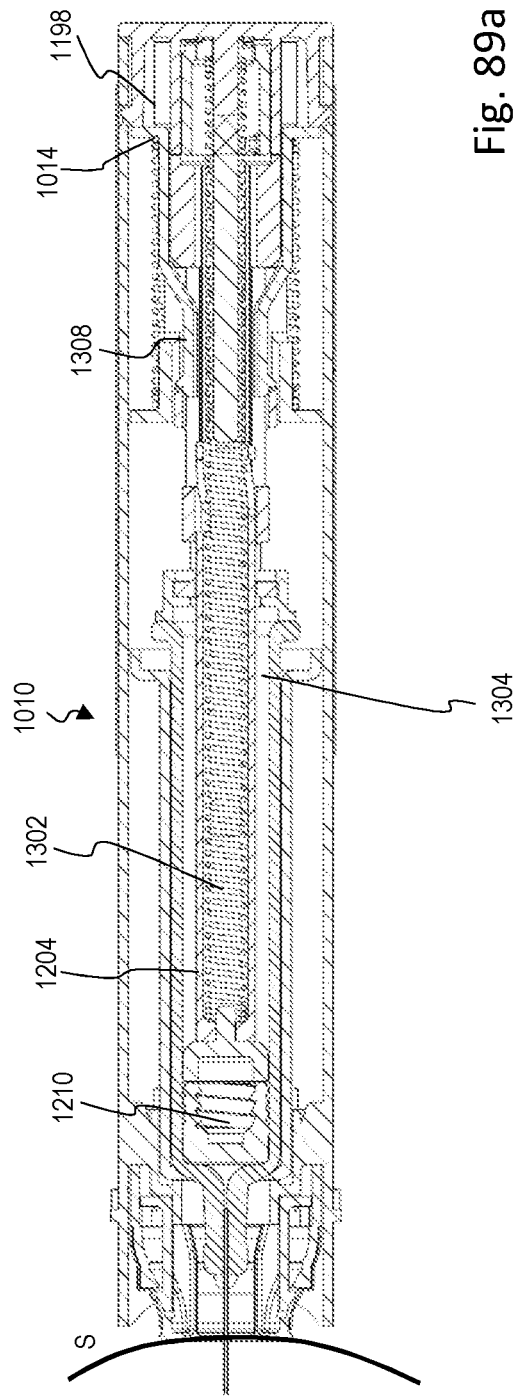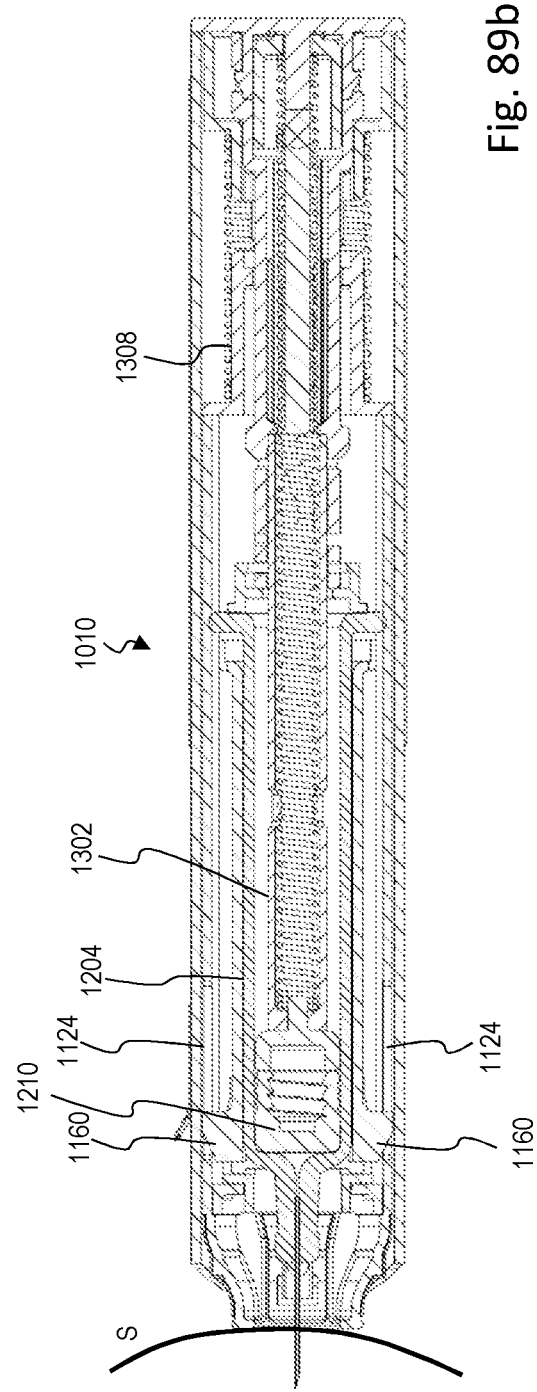

AUTOMATIC DRUG DELIVERY DEVICE

CROSS-REFERENCE TO RELATED APPLICATIONS

This is an application under 35 U.S.C. 371 of PCT Application No. PCT/IB2019/054298, which was filed on May 23, 2019, which claims priority to European Patent Application No. 18174183.6, which was filed on May 24, 2018, and United Kingdom Patent Application No. 1808598.5, which was filed on May 24, 2018, and European Patent Application No. 18174181.0, which was filed on May 24, 2018, and European Patent Application No. 18174190.1, which was filed on May 24, 2018, each of which are herein incorporated by reference in their entireties.

FIELD AND BACKGROUND TO THE INVENTION

The present invention relates to an automatic drug delivery device, in particular an autoinjector, for dispensing a fluid product, in particular a fluid medicament to a patient.

Automatic drug delivery devices formed as autoinjectors are well known in the prior art. There are different types of automatic drug delivery devices available in the market. While current state-of-the-art automatic drug delivery devices provide reliable functioning, they still have a number of drawbacks which are to be overcome.

European patent EP 2 745 866 B1 describes an automatic drug delivery device having a safety shield which acts as a trigger element. The automatic drug delivery device is triggered by pressing the safety shield against an injection site on the patient's skin, where the injection is to be performed. The safety shield is pushed into a longitudinal housing of the automatic drug delivery device and thereby triggers the injection process. When the injection is completed and when the automatic drug delivery device is removed from the injection site, the safety shield is pushed out of the longitudinal housing and blocked by a blocking mechanism in a safety position covering the needle tip. The blocking mechanism is formed within the safety shield and includes flexible arms in plural components. By this structure, the safety shield becomes complicated in geometry and manufacturing. Moreover, the flexible arms of this particular safety shield do not provide sufficient protection against movement of the safety shield into the longitudinal housing after use.

European patent EP 2 903 670 B1 describes an automatic drug delivery device which is activated by rotating an interlock member relative to an activation member. Thereby, rotational relative movements between different components of the actuation mechanism are necessary. Such rotational movements for activating the automatic drug delivery device are often not intuitive which makes the use of such automatic drug delivery devices uncomfortable for the users. A further automatic drug delivery devices having rotational components is known from EP 2 583 711 A1.

Moreover, there are automatic drug delivery devices where the injection process is triggered by pushing a button formed on the distal end or on the circumferential side surface of the device. Such devices include the potential of misuse as the triggering mechanism can be activated although the drug delivery device is not placed correctly on the injection site.

European patent EP 2 978 471 B1 describes an automatic drug delivery device which is also triggered by being pushed with the safety shield against the injection site. The actuation mechanism, however, is complicated in its structure and requires plural parts interacting during relative movements with one another. As a result, the manufacturing and the assembly is complicated.

US 2016/0331905 A1 describes an automatic drug delivery device including an activation mechanism with a ratchet assembly. Different flexible arms interact with a rack having indentations. Due to the plurality of components and moving elements the device is sensible in regard to misuse and erroneous activation. Moreover, the manufacturing and assembly is complicated.

Besides the assembly and functioning of the activation mechanism, a further issue of automatic drug delivery devices is the positioning and holding of prefilled syringe assemblies. Such prefilled syringe assemblies usually include a glass body prefilled with the fluid product to be dispensed. The glass body is to be handled with uttermost care during assembling in order to avoid that the glass body is damaged or otherwise affected. In order to avoid direct handling of the glass body, this prior art document proposes the use of a syringe holder.

Reference is also made to document WO 2016/193374 A1 describing a particular syringe holder having flexible arms which flex out in a pre-assembled state and which relax if an axial force acts on the syringe carrier. An alternative syringe carrier is described in WO 206/193355 A1. This syringe carrier provides a biasing force onto the syringe in axial direction within the housing of the automatic drug delivery device. Another syringe holder providing an axial force on the syringe is known from document WO 2007/083115 A1. Moreover, document WO 2015/015230 A2 describes a syringe holder with a guard element for transmitting axial loads to the syringe support. A further syringe carrier according to the prior art is known from WO/089620 A1, which provides an annular member interconnected by means of two connection arms with a C-shaped proximal receiving member.

A further issue of automatic drug delivery devices is providing feedback signals to the user. Such feedback signals can be audible, visible or tactile signals. Document WO 2016/193343 A1 describes an automatic drug delivery device with an audible indicator including resilient arms, which are deflected radially outwards during use and thereafter relax, whereby an audible signal is generated.

Moreover, another aspect of automatic drug delivery devices is using a removable cap, which while being removed from the housing of the automatic drug delivery device removes a rigid needle shield from the needle of the prefilled syringe assembly. Such removable caps are known from WO 2012/103140 A1. This document describes a relatively complicated structure of a removable cap having plural cap engagement mechanisms.

SUMMARY OF THE INVENTION

End of Dose Features

The automatic drug delivery device may further include a feedback mechanism providing tactile and/or audible and/or visual feedback to the user to indicate the state of operation, wherein the feedback mechanism may include a visual indicator, which appears within the distal end of the housing. The visual indicator may appear in a window which may be provided by an aperture, or may be made of a transparent, or translucent material. Said window and/or distal end of the housing may be transparent or translucent around its entire circumference such that the visual indicator appears in an angular range of up to 360°. The window and or distal end of the housing may be provided by the housing or by a separate part coupled to the housing, e.g. an end cap.

The invention also provides an automatic drug delivery device for dispensing a fluid product, the automatic drug delivery device comprising:
- a longitudinal housing extending along a longitudinal axis and having a proximal end close to a dispensing site, a distal end opposite to the proximal end and a hollow interior;
- a removable cap mountable to the proximal end of the housing;
- a syringe assembly arranged a mounting position inside the housing and having a hollow syringe body and an injection needle coupled to the hollow syringe body including the fluid product;
- a drive mechanism which can be triggered by a trigger element in order to initiate dispensing of the fluid product;
- wherein the drive mechanism is operatively coupled with a safety shield movable within the longitudinal housing,
- wherein the safety shield is biased into a proximal position in which it protrudes out of the proximal end of the longitudinal housing in order to cover a needle tip of the injection needle, and wherein the safety shield is movable into a distal position in which the injection needle is exposed for injection;
- the device further including a feedback mechanism providing a visual feedback to the user indicating an actual state of operation, wherein the feedback mechanism includes a visual indicator which appears in a transparent window on the distal end of the housing.

The the visual indicator may move distally to appear in the transparent window. The visual indicator may be formed by a radial inner indicator component and a radial outer indicator component biased by an indicator spring into an indicator position. The outer indicator may be released into the indication position following the delivery of a predetermined dose of the drug is delivered to a patient. The predetermined dose may be any predetermined dose, but may be a majority of the dose, more than 70% of the dose, more than 90% of the dose, or substantially all of the dose. The predetermined dose may be a sufficiently large proportion of the dose such that the appearance of the visual indicator is indicative of the end of injection. The visual indicator may appear in a transparent window on the distal end of the housing to indicate the end of injection.

The outer indicator component may include a visible surface. The visible surface is the surface that is intended to provide the visual indication. The visible surface may include one or more of colours, shapes, patterns, symbols and images so that the visible surface can be readily distinguished from other surfaces or components of the device. The inner indicator component may interact with the housing or a separate part, e.g. an end cap coupled to the housing, for providing an audible and/or tactile signal.

The device may include a distal endcap which is closed by a distal surface. The distal endcap may be formed from a transparent material to provide the transparent window. The distal surface may be formed from a transparent material.

The safety shield spring may be supported between a shield retention trigger element and a shield retention indicator member. The shield retention trigger member may support a proximal end of the safety shield spring and may apply the biasing force to the distal end of the, or each, longitudinal arm of the safety shield in order to bias it in proximal direction. The shield retention indicator member may support the distal end of the safety shield spring.

The invention also provides an automatic drug delivery device for dispensing a fluid product, the automatic drug delivery device:
- a longitudinal housing extending along a longitudinal axis and having a proximal end close to a dispensing site, a distal end opposite to the proximal end and a hollow interior;
- a removable cap mountable to the proximal end of the housing;
- a syringe assembly arranged a mounting position inside the housing and having a hollow syringe body and an injection needle coupled to the hollow syringe body including the fluid product;
- a drive mechanism which can be triggered by a trigger element in order to initiate dispensing of the fluid product;
- wherein the drive mechanism is operatively coupled with a safety shield movable within the longitudinal housing,
- wherein the safety shield is biased into a proximal position in which it protrudes out of the proximal end of the longitudinal housing in order to cover a needle tip of the injection needle, and wherein the safety shield is movable into a distal position in which the injection needle is exposed for injection;
- wherein the safety shield has at least one longitudinal arm extending in distal direction guided within the longitudinal housing, wherein the safety shield interacts with a safety shield spring biasing the safety shield in proximal direction via the at least one longitudinal arm and wherein the safety shield spring is supported between a shield retention trigger member and a shield retention indicator member, wherein the shield retention trigger member supports a proximal end of the safety shield spring and applies the biasing force to the distal end of the longitudinal arms of the safety shield, and wherein the shield retention indicator member supports the distal end of the safety shield spring.

The drive mechanism may include a plunger biased by a drive spring into proximal direction. The plunger may act on a stopper sealably guided within the syringe body and acting on the fluid product included within the syringe body. The syringe holder may receive axial forces applied by the plunger onto the syringe body and may transmit the forces to the longitudinal housing.

The loaded or energized drive mechanism may include a retainer. The retainer may extend from a distal end of the device to the syringe body. The retainer may comprise at least one flexible arm which is deformable in radial direction. The at least one flexible arm may be used for holding the plunger into a loaded position, in which it is biased in proximal direction.

The retainer may be resiliently deformable to bias the syringe body in the proximal direction. The retainer may comprise a proximal ring-shaped head portion having two opposing projections. The projections may contact the syringe body and may be configured to fit within a syringe body having a larger diameter so that the proximal ring-shaped head portion contacts the syringe body. For example, the projections may contact the syringe body of a 1 ml syringe and may be configured to fit within a 2 ml syringe body which has a larger diameter so that the proximal ring-shaped head portion contacts the 2 ml syringe body.

The at least one flexible arm may further be provided with a chamfered radial outward projection and a chamfered radial inward projection. The chamfered radial inward projection may be provided to interact with a corresponding engagement surface of the plunger in order to hold the plunger in loaded position. The at least one flexible arm may interact by means of the chamfered radial outward projection with an inner circumferential surface of the shield retention trigger element.

The safety shield, when being pushed in distal direction for the purpose of initiating dispensing the fluid product, may move the shield retention trigger element in distal direction, such that it compresses the safety shield spring. After a predetermined stroke of the safety shield, the shield retention trigger element may release the at least one flexible arm for radial outward movement, whereby the plunger is released to move under the biasing force of the drive spring in proximal direction in order to press out and dispense the fluid product from the syringe body through the needle.

The shield retention indicator may include at least one longitudinal holding arm, wherein the shield retention indicator may be held by the at least one holding arm in a non-visible position, in which an indication surface is not visible through the housing (either through a window opening, or through a transparent part of the housing. Thus the shield retention indicator provides the visual indicator. The at least one holding arm may be held by the retainer as long as the plunger has not reached a predetermined dispensing position. The plunger releases the at least one holding arm from the retainer when reaching the predetermined dispensing position. After release of the at least one holding arm the shield retention indicator may be pushed by the safety shield spring to a visible position, in which that indication surface is visible through the housing. A tactile and/or audible signal may be generated, when the shield retention indicator reaches its final visible position.

After the shield retention indicator is released and has moved to a visible position, and the safety shield has been biased to a position in which is covers the needle tip, the shield retention indicator may prevent distal movement of the shield retention trigger member and the shield retention trigger member may prevent distal movement of the safety shield. In this way a locked chain of components can be formed from one end of the device to the other in order to prevent movement of the safety shield in the distal direction.

The shield retention indicator may be formed by a hollow cylindrical body having an annular cylindrical element, which can be extended by an arch-like extension or lobe adapted to the geometry of the housing. It may be received in a slidable but form-fitting manner by the extended portion of the hollow cylindrical body of the longitudinal housing. It has a smooth outer circumferential surface. At its proximal end, the shield retention indicator may be provided with a plurality of, preferably four longitudinal flexible arms, each having a proximal free end. The free ends of the flexible arms can be provided with protrusions extending radially inwardly and reinforced by short longitudinal chamfered ribs. The distal end of the shield retention indicator can be provided with a circular opening.

The arms of the shield retention indicator, as mentioned above are flexible and therefore dampen to a certain, very limited amount, the degree of movement of the safety shield in distal direction after use. However, besides this slight dampening movement, these arms block the safety shield movement in the distal direction and they are configured to buckle radially outwards against the hollow cylindrical body of the longitudinal housing. Thereby, the device provides a very safe lockout after use, preventing easy access to the needle.

The circumferential outer surface of the shield retention indicator may have a signalling colour, i.e. yellow, orange or red, or a signalling pattern which is clearly visible by a user. Thereby, as will be discussed in detail in regard to the operation of the drug delivery device according to the present invention, the user of the autoinjector, i.e. the medical practitioner or the patient, or care giver, can easily recognize when the shield retention indicator is moved into a signalling position in which it is clearly visible through the longitudinal housing from the outside.

The shield retention indicator inner element may be formed by a stepped tubular body having a first hollow cylindrical portion with a smaller diameter and an enlarged second hollow cylindrical portion with a larger diameter. At its proximal end, the shield retention indicator inner element may be provided with two opposing flexible longitudinal arms extending in proximal direction, wherein a first portion runs in longitudinal direction, a second portion is slightly inclined radially inwards, and a third portion extends in longitudinal direction, however, on a radial level which is further radially inwards than the first portion. At its proximal end, each of the arms may have an inclined retaining projection extending radially outwards.

The distal portion of the shield retention indicator inner element may be provided with an end plate having about the same rounded and extended cross-sectional surface as the distal end of the shield retention indicator. The diameter of the outer circumferential surface of the second hollow cylindrical portion can be adapted to be received within the circular opening provided in the distal end of the shield retention indicator.

In order to increase the safety level of the device, the device may further provide a lock ring within the longitudinal housing in an initial position. The lock ring may be locked to the safety shield during operation, wherein the lock ring blocks movement of the safety shield in distal direction, when the safety shield covers the needle after the fluid product is finally dispensed and the automatic drug delivery device has been removed from the injection site.

The lock ring in the initial state may be held by the receiving component, wherein the lock ring engages with the safety shield, after the safety shield has been pushed in distal direction. The lock ring is moved with the safety shield in proximal direction under the spring force of the safety shield spring when removing the automatic drug delivery device from the injecting side. Moreover, the lock ring may block any movement of the safety shield against the receiving component in distal direction when covering the needle.

After release of the plunger from the retainer, proximal movement of the safety shield may be prevented until the plunger reaches a predetermined dispensing position. This predetermined position may be the same as the predetermined position in which the shield retention indicator, but need not be the same. This may allow for accidental removal and then re-insertion of the needle rather than accidental removal resulting the safety shield covering the needle and thus wasting the remainder of the dose. Retaining the safety shield in a retracted state can also make it easier for a user to hold the device against the skin as the biasing force acting on the safety shield is not acting to move the device away from the skin.

The safety shield may be pressed by the end cap via the longitudinal arms against the force of the shield spring in distal direction partially into the housing. The trigger element may act as an intermediate element between the longitudinal arms and the shield spring. The trigger element in the assembled state can be permanently coupled via its projections and any clipping features within, to the distal ends of the arms of the safety shield. The projections can be received within the inner guiding profile at the distal end of the longitudinal arms. Moreover, chamfered projections upon any clip features can engage into through holes or recesses respectively, and thereby prevent, in the assembled state that the arms of the safety shield are separated under an axial force from the trigger element. The chambers of the projections and a guiding profile of the distal end of the arms facilitate the assembling process.

The proximal end of the shield spring may engage against the distal portion of the trigger element and may abut against the circumferential or lateral ribs of the trigger element. The distal end of the shield spring may press via the distal end of the shield retention indicator against the flanged proximal surface of the plate of the shield retention indicator inner element.

The shield retention indicator with its cylindrical body may receive and surround the shield retention indicator inner element as well as the shield spring. The longitudinal arms of the shield retention indicator may extend in a proximal direction through gaps provided between any lateral tabs and/or box structures, each of them may project radially outwards from the trigger element. The longitudinal arms may pass the trigger element, such that the protrusions of the shield retention indicator arms engage the outer circumferential surface of the retainer.

The retainer and connected components may be fixedly held within the distal end cap, for example; by the hollow cylindrical body gripping with an inner circumferential projection into the outer circumferential groove of the retainer in a form-fitting manner. Thereby, the retainer can be fixed within the device against any movement in axial direction as well as against tilting.

The shield retention indicator together with the shield retention indicator inner element may be held in the axial position by means of the shield retention indicator inner arms in spite of the compressed shield spring and the resulting axial drive forces. This can be achieved by the arms reaching through the longitudinal cutouts of the retainer and engaging with their radial retaining projections behind the lateral projections of the retainer bridging the corresponding cutouts of the retainer. Moreover, in this state, the outer circumferential surface of the plunger arranged radially inside the arms may prevent that the arms flex radially inwards and escape from the holding function on the lateral projections.

The plunger can retain the main spring in a compressed state. The proximal end of the compressed main spring may press against the proximal end of the plunger. The proximal end of the plunger can be slidably received within the hollow glass body of the syringe close to the stopper element. The distal end of the main spring may protrude out of the plunger and can be received within the hollow interior of the retainer where it is supported against its distal end. The plunger can be held in its axial position against the drive force of the main spring due to engagement between the flexible arms with the radial inward projections, which engage into the through holes provided in the plunger. As the flexible arms are kept in position by contact between their outwardly radial projections and the inner circumferential surface of the trigger element, the flexible arms cannot flex radially outward in reaction to the drive force of the compressed main spring. Thereby, the plunger is held by the flexible arms of the retainer and their inwardly radial projections.

Cap Features

The present invention relates to an automatic drug delivery device for dispensing a fluid product, in particular a fluid medicament, including:

a longitudinal housing extending along a longitudinal axis and having a proximal end, a distal end opposite to the proximal end and a hollow interior;

a removable cap mountable to the proximal end of the housing;

a syringe assembly arranged in a mounting position inside the housing, the syringe assembly having a hollow body and an injection needle coupled to the hollow syringe body, the syringe body including the fluid product;

a drive mechanism which can be triggered by a trigger element in order to initiate the dispensing of the fluid product;

wherein the loaded drive mechanism is operatively coupled with a safety shield movable within the longitudinal housing, wherein the safety shield is biased into a proximal position in which it protrudes out of the proximal end of the longitudinal housing in order to cover a needle tip of the injection needle, and wherein the safety shield is movable into a distal position in which the injection needle is exposed for injection;

wherein the removable cap is axially retained on the proximal end of the longitudinal housing by engagement of retaining elements between the cap and the longitudinal housing, the retaining elements being disengaged by rotation of the cap relative to the longitudinal housing to allow axial movement of the cap relative to the housing to remove said cap, the axial movement of the cap relative to the housing being supported by the biasing force applied to the safety shield.

The removable cap is axially retained on the proximal end of the longitudinal housing by engagement of retaining elements between the cap and the longitudinal housing. The longitudinal housing may include one retaining structure for engaging at least one engaging structure provided on the removable cap. The engaging structure may engage with the retaining structure to hold the removable cap on the longitudinal housing. Such an arrangement may enhance the security of the fit between the cap and longitudinal housing.

The design of the retaining elements, for example the retaining structure or engaging structure, can be designed to set the cap removal method, or at least provide a preferred removal method. For example, cap removal by pull-off may be blocked, thereby forcing twist-off only. Cap removal by pull-off may be allowed and this would typically be set to an appropriate force. It may be possible for a user to choose between both removal methods. The force required for cap removal by pull-off may be set at a level below that for twist off.

The removable cap may include an end cap body having at least one inner surface, which defines an axially open receiving portion, and having an inner ring, which is connected to the end cap body, wherein the inner surface of the removable end cap and the inner ring form a space for receiving a proximal end of the longitudinal housing. This space between the inner surface and the inner ring may provide a secure way in which the proximal end of the longitudinal housing can be received, which reduces the risk that the cap may be misaligned or accidentally removed or knocked off. The inner ring formation in the cap is potentially advantageous, but may be considered optional in relation to other features provided by the present invention.

In order to implement a suitable retaining function the retaining structure may be formed by at least one projection, for example a U-shaped projection, formed on the outer circumferential surface of the longitudinal housing close to the proximal end and protruding radially outwards, wherein a recess of the U-shaped projection opens in distal direction. The engaging structure may be formed by at least one retaining rib on the radial inner circumferential surface of the removable cap. The retaining action between the removable cap and the longitudinal housing is provided by engagement of the retaining rib into the U-shaped projection formed on the longitudinal housing.

A suitable retaining function may also be implemented by providing that the longitudinal housing and the removable cap include at least one engagement projection and receiving formation for maintaining the removable cap in a locked position relative to the longitudinal housing.

The longitudinal housing may include at least one radial inward engagement projection formed on an inner circumferential surface of the proximal end of the longitudinal housing, and the engagement projection may be adapted to engage with at least one corresponding radial outward projection formed on an outer circumferential surface of the inner ring.

The at least one radial inward engagement projection may be formed by a rib, preferably with a lead-in, e.g. a chamfer or a rounded edge, and the at least one receiving formation may be formed by two opposing chamfered projections and one axial projection. The retaining elements that axially retain the removable cap on the proximal end of the longitudinal housing may comprise inner protrusions formed on the proximal end of the longitudinal housing and projections formed inside the end cap body, the projections inside the cap body comprise a recess within which the inner protrusion is circumferentially restrained by chamfered projections.

The cap the safety shield may, for example during removal of the cap, engage the removable cap with a proximal contact surface formed on or close to the proximal end of the needle shield when the removable cap is mounted to the longitudinal housing. The proximal contact surface can be the proximal front surface of the needle shield or a stepped surface or shoulder provided close to the proximal end of the needle shield. The automatic drug delivery device may further provide that said proximal end of the longitudinal housing engages the removable end cap upon at least one inner surface and/or at the inner ring.

The removable cap may include at least one guiding surface or cam path surface which may be formed as a guiding surface inclined relative to the longitudinal axis for guiding the removable cap in proximal direction along at least a portion of its twisting movement. The at least one guiding surface or cam path surface may be located at the outer circumferential surface of the inner ring. The cam path surface may be adapted or inclined relative to the longitudinal axis for guiding the removable cap in a proximal direction (away from the longitudinal housing) along at least a portion of its rotational or twisting movement. As a further option the guiding surface may be provided as a harmonically closed curved front surface on the proximal end of the removable housing, or formed on the inner circumferential surface of the removable cap, wherein a corresponding guiding projection engaging the guiding surface is formed on the inner circumferential surface of the removable cap or on the front surface of the longitudinal housing.

The safety shield may include a cylindrical and/or ring-shaped hollow body at its proximal end, wherein at least one safety shield projection is provided on the hollow body. The at least one safety shield projection may be adapted to engage with a projection or recess of the removable cap in order to limit movement of the safety shield in the distal direction with respect to the removable cap. Thereby, the safety shield can be prevented from triggering the automatic drug delivery device unintentionally, i.e. such that it starts delivering the drug, when it is subjected to unintentional shock, particularly following freefall and subsequent impact with a hard surface.

The removable cap, when mounted in its retained position to the longitudinal housing, may be secured to the longitudinal housing by a rupturable seal. The rupturable seal, which may be a sticker attached overlapping with the outer circumferential surfaces of the longitudinal housing and with the removable cap, may act as a visible seal showing whether the device has already been used, if ruptured at the interface between the longitudinal housing and the removable cap, or is in its original non-used state, if when intact at said interface. The rupturing of the seal may also require a certain threshold force when twisting the removable cap relative to the housing, which may be sensed by the user.

The invention also provides a method of removing a removable cap from an automatic drug delivery device as described herein, in which the method comprises:
  rotating the removable cap relative to the longitudinal body to disengage retaining elements between the cap and the longitudinal housing;
  providing a removal force to separate the removable cap from the longitudinal body;
  using the biasing force applied to the safety shield to assist with the separation of the removable cap from the longitudinal body.

Rotating the removable cap beyond the position in which the retaining elements between the cap and the longitudinal housing are disengaged may cause a cam path of the removable cap or housing to engage with a portion of the longitudinal housing or removable cap and provide at least some of the removal force to separate the removable cap from the longitudinal body.

Once the retaining elements are disengaged, the removable cap can be pushed in proximal direction by the biasing force acting on the safety shield an audible or tactile feedback may indicates that the engagement between the engaging structure and the retaining structure is released by. Feedback may be provided by a user sensing that an initial resistance to twisting of the cap relative to the housing due to the engagement is overcome in reaction to the application of a sufficiently large twisting force, for example a manual twisting force. Once the engagement is disengaged by applying the sufficiently large threshold twisting force, the removable cap can be further rotated. After a certain level of rotation, the axial force acting on the safety shield supports and pushes the removable cap in proximal direction away from the longitudinal housing. This provides another tactile feedback experienced by the user which may indicate the correct way of handling the device.

When mounted to the proximal end of the housing, the removable cap may contact the safety shield and hold it in a capped position such that, as the cap is removed, the biasing force biasing the safety shield into a proximal position aids in removal of the cap. It should be noted that the removable cap may not be axially retained on the proximal end of the longitudinal housing by engagement of retaining elements between the cap and the longitudinal housing which can be disengaged by rotation of the cap relative to the longitudinal housing to allow axial movement of the cap relative to the housing to remove said cap.

The capped position of the safety shield may be between the proximal position to which the safety shield is biased when unconstrained by the cap and the distal position. In this way the safety shield is held at a position within its expected working range. As noted above, the capped position may be such that further displacement against the biasing force would be required in order to move the safety shield to the distal position.

In the capped position the tip of the injection needle may protrude beyond the safety shield. The cap holds the safety shield in the capped positon and prevents access to the injection needle. As the cap is removed the safety shield moves to its proximal position in which it protrudes out of the proximal end of the longitudinal housing in order to cover a needle tip of the injection needle.

The removable end cap body may be formed to have a cylindrical body integrally formed with an extension, such as an arch-like extension or lobe such that the body has a non-circular sectional form providing an anti-roll shape when the end cap is placed on a flat or slightly inclined surface. The outer surface of the body may be textured or knurled to improve grip. For example, the outer surface of the body may have a number of integrally formed radial gripping recesses or protrusions extending in a longitudinal direction between the proximal and distal ends of the body. The proximal part of the body may be formed by a smooth outer surface. This surface may include arrow-shaped through holes, recesses or projections, or other indicia, which indicate the direction of movement for twisting off and/or pulling the end cap relative to the longitudinal housing.

The interior of the end cap body may include a cylindrical surface forming an axially open receiving portion with a smooth receiving surface. Next to the receiving portion there may be an integrally formed inner ring portion. The ring portion may include a substantially flat distally facing surface. Between the ring portion and the inner circumferential surface of the end cap body, there may be provided one or more open sections and one or more connecting structures connecting both elements. The ring portion may provide on its outer circumferential surface one or more projections extending radially outwards into the open sections. On both sides of the projections, the outer circumferential surface of the ring portion can be provided with inclined lifting formations which have the most distal level close to the projections and which are inclined in a distal direction to meet on an apex.

The outer circumferential surface of the ring portion may have two projections with lead-ins such as a chamfer or radius, which form a receiving space there between. This receiving space may be provided to receive and secure a projection formed on the inner circumferential surface of the longitudinal housing on its proximal end, in a manner which is hidden when viewing and handling the device. This provides the possibility of a hidden coupling between the housing and the removable cap, which cannot be manipulated. Moreover, re-capping of the autoinjector can be obstructed or avoided.

On its radial inner surface, the ring body may include one or more opposite projections, protruding radially inwards. These projections are provided for interacting with and securing corresponding radial outward projections formed on the outer circumferential surface of the proximal end of the safety shield.

The removable end cap body close to its proximal end may be faced with two annular arches arranged in opposite relation and fixed to the inner circumferential surface of the end cap body by means of a connection portion and connecting ribs.

An end cap cover provided for the removable end cap body may have a proximal end cap portion having the same basic surface with a slightly inclined projection as the end cap body. An annular cylindrical body may extend from the proximal surface of the end cap portion. The annular cylindrical body may be provided on its outer circumferential surface with a plurality of longitudinal ribs which protrude over the distal end of the annular cylindrical body. At the free end of these longitudinal ribs, snap-fit projections protruding radially outward can be provided, as far as necessary, which engage into a corresponding (annular) recess within the removable end cap body. The interior of the annular cylindrical body may be provided with chamfered radially extending ribs running into an inner cylindrical body, which is also integrally formed with the distal surface of the end cap portion. The distal front surface of the arrangement formed by the cylindrical body, the projections of the ribs, the radially inner ribs and the inner cylindrical body can form a conical or frustoconical profile.

Gripping Element

The syringe assembly may be provided with a, preferably rigid, needle shield. The needle shield may be coupled to a proximal end of the hollow syringe body. The needle shield may cover the needle together with its, preferably, sharpened needle tip. The inclusion of a needle shield may mean that the needle and the fluid product, e.g. the fluid medicament, are kept clean and sterile Besides the covering function and the feedback function of the removable cap, it may have another purpose for the device. The removable cap may also engage a needle shield. When removing the removable cap, the rigid needle shield may be grabbed and removed together with the cap, such that the user does not have to touch the rigid needle shield directly. As the injection needle and the glass body of the syringe are sensitive components, the rigid needle shield has to be handled with care both during assembly and during removal from the syringe assembly. The removable cap may include a flexible gripping element for engaging the needle shield on its outer profile.

The invention also provides an automatic drug delivery device for dispensing a fluid product, the automatic drug delivery device comprising:
- a longitudinal housing extending along a longitudinal axis and having a proximal end close to a dispensing site, a distal end opposite to the proximal end and a hollow interior;
- a removable cap mountable to the proximal end of the housing;
- a syringe assembly arranged a mounting position inside the housing and having a hollow syringe body and an injection needle coupled with the hollow syringe body including the fluid product;
- a drive mechanism which can be triggered by a trigger element in order to initiate dispensing of the fluid product;
- wherein the drive mechanism is operatively coupled with a safety shield movable within the longitudinal housing;
- wherein the safety shield is biased into a proximal position in which it protrudes out of the proximal end of the longitudinal housing in order to cover a needle tip of the injection needle, and wherein the safety shield is movable into a distal position in which the injection needle is exposed for injection;

wherein the syringe assembly is provided with a needle shield fixed to a proximal end of the hollow syringe body and covering the needle;

wherein the removable cap includes a flexible gripping element for engaging the needle shield on its outer circumferential surface such that removal of the removable cap results in removal of the needle shield, the flexible gripping element having a greater diameter than a proximal end of the safety shield.

Providing a flexible gripping element having a greater diameter than a proximal end of the safety shield allows a lower assembly force to be achieved as longer flexible gripping elements, such as legs or lobes can be utilised. As the gripping element has a greater diameter that than a proximal end of the safety shield the gripping element may not extend into the safety shield and this can provide packaging advantages. In the initial capped state, with the removable cap on the device, the safety shield may be held in a position in which at least a part of the needle shield extends beyond a proximal end of the safety shield as this may facilitate assembly.

The needle shield may engage the hollow conical glass portion by means of an insert. In order to receive the needle and the needle tip in a cushioning and sterile manner, the needle shield may include a soft insert receiving the injection needle. The soft insert safely covers the needle and maintains sterility of the injection needle and the medicament contained within the syringe and the needle. The needle shield may comprise a tubular member that contains the soft insert. The outer surface of the tubular member may include transverse gripping ribs and, or as an alternative, simply a relatively soft outer surface. The gripping ribs, or soft outer surface, may be engaged by the gripping element.

The needle shield may be intended to be gripped on its outer circumferential surface. The needle shield may be provided with at least one gripping structure on its outer circumferential surface profile, for example formed by at least one projection or a recess and engaging with the flexible gripping element. The flexible gripping element is formed as to engage with the outer profile of the needle shield. As an alternative, the gripping can be achieved by engagement of the gripping element with the softer outer surface of an insert of the rigid needle shield.

The flexible gripping element may be fixedly mounted or may be arranged with axial and/or radial clearance within the removable cap. Arranging the flexible gripping element with axial clearance in a floating manner within the removable cap facilitates flexing of the rim during assembly when the gripping element contacts the needle shield. The gripping element may typically be designed to reduce forces in the axial direction onto the rigid needle shield. This is to minimise disruption and ensure that the container closure integrity of the pre filled syringe is maintained. If the gripping element was rigidly held the flexing forces may be increased and axial forces onto the needle shield far higher. Allowing small clearance float and having an edge contact to the gripping element are design features that reduce assembly forces and help to maintain container closure integrity. The clearance may also allow rotation of the gripping element during cap removal. This is also an advantageous feature reducing the potential for coring.

The flexible gripping element may be formed by a flexible washer type component, for example a blade washer, having a mounting section to be mounted within the removable cap. The flexible gripping element, such as a flexible washer type component may include at least one gripping arm or lobe projecting in radial inward direction for engaging the needle shield. The blade washer may have a generally frustoconical shape when installed.

The flexible gripping element may have an outer circumference, for example a circular outer circumference, surrounding a ring-shaped body. The flexible gripping element may include at least two radially inwardly extending lobes or arms integrally formed with the ring-shaped body which may end in a circular radially inner gripping feature.

The flexible gripping element may have a flat or frustoconical shape, wherein, in use, any gripping arms, or lobes, may be adapted to flex in order to provide an axial spring action and/or a gripping force, i.e. a force gripping the outer surface of the rigid needle shield. Such a gripping force may be a force which biases the flexed gripping arms towards a radially central position and thus towards the rigid needle shield.

The external geometry of the gripping element may be of circular or any other geometry to suit assembly loads or packaging space available. There may be two or more extending lobes formed on the radial in a portion of the gripping element and the blade geometry may be of any format to achieve a certain insertion forces during assembling and the ability to hold forces from the rigid needle shield when the removable cap is removed from the longitudinal housing. The gripping element could also have some pre forming. It may be beneficial to form a rib along the outer circumference of the gripping element. This may allow rotation of the gripping element inside the removable cap during cap removal. If the removable cap rotates and the gripping element is only pulled longitudinally a detrimental condition called coring can be eliminated thereby. Unintended coring occurs e.g. in the prior art when the material of the rigid needle shield is rotated around the needle hub of the syringe assembly. It may then be possible for an unintentionally removed plug of rubber to remain inside the needle, which is entirely to be avoided in order to prevent a blockage stopping the device from functioning correctly.

The removable cap may include a proximal end cap cover mountable on or inside the removable cap, wherein the flexible gripping element is arranged in a mounting space between a receiving structure formed on or within the removable cap end the proximal end cap cover.

The rigid needle shield may be engagable by the gripping element during assembling with minimal resistance forces, preferably in the range of 1 N to 50 N, in axial direction applied by the gripping element.

The invention also provides method of assembling an automatic drug delivery device as claimed in any preceding claim, the method comprising:

providing a power-pack subassembly, a syringe assembly, a syringe holder, and a proximal subassembly;

the proximal subassembly including a longitudinal housing extending along a longitudinal axis and having a proximal end close to a dispensing site, a distal end opposite to the proximal end and a hollow interior and a removable cap mounted to the proximal end of the housing wherein the removable cap includes a flexible gripping element and the proximal subassembly further comprises a safety shield, wherein the flexible gripping element has a greater diameter than a proximal end of the safety shield;

the first syringe assembly comprising a hollow syringe body and an injection needle formed with the hollow syringe body including the fluid product, the syringe assembly being provided with a needle shield fixed to a proximal end of the hollow syringe body and covering the needle;

the power-pack subassembly comprising a drive mechanism which can be triggered by a trigger element in order to initiate dispensing of the fluid product;

mounting the syringe assembly in the syringe holder;

inserting the syringe assembly and syringe holder into the proximal subassembly such that the needle shield extends through the flexible gripping element so that the flexible gripping element engages the needle shield on its outer circumferential surface; and mounting the power-pack subassembly to the proximal subassembly such that the drive mechanism is operatively coupled with the safety shield.

The removable cap may include a proximal end cap cover mountable to the removable cap, wherein the flexible gripping element is arranged in a mounting space between a receiving portion inside the removable end cap and the proximal end cap cover.

The gripping element may provide an asymmetric griping force so that the needle shield is biased to a non-aligned position, for example a non-axial alignment within the removable cap. This may be achieved in a variety of ways, for example one or more lobes of the gripping element can have a different shape and/or length than the other lobes such that when engaging the rigid needle shield, there is an asymmetric force load upon the rigid needle shield. This leads to a tilting or turning action such that the rigid needle shield is deflected from its original position. Thereby, recapping, i.e. reattaching the cap onto the housing once it has been removed, can be obstructed or avoided.

Platform Features

The invention also provides automatic drug delivery device for dispensing a fluid product, the automatic drug delivery device:
- a longitudinal housing extending along a longitudinal axis and having a proximal end close to a dispensing site, a distal end opposite to the proximal end and a hollow interior;
- a removable cap mountable to the proximal end of the housing;
- a syringe assembly arranged a mounting position inside the housing and having a hollow syringe body and an injection needle coupled to the hollow syringe body including the fluid product;
- a drive mechanism which can be triggered by a trigger element in order to initiate dispensing of the fluid product;
- wherein the drive mechanism is operatively coupled with a safety shield movable within the longitudinal housing,
- wherein the safety shield is biased into a proximal position in which it protrudes out of the proximal end of the longitudinal housing in order to cover a needle tip of the injection needle, and wherein the safety shield is movable into a distal position in which the injection needle is exposed for injection;
- wherein the longitudinal housing provides an inner receiving component fixed thereto for receiving a syringe holder and providing a predetermined radial and axial position of the syringe holder within the longitudinal housing;
  - wherein the syringe assembly is a first syringe assembly and is received within the longitudinal housing by a first syringe holder, wherein the first syringe holder provides an interface between the longitudinal housing and the syringe assembly; and
  - wherein the longitudinal housing and receiving component is sized and configured to be able to receive a second syringe holder and a second syringe assembly, the second syringe assembly having a different diameter than the first syringe assembly.

This ability for the device to be adapted to a different syringe diameter with the replacement of a single part, in this case the syringe holder, may allow this device to be used as a platform device for a variety of syringe assemblies. The longitudinal housing and receiving component may be sized and configured to be able to receive a second syringe holder and a second syringe assembly, the second syringe assembly having a larger diameter than the first syringe assembly.

The inner receiving component may be fixedly mounted to the inner circumferential surface of the longitudinal housing and may provide a predetermined radial and axial position of the syringe holder within the longitudinal housing. The syringe holder may be received with its proximal end within the receiving component. The receiving component may be integrally formed within the housing. Alternatively, the receiving component may be formed as at least one separate piece fixedly mounted to the inner surface of the longitudinal housing.

Using a syringe holder may allow the pre-manufacture of a subassembly formed by the syringe holder and the syringe assembly. In the subsequent assembly process, this subassembly can be used and mounted within the longitudinal housing. This prevents that the glass body of the syringe assembly is to be directly handled during the assembling process. Instead, the syringe holder already covers, at least partially, the glass body of the syringe assembly and protects it during assembling. Moreover, the syringe holder according to the present invention is provided to receive forces acting on the syringe assembly and to transmit these forces into the housing, wherein stresses acting on the glass body can be avoided or at least substantially reduced.

The receiving component may be formed as an annular member receiving with its inner circumferential surface the proximal end of the syringe holder. The outer circumferential surface of the annular member may be mounted to the inner circumferential surface of the longitudinal housing by means of at least two interconnecting arms. The interconnecting arms between the receiving component and the longitudinal housing can be formed by a solid structure having sufficient wall thickness in order to avoid any unintended movement of the receiving structure relative to the housing under axial loads acting thereon during operation.

The syringe holder may be further provided in a distance from its proximal end, preferably on its distal end, with at least one contact structure for contacting the inner circumferential surface of the longitudinal housing. In this way, the syringe holder can be supported in two distanced axial positions within the longitudinal housing, i.e. on its proximal front end by means of the receiving structure and moreover by the contact structure. Thus, the syringe holder provides a stabile position for the syringe assembly within the longitudinal housing.

The contact structure may be formed by two opposite support arches extending in radial direction from the distal end of the syringe holder. A recess between the two arches can be used to guide further functional components of the trigger mechanism or the like, e.g. the longitudinal arms of the safety shield as discussed herein. The two longitudinal arms may be guided through recesses formed in the syringe holder between the support arches.

As noted above, the drive mechanism may include a plunger which may be biased by a drive spring into proximal direction. The plunger may act on a stopper sealably guided within the syringe body and acting on the fluid product included within the syringe body. The syringe holder may receive axial forces applied by the plunger onto the syringe body and may transmit the forces to the longitudinal housing.

The syringe holder may resiliently engage the syringe glass body close to its proximal end by means of at least two resilient arms. In particular, the syringe holder may be adapted to grip around a proximal front shoulder of the glass body of the syringe such that the resilient arms slightly flex out during assembly and engage with the glass syringe body on a radial step surface formed radially around a needle hub of the syringe glass body.

In order to provide the possibility of using one and the same device according to the present invention for different prefilled syringes having different fluid product volumes, i.e. in order to provide a platform device usable for different prefilled syringe sizes, according to another aspect of the present invention the syringe holder may be provided in different sizes adaptable to different sizes of the syringe body. Thereby, the syringe holder can be provided in different configurations in order to receive different syringe sizes and accommodate these different syringe sizes within the device according to the present invention without the need of modifying longitudinal housing or any other component thereof.

The invention also relates to a syringe holder for an automatic drug delivery device as described herein, wherein the syringe holder is adapted for receiving the syringe assembly within the longitudinal housing, wherein the syringe holder provides an interface between the longitudinal housing and the syringe assembly, wherein the longitudinal housing provides an inner receiving component fixedly mounted to the inner circumferential surface of the longitudinal housing providing a predetermined radial and axial position of the syringe holder within the longitudinal housing, wherein the syringe holder is received with its proximal end within the receiving component.

The syringe holder may receive the syringe in a radial or in an axial direction. The syringe holder may form part of the syringe assembly and may act as an interface, spacer, or adapter, allowing various combinations of syringe bodies and injection needles to be used with a particular automatic drug delivery device. In particular, the syringe holder may allow a device designed to accept a syringe body having a first external dimension (with or without a syringe holder), to accept a syringe body having a second external dimension, which is smaller than the first external dimension, by changing/adding only one component. The external dimension of the syringe body may be diameter, or may be length.

The syringe holder may be arranged to provide contact, interface, or mounting, points with which the syringe assembly interacts with other parts of the automatic drug delivery device. The contact, interface, or mounting, points provided by the syringe holder may replicate contact, interface, or mounting, points of another syringe assembly, for example one which does not require a syringe holder, or one which includes a different syringe holder. In this way the automatic drug delivery device may be designed to receive, and interact with, a syringe assembly of a first size and shape, perhaps without a syringe holder, and still be able to receive, and interact with, a different syringe assembly through use of an appropriate syringe holder.

The contact, interface, or mounting, points may be provided on any suitable part of the syringe holder. The contact, interface, or mounting, points may be provided on one or more surfaces of one or more flanges, ridges or other extensions from a body of the syringe holder. There may be at least two contact, interface, or mounting, points, and these may be longitudinally separated along a length of the syringe holder. One contact, interface, or mounting, point may be located at one end of the syringe holder and one at an opposite end of the syringe holder. As an example, the syringe holder may comprise a first interface that substantially replicates a flange of a syringe.

The ability of the automatic drug delivery to receive and interact with a variety of syringe assemblies is significant as it allows a single device design to be used to administer medicaments from different syringe bodies and potentially in different volumes. A plurality of syringe holders may be provided for the device so that an appropriate syringe holder can be selected for use with a particular syringe body and needle combination.

The invention therefore further provides automatic drug delivery device for dispensing a fluid product, in particular a fluid medicament, including:
  a longitudinal housing extending along a longitudinal axis and having a proximal end close to the dispensing site, a distal end opposite to the proximal end and a hollow interior;
  a removable cap mountable to the proximal end of the housing;
  a syringe assembly arranged a mounting position inside the housing, the syringe assembly having a hollow syringe body and an injection needle coupled with the hollow syringe body, the hollow syringe body containing the fluid product;
  a drive mechanism which can be triggered by a trigger element in order to initiate the dispensing of the fluid product;
  wherein the loaded drive mechanism is operatively coupled with a safety shield movable within the longitudinal housing,
  wherein the safety shield is biased into a proximal position in which it protrudes out of the proximal end of the longitudinal housing in order to cover a needle tip of the injection needle, and wherein the safety shield is movable into a distal position in which the injection needle is exposed for injection;
  wherein the syringe assembly further comprises a syringe holder, the syringe holder supporting the syringe body within the housing.

The invention further provides a method of manufacturing an automatic drug delivery device comprising the steps of:
  providing a housing, a drive mechanism and a safety shield;
  providing a hollow syringe body and an injection needle coupled with the hollow syringe body, the hollow syringe body containing a fluid product;
  determining whether a syringe holder is required to support the hollow syringe body and injection needle combination;
  if necessary, selecting an appropriate syringe holder and creating a syringe assembly comprising the syringe holder, hollow syringe body and injection needle; and
  installing the drive mechanism, safety shield and syringe assembly into the housing to create the automatic drug delivery device.

A plurality of syringe holders may be provided. Syringe holders may be configured in different geometries and adapted to receive different syringes with different volumes of medicament, wherein, independent from the received syringe, the respective syringe holder is adapted to fit into the same housing of said automatic drug delivery device. In other words, a syringe holder according to the invention can be provided in different geometries and with different structures such that it receives different syringe sizes (e.g. 1 ml and 2 ml) in a way that is easy and consistent to assemble and that holds the syringe safely within the housing. In particular, the different syringe holder geometries are adapted to fit in one and the same housing without further modification. This allows for providing a platform system, i.e. drug delivery device which has the same outer dimensions, and assembly requirements for different doses and medicaments. It may be necessary to replace also the plunger or provide an adapting member at the proximal plunger end, e.g. adapted to the different inner diameter of the syringe and/or the syringe stopper.

The syringe holder may include at least one flexible portion allowing for elastic deformation in circumferential or radial direction. This may allow the syringe holder to receive and resiliently retain a syringe body and/or injection needle within the syringe holder.

The syringe holder may include a longitudinal body, which at its proximal end and or at its distal end is formed with a rigid and substantially non-elastic U-shaped element, such that a prefilled syringe can be introduced into the syringe holder from radial direction transverse to the axial direction.

The syringe holder may be formed by two longitudinal shells, connected by at least one flexible V-shaped portion, which provides flexibility in a circumferential direction to the syringe holder and allows that the shells move elastically apart when introducing a syringe.

The syringe holder may include a radial inner projection for supporting the syringe body in the axial direction, in particular in proximal axial direction. The radial inner projection of the syringe holder may support a proximal shoulder of the syringe body.

The syringe assembly may include a, possibly rigid, needle shield fixed to a proximal end of the hollow syringe body and covering the needle. The syringe holder may receive the syringe assembly in a radial direction such that the radial inner projection is located between the syringe body and the needle shield. The radial inner projection may have a smaller diameter then the rigid needle shield.

The syringe holder may be provided with one, two or more flexible zones or portions, in particular z-shaped flexible portions, which can flex in a radial and/or circumferential direction. The flexible portions/zones can support the syringe in axial direction once plugged-in from distal direction and received therein whilst allowing some degree of axial movement e.g. for absorption of impact energy and assembly misalignment.

The drive mechanism may retain the plunger in an initial position through the engagement of a radial inward projection with a slot in the plunger. The plunger may be provided with a plurality of retaining slots adapted to different syringe sizes or variant fills. The plurality of retaining slots may include slots at different axial positions. One or more of the retaining slots may engage with the drive mechanism and thereby determine the initial position of the plunger relative to a moveable stopper, or other feature, of the syringe assembly. By providing slots having different longitudinal positions it allows the plunger to engage with the drive mechanism at different longitudinal positions during manufacture. The plunger may comprise retaining slots that are longitudinally and circumferentially offset. This may facilitate manufacture as the slots may only engage with the drive mechanism in a particular rotational orientation. By circumferentially offsetting the slots the plunger can be aligned with the drive mechanism for assembly, rotated into the correct orientation so that the longitudinal slots at the desired position align with the drive mechanism engagement parts. The plunger can then be assembled by a linear motion into the drive mechanism so that the desired slots engage with the drive mechanism. If the slots were not circumferentially offset the assembly motion may be move complex with linear and rotation required and this may result in assembly errors.

The plunger may include an alignment marker to facilitate rotational alignment. The alignment marker may be any suitable marker, for example a visible mark, for example one that may be printed or etched one the plunger, of the marker may be a physical marker, for example a projection or groove which can be engaged by assembly apparatus. The alignment marker may be an alignment slot in an end of the plunger. The alignment slot may extend entirely across a diameter of the end of a substantially cylindrical plunger. The alignment slot may be in a stopper engaging end, or plunger head, of the plunger to facilitate assembly.

The plunger head of the plunger rod may include an adapter to increase the diameter of the plunger head for some stopper diameters. The plunger adapter may be integrally molded with the plunger. As with the syringe holders the various options can mean that a plurality of plungers are available for assembly into a particular device.

This means that the method of manufacturing an automatic drug delivery device mentioned above may further comprise the step of determining which plunger head size is required for a particular syringe body and injection needle combination and selecting an appropriate plunger for assembly into the device. The selection may not be purely based on head size, so the manufacturing method may comprise the step of:

determining which of a plurality of plungers is required for use with selected syringe assembly;

assembling the selected plunger into the device.

If the plunger has longitudinally offset slots for engaging with the drive mechanism the method of manufacturing an automatic drug delivery device mentioned above may further comprise the step of determining which of the longitudinal slots should engage with the drive mechanism a particular syringe assembly and engaging an appropriate longitudinal slot with the drive mechanism during assembly. If the longitudinal slots are circumferentially offset, the method may further include the step of rotating the plunger to a predetermined rotation relative to the drive mechanism prior to assembly.

As noted above, the provision of a plurality of plungers and syringe holders for a particular device design can provide a platform device which can be used to delivery medicament from a plurality of syringe bodies having different sizes and fill volumes.

The invention therefore provides a kit of parts for assembling an automatic drug delivery device for delivering medicament from a hollow syringe body having an injection needle coupled thereto, the hollow syringe body containing a fluid product, the kit comprising a standard housing, a standard drive mechanism and a standard safety shield, a plurality of syringe holders and/or a plurality or plungers. This means that a combination of parts can be assembled together to create an automatic drug delivery device that is appropriate for the particular hollow syringe body and injection needle. This 'platform' type architecture allows the device to be adapted for use with syringe body/needle combinations having different sizes/shapes/fill volumes by changing only one or two parts.

The invention also provides a kit of parts for assembling an automatic drug delivery device as described herein, the kit comprising a power-pack subassembly, a first syringe assembly, a second syringe assembly, and a proximal subassembly;

the proximal subassembly including a longitudinal housing extending along a longitudinal axis and having a proximal end close to a dispensing site, a distal end opposite to the proximal end and a hollow interior and a removable cap mounted to the proximal end of the housing;

the first syringe assembly comprising a hollow syringe body and an injection needle formed with the hollow syringe body including the fluid product;

the second syringe assembly comprising a hollow syringe body having a diameter larger than the diameter of the syringe body of the first syringe assembly, and an injection needle coupled to the hollow syringe body including the fluid product;

the power-pack subassembly comprising a drive mechanism which can be triggered by a trigger element in order to initiate dispensing of the fluid product;

a first syringe holder to provide an interface between the longitudinal housing and the first syringe assembly; and a second syringe holder to provide an interface between the longitudinal housing and the second syringe assembly; wherein the assembled automatic drug delivery device comprises the power-pack subassembly and the proximal subassembly and either the first syringe assembly and the first syringe holder, or the second syringe assembly and the second syringe holder.

The invention also provides a method for assembling an automatic drug delivery device using a kit of parts as described above, in which the method comprises:

selecting either the first syringe assembly and the first syringe holder, or the second syringe assembly and the second syringe holder;

mounting the selected syringe assembly in the selected syringe holder;

placing the syringe and syringe holder into the proximal subassembly; and assembling the power pack subassembly onto the proximal subassembly.

As discussed herein, the syringe holder has the purpose to receive and hold a prefilled syringe within the housing. It is adapted to receive different kinds of syringes with different volumes of medicament without the need of changing the other components of the subassembly. Therefore, different syringe holders are to be provided in adaptation to the different kinds/volumes of syringes.

The syringe holder may comprise a longitudinal body. At its proximal end, the syringe holder may be formed with a substantially rigid and non-elastic U-shaped element. The U-shaped element may be open in one radial direction. This rigid U-shaped element at the proximal end may be reinforced by parallel surrounding ribs. At the proximal front surface, the U-shaped element may be provided with transverse ribs or projections. At its distal end, the syringe holder may be provided with a substantially rigid and non-elastic similar U-shaped element. The distal U-shaped element may be reinforced with surrounding ribs. The surrounding ribs may be provided with cutouts, facing radially outwards on opposite positions. The rigid U-shaped elements may be connected by two, possibly substantially rigid and longitudinal, connecting arms. Each of the connecting arms may extend in a linear manner. Each of the arms may include a projection projecting radially inwards to releasably retain a syringe in the syringe holder, the arms being deformable to allow a syringe body to pass between the projections. The inner surface of the projections may be profiled such that a glass body of the syringe can be arranged and held therein.

When placed within the longitudinal housing, the syringe holder holding a prefilled syringe assembly, may be positioned such that any projections engage into matching cutouts of the double-ring structure. The syringe holder may be positioned by the ring structure or double-ring structure within the longitudinal housing in an appropriate axial and rotational position around the longitudinal axis.

According to some examples of the syringe holder, the syringe holder can be formed by two or more longitudinal shells, with a longitudinal slit between them. The shells can be connected by flexible V-shaped portions, on the distal and the proximal regions respectively, which provide flexibility in circumferential direction to the syringe holder and thereby allow that the shells move elastically apart when introducing a syringe. The syringe holder may further comprise at its distal end and close to its proximal end radially outward projecting structures for fixing the syringe holder within a housing of an autoinjector.

An inner radial projection can be formed within both shells, for supporting the syringe in axial direction once inserted from the distal direction and received within the syringe holder.

Alternatively, the syringe holder may have a hollow cylindrical receiving tube with a distal end and a proximal end. Similar to the other examples described herein, this syringe holder may also include radial outwardly projecting structures in order to hold the syringe holder within a housing of an autoinjector.

Close to its proximal end, the syringe holder can be provided with one or more double-z portions, which include inclined flexible arms interconnected by a circumferential rib. At its inner circumferential surface, the syringe holder includes a radially inward projection, which can be formed circumferentially within both flexible double-z portions for supporting the syringe in axial direction once inserted from the distal direction and received therein. In this syringe holder example, the syringe is pushed-in from its distal end with minor radial play within the hollow cylindrical receiving tube. For gripping the proximal front end of the glass body of the syringe, due to the elastic flexibility of the two double-z portions, the arms slightly flex-out such that the circumferential ribs move radially outwards.

Examples for the syringe holder described herein have a circumferentially closed structure with features providing some flexibility in radial or circumferential direction. Thereby, it is possible to provide an easy assembling of the prefilled syringe with the syringe holder. The syringe is held simply by flexing elements which deform radially outwards during assembly. Thereby, tolerance variations of the syringe assembly can be compensated both radially as well as axially. Nevertheless, the syringe holder has a robust structure by virtue of the rigid shells or the cylindrical receiving tube.

The plunger may be formed by a longitudinal cylindrical hollow element which has at its proximal end a plunger head. The plunger head may be provided with a front surface and a transverse slot. The front surface may include a small cylindrical through hole. The front surface with the optional transverse slot and the cylindrical through hole can be coupled with or formed with a larger diameter plunger head element, if needed e.g. for syringes having a larger inner diameter interacting with a correspondingly large stopper. This additional enlarged plunger head feature can be used for larger syringes, e.g. suitable for a fluid volume of 2.25 ml. In case of smaller syringes, e.g. suitable for a fluid volume of 1 ml, the enlarged plunger head component or feature is omitted and the plunger has a simple parallel cylindrical shape on its proximal end.

In the middle portion of the plunger, a pair of opposing rectangular through holes may be provided in the wall of the hollow element. It should be noted that a pair of through holes, or slots, is not required, a single through hole can be used. The plunger may have additional through holes, or pairs of through holes, comparable to the through holes, at different axial positions which allow an adaptation to different syringe sizes or filling volumes of the drug. At the distal end, the hollow element may be provided with a circular opening providing access in longitudinal direction for receiving the drive spring. The proximal end of the hollow element may comprise the stopper engaging end, or plunger head as discussed above and may include a rotational alignment feature.

The retainer may act as the control member for a plurality of control functions of the power-pack. The retainer may be formed from a hollow cylindrical body. On two opposing sides the cylindrical body may include a U-shaped cutout forming a longitudinal flexible arm, respectively. The longitudinal flexible arm may be integrally connected to the hollow cylindrical body at its distal end. At its proximal end, the flexible arm can be provided with a chamfered feature, projecting radially outwards projection and, on the opposite side, i.e. on its radial inner side, a corresponding chamfered feature, projecting radially inwards. Moreover, the cylindrical body can be provided with two opposing longitudinal cutouts in an area rotated by 90° relative to the flexible arms formed by the cutouts. The longitudinal cutouts may extend approximately with the same longitudinal extension as the U-shaped cutout, or further, in distal direction. In the region of about one third of the longitudinal length of the cutouts close to their proximal end, the cylindrical body may comprise lateral projections transversely bridging the cutouts. These lateral bridging projections are continued close to the proximal end by additional projections having the same outer circumferential shape.

At its proximal end, the cylindrical body of the retainer may be provided with two or more flexible arms integrally formed with the cylindrical body and inclined at an angle relative to the proximal front surface of the hollow cylindrical body. These flexible arms can be connected to a ring-shaped head portion. The ring-shaped head portion can be formed as a bushing with a cylindrical portion and two opposing proximal arch-like projections. The head portion can be integrally formed with the flexible arms or formed as a separate piece fixedly connected to the flexible arms, e.g. by means of an intermediate connecting ring.

The flexible arms allow for certain degree of tolerance and compensation for different syringe sizes. Moreover, these flexible arms bias the syringe axially in the proximal direction by acting on the distal end of the syringe to keep it in a more or less fixed position. Conversely, the biasing element ensures the retainer and connected components are biased distally.

At its distal end, the cylindrical body of the retainer can be formed with a circumferential groove. The distal end may be provided with a distal end surface having a central opening. In its interior close to the distal end, the cylindrical body can be provided with inner guiding ribs running in axial or longitudinal direction between the distal end surface and the longitudinal section having the circumferential groove. The cylindrical body may have varying diameters, blended accordingly between the diameter sizes for the purposes of assembly within the confines of other system components arranged or connected concentrically around the retainer.

Moreover, the safety shield is held in the assembled initial state by the removable cap in the axial position. In particular this has the purpose to avoid unintended movement in distal direction, i.e. if the device is dropped and experiences a shock when it falls on the ground. This is achieved by an engagement between the projections formed on the outer circumferential surface of the cylindrical body at the proximal end of the safety shield and the two projections formed on the inner circumferential surface of the inner ring portion of the removable cap body. Thereby, the projections can block any axial movement of the safety shield in distal direction relative to the removable cap mounted to the housing and thereby relative to the housing.

At the distal end, the distal end cap can be fixedly and inseparably attached by the snap-fit arrangement to the longitudinal housing, wherein the projections formed on the outer circumferential surface of the skirt portion of the distal end cap engage into and with the through holes formed on the distal end of the housing.

Moreover, in the assembled state, the syringe can be held within the syringe holder, which is received in the ring structure of the housing. As described above, the syringe holder can be positioned relative to the housing by means of the ring structure, wherein the transverse projections can engage into respective cutouts and a further projection may project into the hollow space provided by the U-shaped element of the syringe holder. The syringe may be assembled in an axial or lateral direction into the syringe holder before assembly of the syringe holder into the housing or following assembly of the syringe holder into the housing depending on the syringe geometry. Any U-shaped element of the syringe holder is intended to be rigid and do not flex-out during assembly of the syringe for the purposes of allowing the rigid needle shield to pass through or during operation. It is to be noted that the syringe can be held rotationally within the syringe holder or can be allowed to rotate freely.

Assembling the syringe inside a device can be problematic with glass breakage and difficulty to check final position. With the side loading of the syringe to the syringe holder better control and access to critical features can be achieved. Assembly may be by visual positioning and checking. Assembly may be performed by dimensional and force control and checking.

Moreover, the syringe together with the syringe holder can be pressed via the syringe flange by means of the head portion of the retainer in proximal direction against the conical and stepped ring structure of the housing, wherein, once fully assembled with the power-pack, the flexible arms of the retainer act as axial biasing means providing a spring force axially in the proximal direction, in order to hold the syringe in place within the syringe holder and positioned thereby.

Further Features

The syringe assembly may comprise a hollow syringe body containing the fluid product and an injection needle formed with the hollow syringe body. It should be understood that the term hollow syringe body is intended to include a hollow cartridge or other hollow body within which a piston, or movable stopper, can be moved to create a variable volume chamber from which fluid can be expelled via an outlet. The outlet may comprise an integral injection needle, such as those found in a staked needle syringe, or the injection needle may be coupled to hollow body in another way, such as luer lock, screw connection or other suitable connection. It is also possible that the outlet from which the fluid can be expelled is created during the actuation of the automatic drug delivery device, for example by a rear portion of the injection needle puncturing a membrane.

The housing in a cross-section of at least a portion of the housing may have a non-circular shape to provide an anti-rolling function. The housing may be formed by an opaque or a transparent material in whole, or in part.

The fluid product is typically a pharmaceutical composition/formulation suitable for parental administration to a human or animal subject. The pharmaceutical composition/formulation comprises one or more pharmaceutically active substances, including low molecular weight compounds and/or biopharmaceuticals, such as recombinant products. Examples of pharmaceutically active substances include antibodies (full length or active fragments thereof), polypeptides/peptides and derivatives therefore, as well as nucleic acid molecules, which may be part of vectors, viral particles, optionally in combination with delivery vehicles such as lipids. Nucleic acids and polypeptides/peptides may be produced by biological processes or synthetically. In one example the fluid product comprises a pharmaceutically active substance selected from secukinumab, cankinumab, bimagrumab, omalizumab, tesidolumab, iodelcizumab, elgemtumab, lacnotuzumab, ofatumumab, ligelizumab, ranibizumab, brolucizumab and ianalumab.

The present invention also relates to an automatic drug delivery device, in particular an autoinjector, for dispensing a fluid product, in particular a fluid medicament, including:
a longitudinal housing extending along a longitudinal axis and having a proximal end close to the dispensing site, a distal end opposite to the proximal end and a hollow interior;
a removable cap mountable to the proximal end of the housing;
a syringe assembly mounted in a mounting position inside the housing and having a hollow syringe body and an injection needle integrally formed with the hollow syringe body including the fluid product;
a loaded or energized drive mechanism which can be triggered by a trigger element in order to initiate the dispensing of the fluid product;
a feedback mechanism providing a tactile and/or audible and/or visual feedback to a user indicating an actual state of operation;
wherein the injection needle protrudes with a sharpened needle tip out of the proximal end of the housing when the syringe assembly is in its mounting position;
wherein the loaded or energized drive mechanism is operatively coupled to a safety shield movable within the longitudinal housing,
wherein the safety shield is a biased into a proximal position in which it protrudes out of the proximal end of the longitudinal housing in order to cover the injection needle with its sharpened needle tip, and wherein the safety shield is movable against a biasing force into a distal position in which the injection needle with its sharpened needle tip is exposed for injection;
wherein during use the automatic drug delivery device comprises the following operational states:
an initial state, in which the automatic drug delivery device is fully assembled and the removable end cap is mounted to the longitudinal housing;
a ready to use state, in which the removable end cap has been removed from the housing and a safety shield covers the needle tip;
a triggered state, in which the automatic drug delivery device is being pushed against a patient's skin, thereby the safety shield is being pushed into the longitudinal housing and releases the needle tip for injection;
a dispensing state, in which the fluid product is being dispensed into the patient's tissue; and
a used state, in which the fluid product has been fully dispensed, the automatic drug delivery device has been removed from the patient's skin and the safety shield covers the needle tip.

The safety shield may be provided with at least one, possibly two, longitudinal arms extending in the distal direction guided within the longitudinal housing. The safety shield may interact with a safety shield spring which biases the safety shield in the proximal direction via the, or each, longitudinal arm. This may allow for a relative simple and compact triggering mechanism. The basic mechanical triggering and biasing functions can be concentrated on the distal end of the housing apart from the safety shield and the syringe assembly.

The loaded or energized drive mechanism may include a plunger biased by a drive spring in proximal direction. The plunger may act on a stopper which may be sealably guided within the syringe body. The plunger may act on the fluid product included within the syringe body.

The proximal end of the drive spring may act on a distal end of the plunger. The distal end of the drive spring may act on a fixed end cap which may be fixed to the distal end of the longitudinal housing. The fixed end cap may include a rod member for guiding the drive spring in longitudinal direction. The fixed end cap may also be mounted to the longitudinal housing by a snap-fit engagement.

The distal end of the drive spring together with the distal end of the plunger may be received within a rotary click element rotatably arranged within the fixed end cap. The rotary click element and the fixed end cap may provide engaging and corresponding saw-tooth profiles permitting a relative rotation of the rotary click element relative to the fixed end cap in one rotary direction and preventing a relative rotation in the opposite rotary direction. The rotary click element may be settable in its axial position depending on the rotary position of the rotary click element relative to the fixed end cap. Depending on the initially selected rotational position of the rotary click element the intensity of an audible or tactile signal can be chosen.

The autoinjector according to the invention may be formed by different subassemblies, e.g. a proximal subassembly including the end cap, a prefilled syringe unit, and a power-pack subassembly. These three subassemblies may be provided as separate pre-assembled modules for assembling the device according to the invention. This allows pre-assembly of the syringe unit and the power-pack. Moreover, a corresponding prefilled syringe can be used with a demanded medicament provided therein in a sealed manner and with the predetermined volume for drug delivery.

The three subassemblies can be assembled to form the complete autoinjector by insertion of the prefilled syringe into the syringe holder (if required) within or without the syringe unit and thereafter plugging the power-pack, from the distal side, into an open distal end of the body of the syringe unit until it locks into a predetermined non-separable position. By this modular structure, the device according to the invention can be easily assembled in an error-free manner. It should be understood that the term prefilled syringe unit, or prefilled syringe, is being used herein to refer to a syringe body which is coupled to an injection needle. The syringe body comprises a variable volume chamber filled with a medicament that can be expelled through the injection needle.

If necessary, the syringe may be attached, or coupled, within or outside the housing to a syringe holder to provide the syringe assembly, or syringe subassembly.

The proximal syringe unit subassembly may comprise the removable end cap formed by an end cap body, a blade washer and a proximal end cap cover. Moreover, the proximal syringe unit subassembly may comprise a safety shield, a longitudinal housing and a syringe holder.

The syringe subassembly may include a rigid needle shield with an insert, a glass body with a staked needle, a medicament and a stopper.

The power-pack subassembly may include a trigger element, a trigger spring, a shield retention indicator, a plunger, a drive spring, a retainer, a shield retention indicator inner element and a distal end cap.

The plunger may have a proximal end, wherein the proximal end is adaptable to suit to different syringe sizes, preferably by being coupled with an adaptor piece.

The device may have a label on the outside of the housing, wherein the label comprises a black internal surface which restricts light and the ability to see the end of use indicator before use. The device may have a label on the outside of the housing which is either opaque and thereby prevents the ability to see the end of use indicator before use, or is sufficiently opaque to restrict the ability of the user to see the end of use indicator prior to use.

The safety shield may include a ring-shaped hollow cylindrical body at its proximal end with two diametrically opposing longitudinal arms. This arrangement of the body and the longitudinal arms can be integrally formed or formed from separate pieces, i.e. the cylindrical body may include a separate cover which can be formed from a coloured material.

The ring-shaped body may have one or more projections close to its distal end. The distal end of the ring-shaped body may be provided with an annular collar having a rounded outer circumferential ring with one or more opposite slots. A longitudinal hollow portion may extend from this annular collar in distal direction, divided by the slots in two separate halves. The two longitudinal arms can be integrally formed with the distal end of the collar and have a stepped course, such that a first transition between the collar and a first longitudinal arm portion forms a first shoulder and wherein a second transition between the first longitudinal arm portion and a second longitudinal arm portion forms a second inclined shoulder. Each of the second longitudinal arm portions may have on its outer circumferential surface a projection protruding radially outwards and having a sharp radial surface facing in proximal direction and an inclined chamfered surface facing in distal direction. In line with the projection the longitudinal arm portion has a rectangle a through hole close to its distal end.

The outer circumferential surface of each second longitudinal arm portion may include an inner guiding projection. Moreover, the inner circumferential surface of the cylindrical body may include guiding ribs protruding radially inwards. These inner guiding ribs can be provided for guiding the rigid needle shield during syringe assembly. As an alternative, the outer circumferential surface of each second longitudinal arm portion may have guiding ribs and the inner circumferential surface of the cylindrical body may include a guiding projection.

The cylindrical body may be smoothly formed and chamfered on its front (proximal) end such that it does not injure or scrape on the patient's skin. As mentioned above, the cylindrical body, together with the longitudinal arms, may be a single-piece arrangement or a multi-piece assembly.

The housing has the purpose of forming the main body of the device. It is formed from a stable, rigid, transparent or opaque material. If not entirely transparent, the housing can be formed with drug viewing cutouts or transparent windows in order to allow the liquid contents of the syringe, and the state of the device visible to a user. Additionally, or alternatively, the position of the stopper may be visible to a user through such windows. The state of the device may include the position of the stopper within the syringe body. The housing is formed by a longitudinal tubular member. At its proximal end, the tubular member may be provided with a hollow cylindrical portion having a generally circular cross-section and a front surface. At a distance from the proximal end, the longitudinal member can be provided with an arch-like extension or lobe, having the same general shape and cross-section as the end cap cover, in order to provide further geometry with an anti-roll function on a flat surface e.g. for when the removable end cap is removed.

At the proximal end of the housing, the cylindrical portion may be provided on its circumferential inner surface with rib-like opposing projections, protruding radially inwards, which may be hidden or obscured to the outside, and which are adapted to interact with the removable end cap. Moreover, in its middle section, the housing may be provided with two opposing longitudinal through holes, having the function of guiding slots. As an alternative, these through holes can be replaced by guiding channels which open to the inside of the housing, but which are closed on the outer circumferential surface thereof. In line with the guiding slots but closer to the distal end, the housing may be provided with further opposing through holes, which as an alternative can be also provided as internal recesses which are closed at the outer circumferential surface. Close to its distal end, the housing may be provided with a pair of opposing transverse through holes, which as an alternative can be also provided as internal recesses which are closed at the outer circumferential surface, for the purpose of attachment to the power-pack subassembly. The distal end may be further provided with a distal front surface, which has two opposing short notches for the purpose of enhancing rotational coupling with the power-pack.

In its interior, the housing may be provided with a ring or double-ring structure, which is integrally connected to the tubular member in the region of the cylindrical portion by means of at least one rigid connecting arm. The connecting arm can be formed by a stable U-shaped structure with two lateral longitudinal connecting ribs and one transverse connecting rib running in circumferential direction. The size of the connecting ribs and the U-shaped sectional shape are to provide structural rigidity to the housing. This joining geometry is also important for the flow of the material when the component is molded.

Moreover, the ring structure or double-ring structure may have an outer ring running with a conical transition portion into a hollow inner ring. To the proximal end, strengthening ribs may stabilize the connection between the outer ring and the inner ring. At the distal end, the conical transition portion may be provided one or more cutouts and/or rib-like axial projections. The arrangement of the cutouts and the axial projections may be provided for positioning the prefilled syringe directly, or in connection with a syringe holder.

The trigger element may be formed by a broadly cylindrically shaped hollow body. At its proximal end it has a front surface surrounded by a chamfered rim and provided with two opposite lateral tabs extending in the radial direction. From the front surface of these lateral tabs two rectangular projections may extend in longitudinal axial direction. The projections can be provided with chamfered projections, extending radially outwardly for biasing of the safety shield. The tube shaped hollow body may extend in the distal direction and provides, in its middle portion, a surrounding annular reinforcement rib connected to the reinforced proximal end by longitudinal ribs. Between the proximal end and the reinforcement rib, two opposing rectangular hollow box elements or recesses formed by other wall structures may be provided at the outer circumferential surface of the trigger element, wherein these box elements or recesses provide a hollow space, respectively, in which additional components, e.g. electronic sensors or the like can be provided. The trigger element acts as a temporary blocking element for the shield retention indicator described below during use of the drug delivery device.

Further in the distal direction, the outer circumferential surface of the tubular hollow body can be provided with a further annular and circumferential reinforcement rib, e.g. having an L-shaped profile to support the spring. The distal end of the tubular hollow body of the trigger element can be formed by a hollow cylindrical portion having a front surface. In its interior, the trigger element may be provided with a plurality, preferably four longitudinal guiding ribs, wherein two pairs of these guiding ribs are connected by an arch-like connecting rib, respectively, which extends in circumferential direction along the inner circumferential surface of the tubular hollow body.

The end plate may obscure easy viewing of the indicator coloured surface when a label is on the outer surface of the transparent housing.

The shield spring biasing the shield retention indicator inner element in the distal direction can be arranged in a hidden way between the shield retention indicator inner element and the shield retention indicator. The whole indicator arrangement can be arranged at the distal and portion of the drug delivery device, which, in use, faces the user and is easily visible.

The distal end cap may have a distal end cap body having the same cross-sectional profile as the distal end of the longitudinal housing, i.e. rounded with an arch-like extension or lobe. The distal end cap body may be formed from a transparent material and closed by a distal surface. A transition between the circumferential surface and the distal surface can be rounded or chamfered. At its proximal end, the distal end cap may be provided with a skirt portion, which can be form-fittingly received in an assembled state within the distal end of the longitudinal housing. Therefore, the skirt portion has a reduced outer diameter and transitions to the distal end cap body via a stepped surface.

In the region of the stepped surface the distal end cap may provide longitudinal protrusions corresponding to the notches described for the longitudinal housing. By interaction of the protrusions and the notches, the distal end cap can be positioned relative to the longitudinal housing. Moreover, the skirt portion may be slotted to provide two or more longitudinal projections. The outer circumferential surface of these longitudinal projections is formed with chamfered snap-fit projections, respectively. These projections are provided to engage in a snap-fit manner with corresponding through holes provided in the longitudinal housing when assembling the device.

It is to be mentioned that the snap-fit engagement between the projections and the through holes—once assembled—should not be easily separable. The device according to the present invention is a single use device and excludes that the distal end cap, after having been fixed to the longitudinal housing, is removed from the housing again. It is not provided or intended to replace or refill the syringe after use or to provide any other access to the interior and the components of the device, once it has been used.

Turning to the interior of the distal end cap, the end cap may be provided with a hollow cylindrical body integrally formed with a bottom surface of the distal end cap. Preferably, the distal end cap is formed by a transparent or opaque material providing a 360° window for showing the indicator in a used state of the device. In its interior, the distal end cap includes a hollow receiving portion, e.g. a cylindrical hollow body, for receiving the distal end of the drive spring received within the distal end of the retainer. However, by choosing a neutral colour for the retainer, this arrangement is not visible from the outside through the transparent distal end cap.

In the assembled or initial state of the device, the end cap is attached onto the longitudinal housing, wherein the end cap is held in circumferential direction by an engagement of each of the inner protrusions formed on the proximal end of the housing within a corresponding receiving space between the two projections formed inside the end cap body. Moreover, the end cap can be held in longitudinal direction by an engagement of each of the inner protrusions formed in the proximal end of the housing located behind the projections formed on the inner ring portion of the end cap body, respectively. Thereby, the removable cap can be held on the housing against an axial withdrawing force by the projections as well as against small twist-off forces, which are below a twist-off force threshold value, by the opposing projections forming the receiving space.

The longitudinal housing may be formed by a transparent or opaque material, having at least a transparent portion or window through which an actual state of operation is visible to a user.

DETAILED DESCRIPTION

The invention will be further describe by way for example only with reference to the following figures in which:

FIG. 2 is an exploded view of the drug delivery device according to FIG. 1 showing subassemblies thereof, in particular a removable cap, a safety shield, longitudinal housing and a syringe holder;

Figure 1:
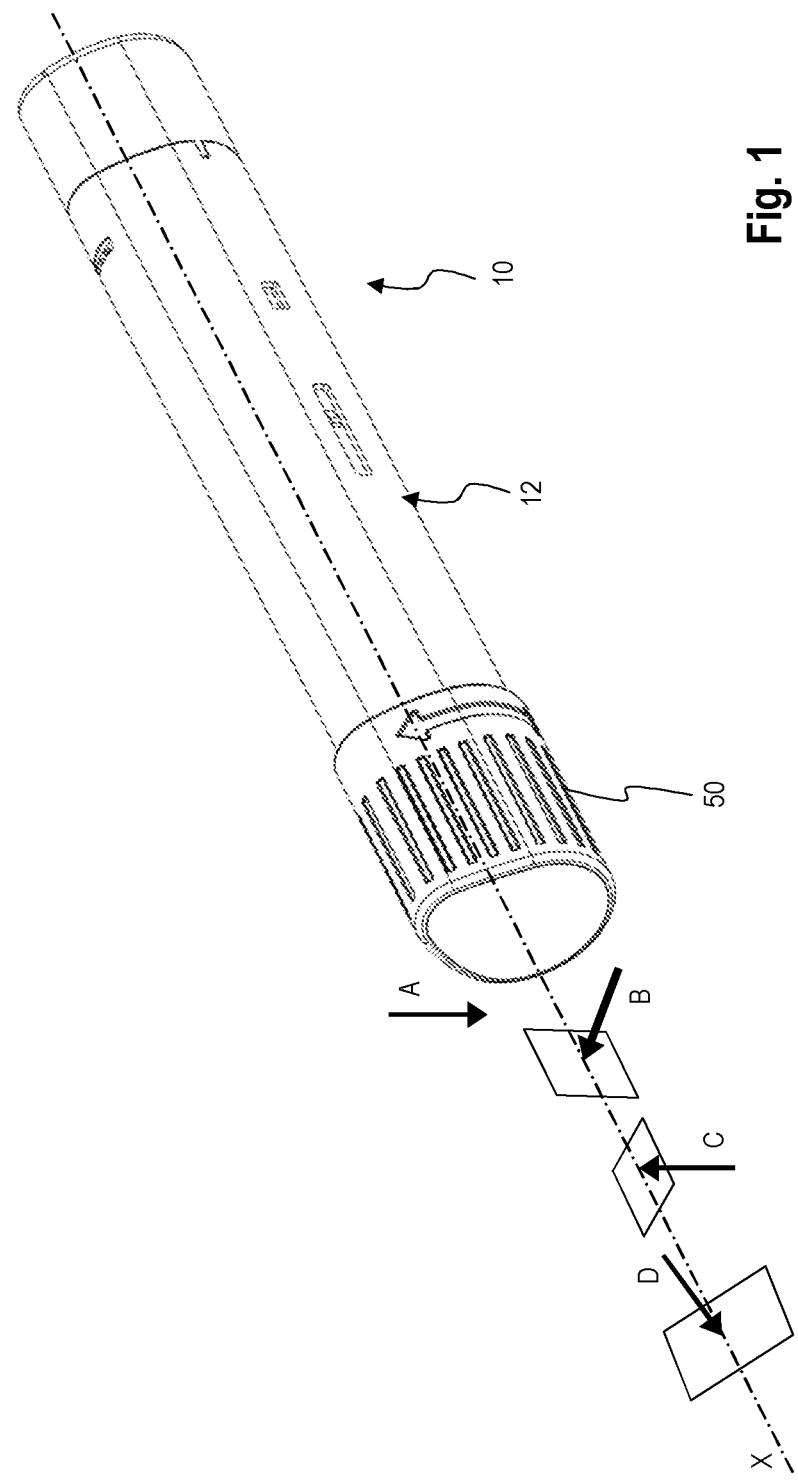
FIG. 1 is a perspective view of a drug delivery in an assembled state.
Figure 20:
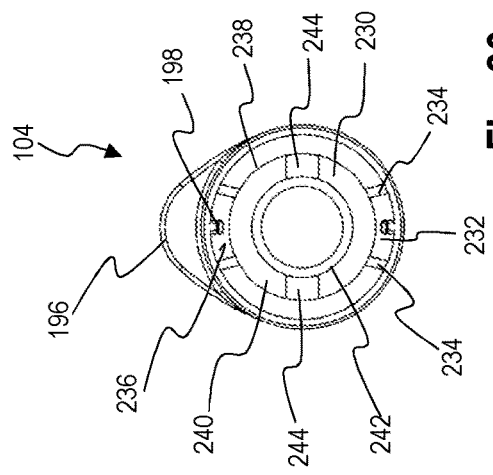
Figure 22:
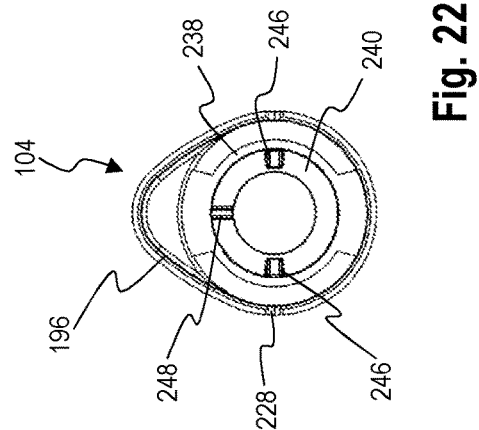
Figure 19:
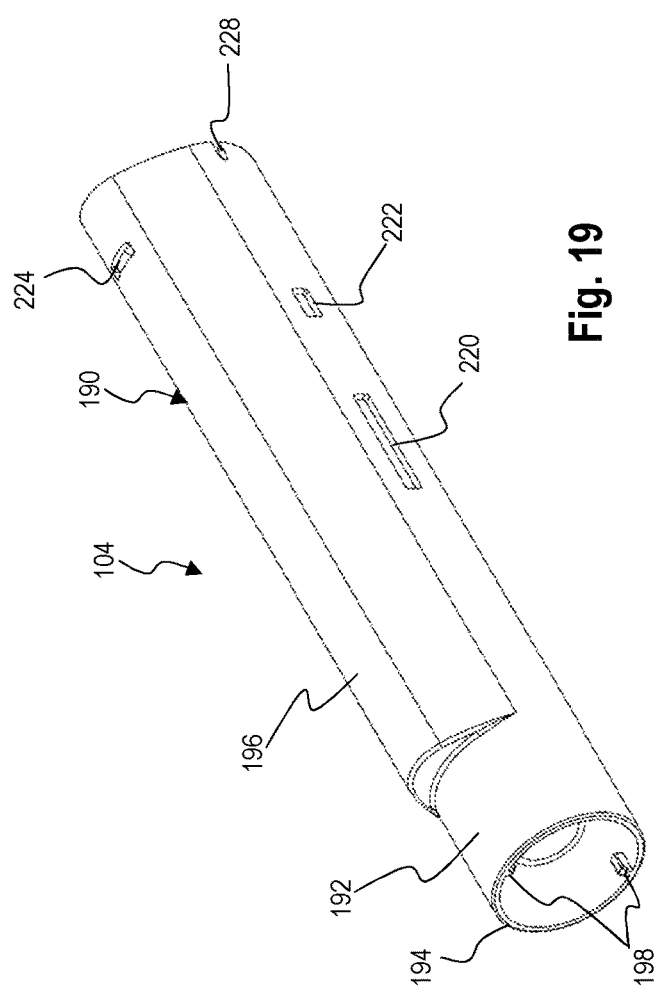
Figure 21:
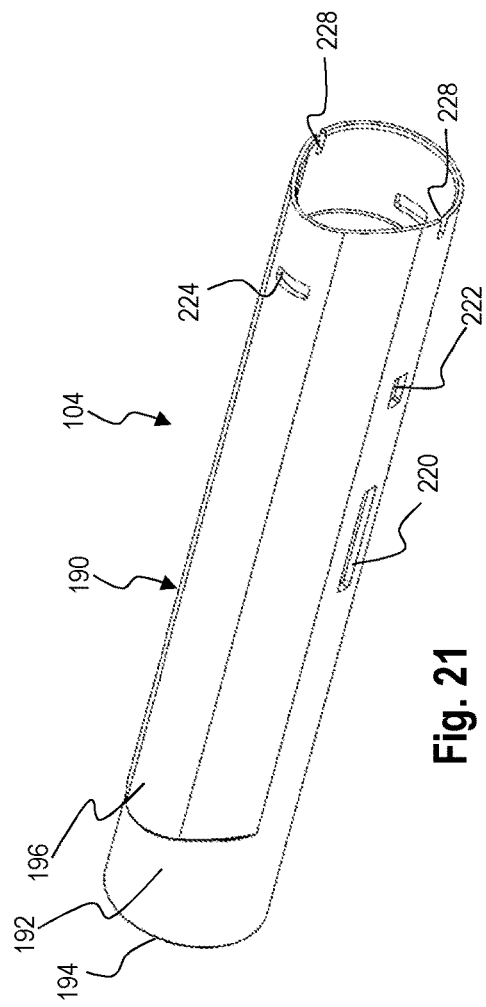
Figure 26:
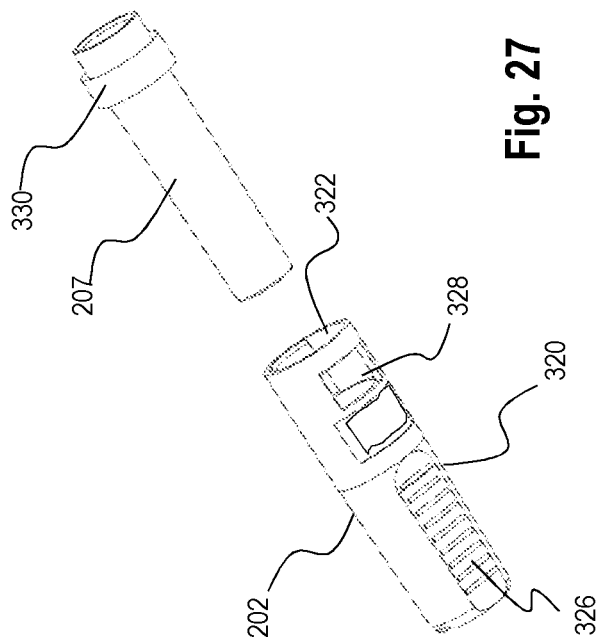
Figure 27:
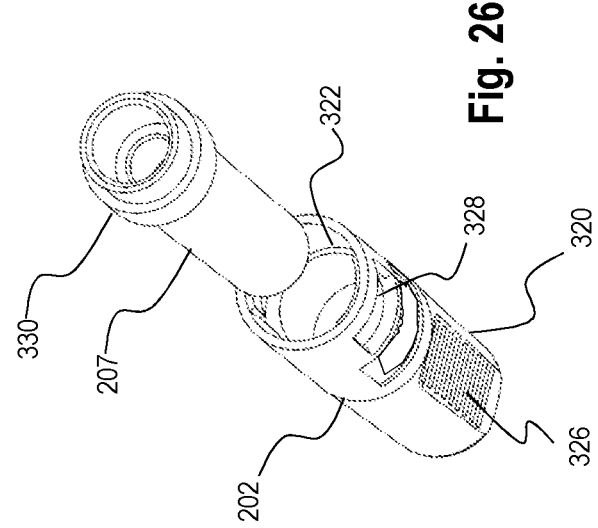
Figure 29:
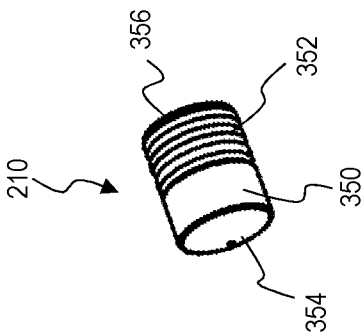
Figure 28:
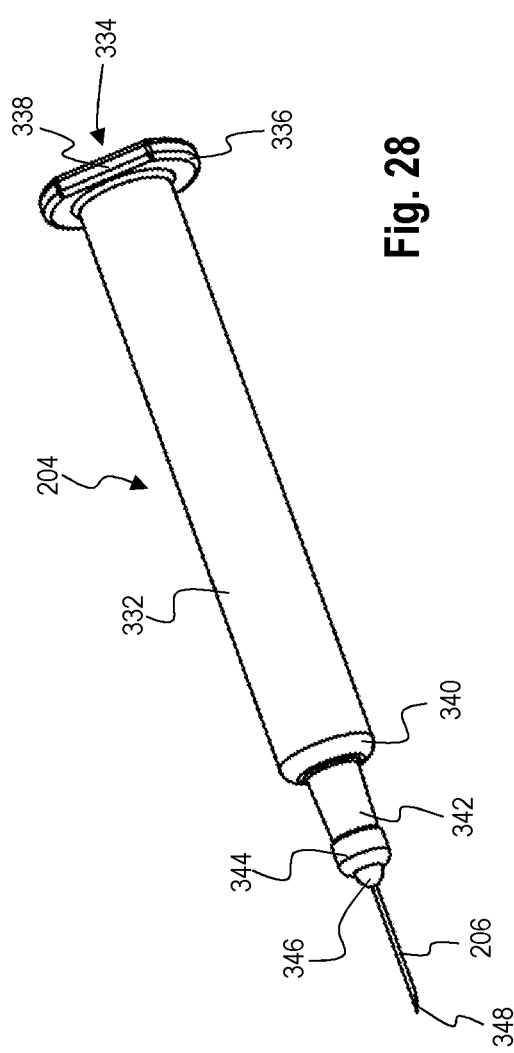
Figure 43:
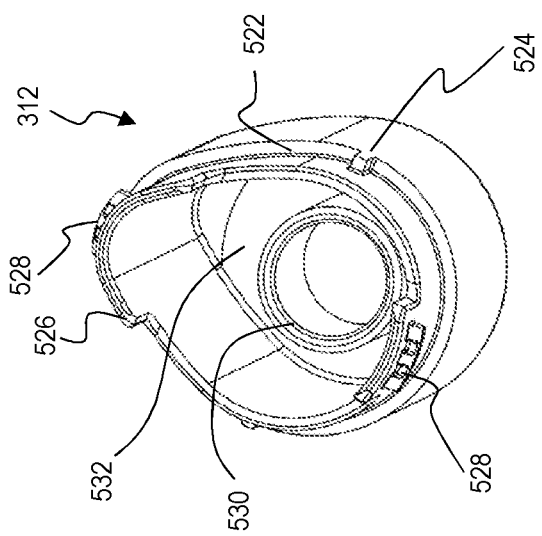
Figure 42:
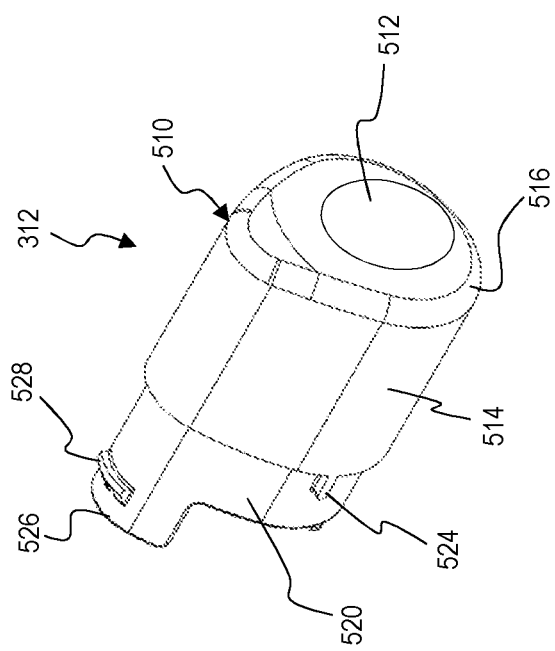
Figure 56A:
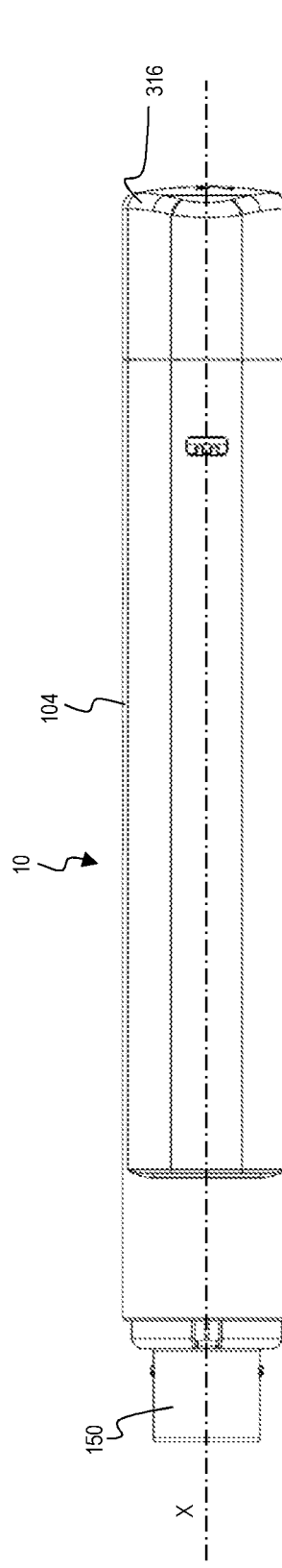
Figure 56B:
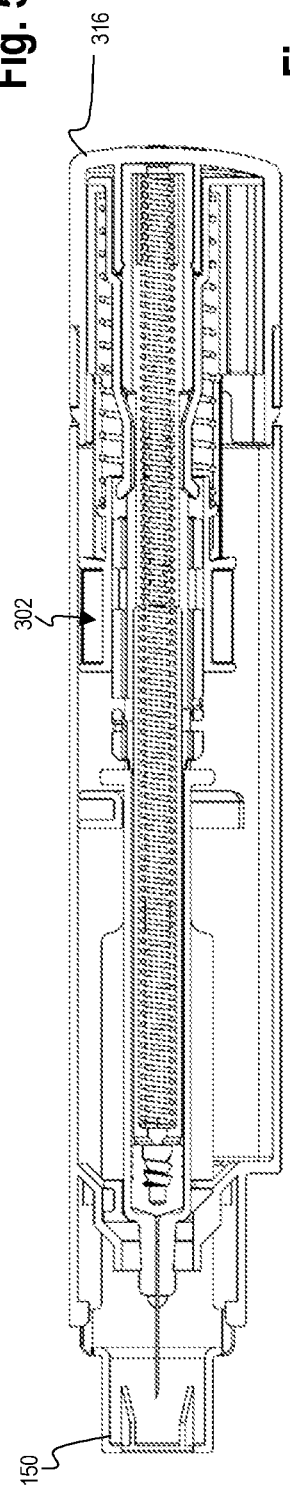
Figure 56C:
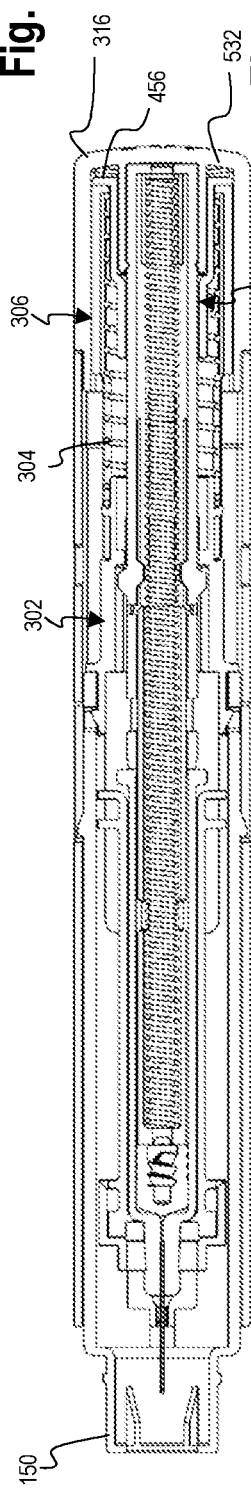
Figure 56D:
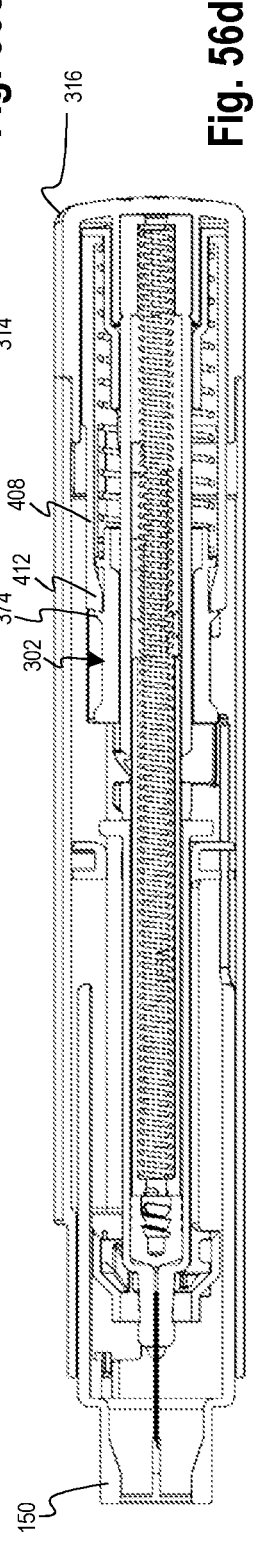
Figure 61:
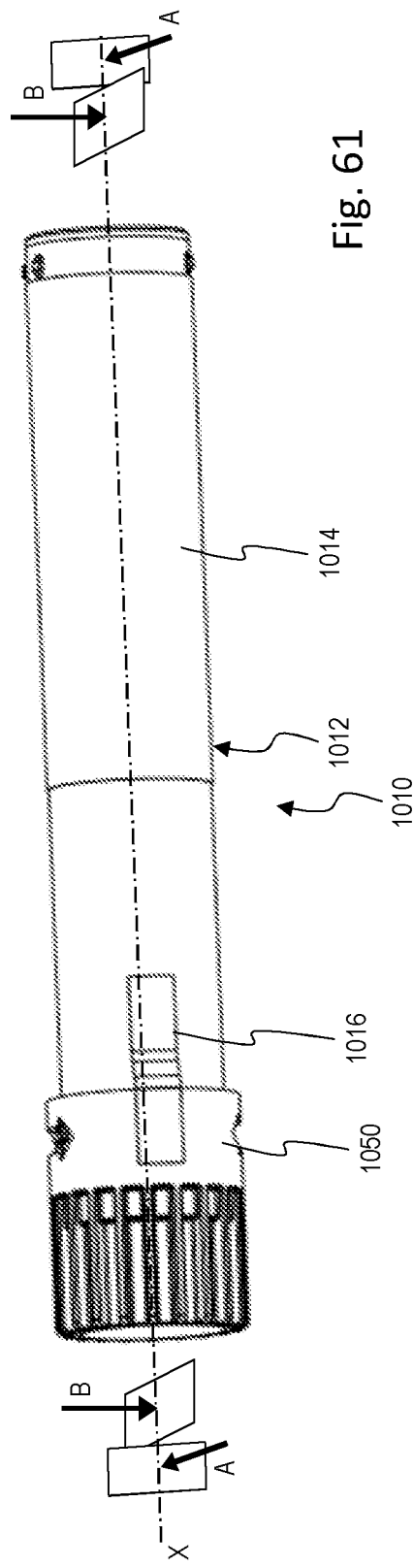
Figure 62:
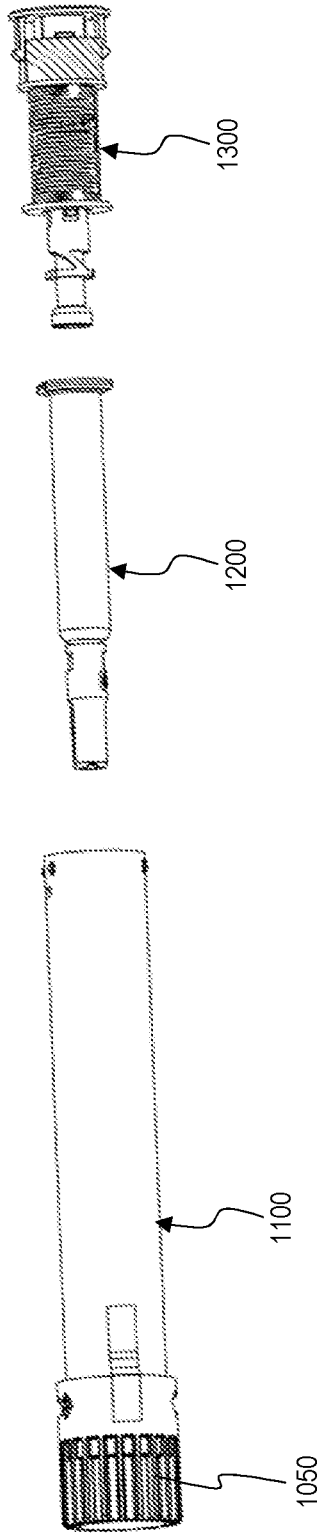
Figure 66A:
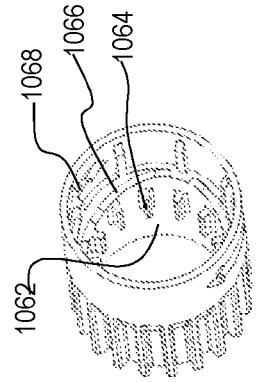
Figure 66B:
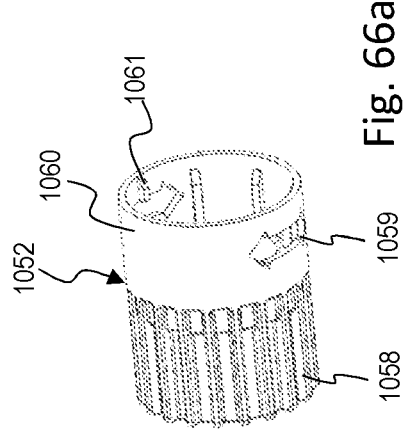
Figure 68:
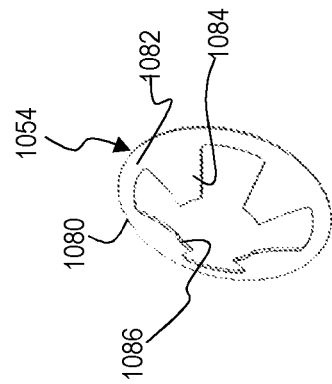
Figure 67:
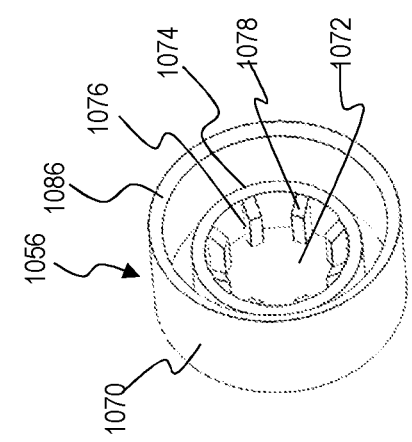
Figure 69B:
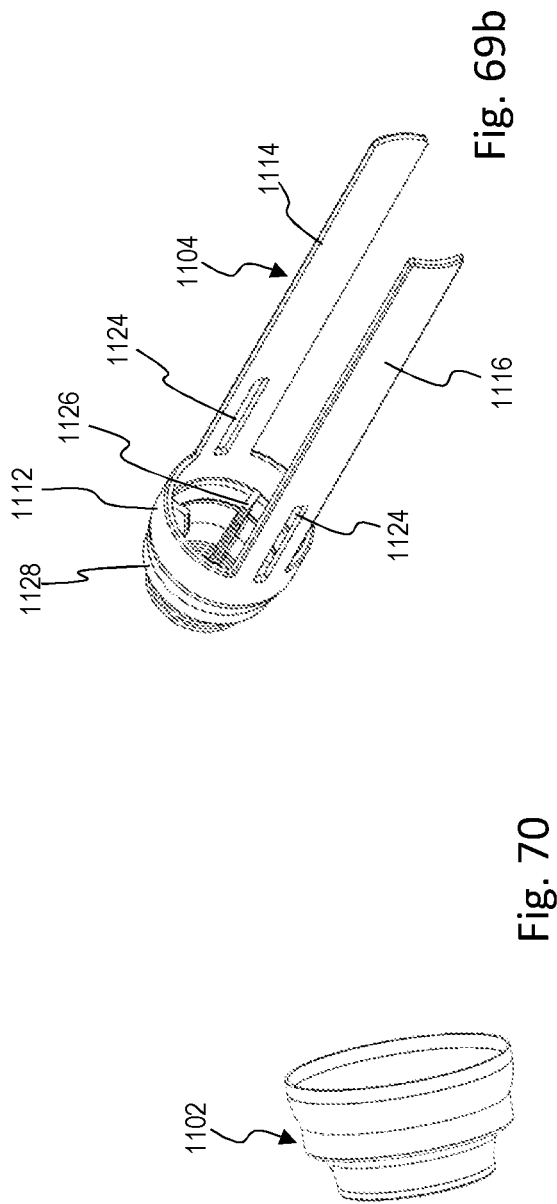
Figure 69A:
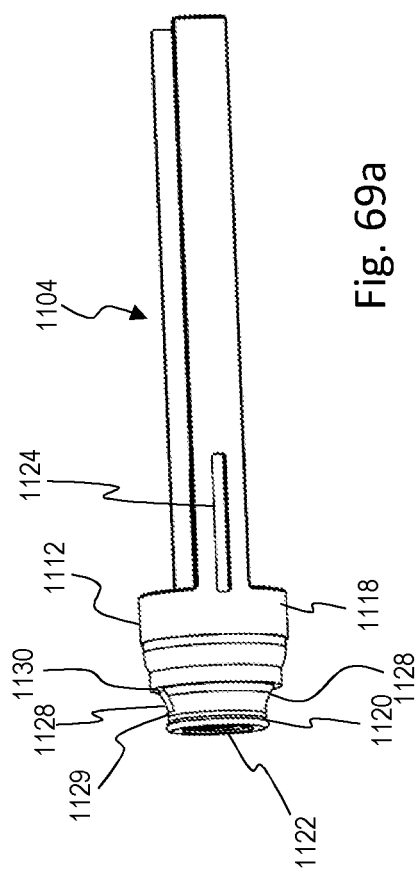
Figure 70:
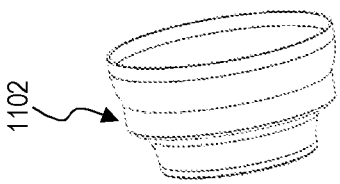
Figure 80B:
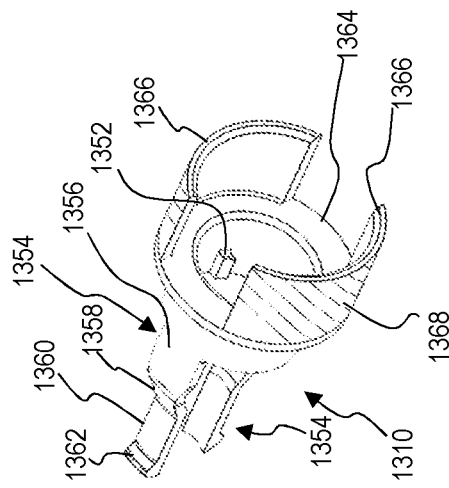
Figure 80A:
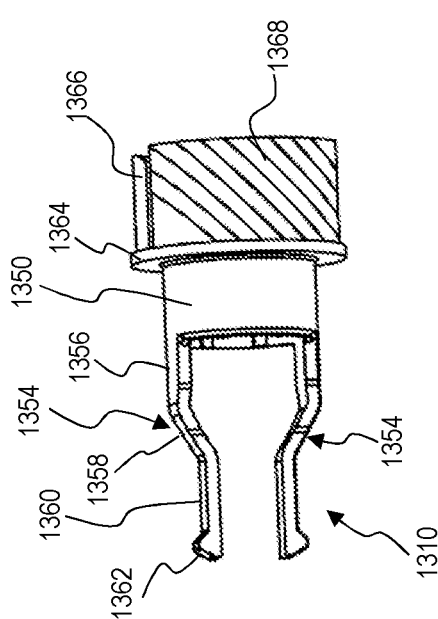
Figure 81B:
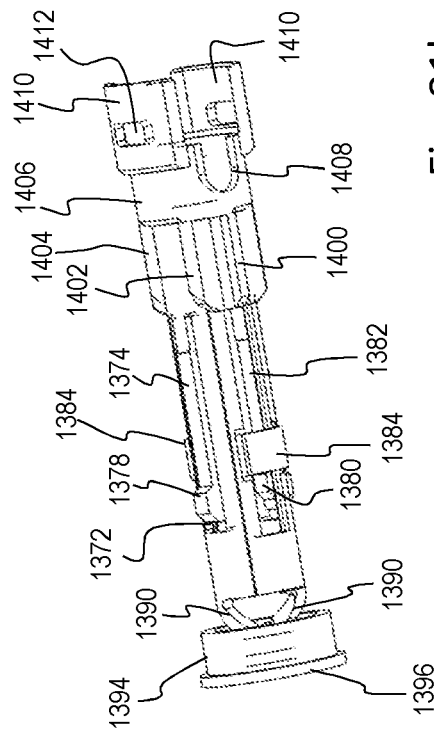
Figure 81A:
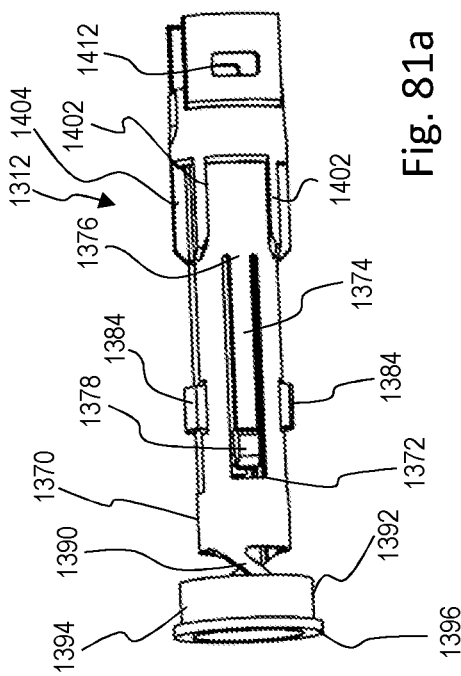
Figure 82B:
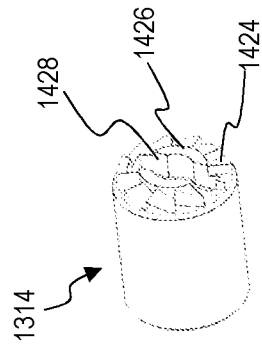
Figure 82A:
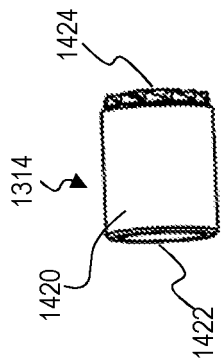
Figure 83B:
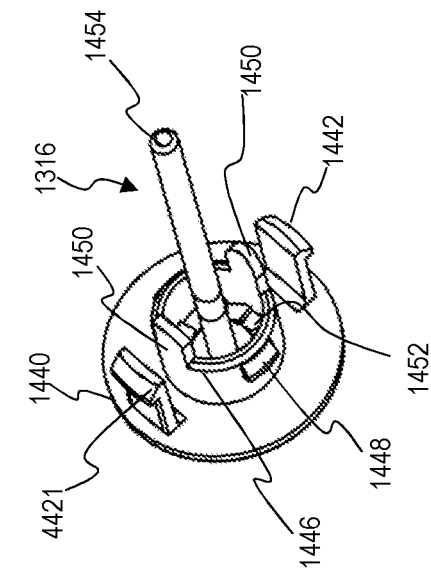
Figure 83A:
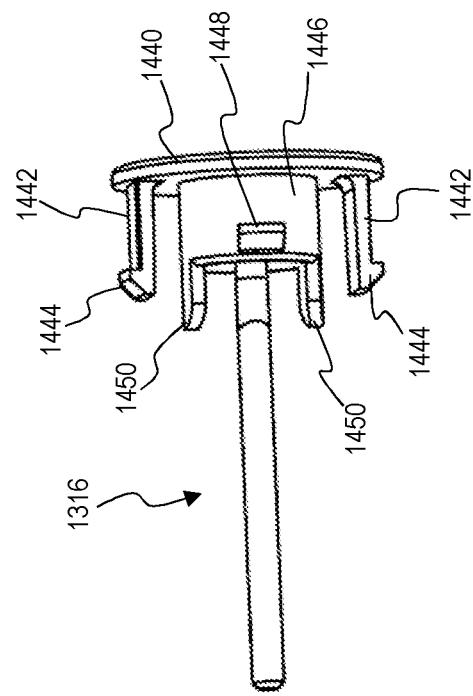
Figure 84A:
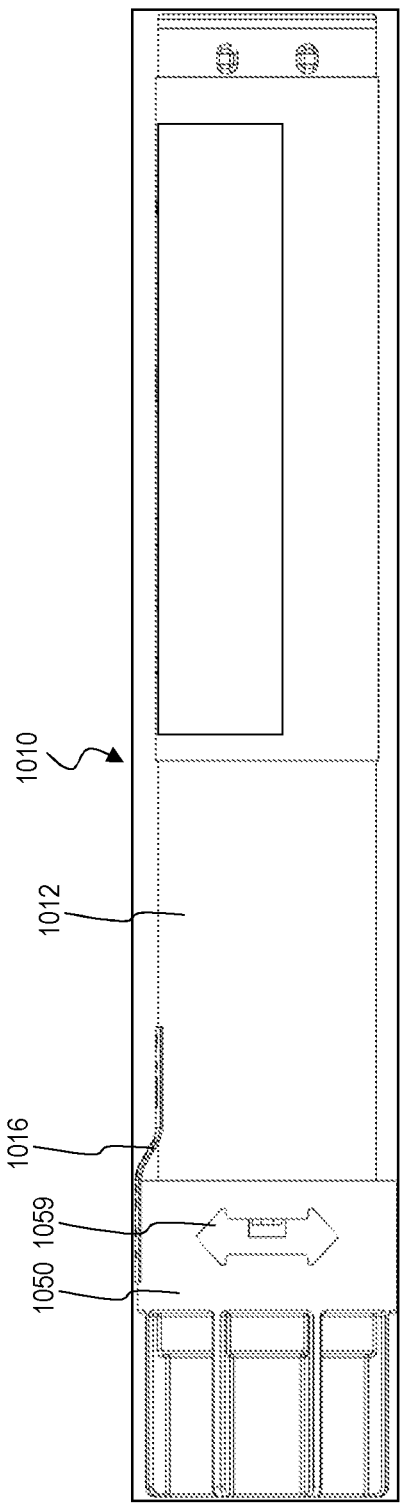
Figure 84B:
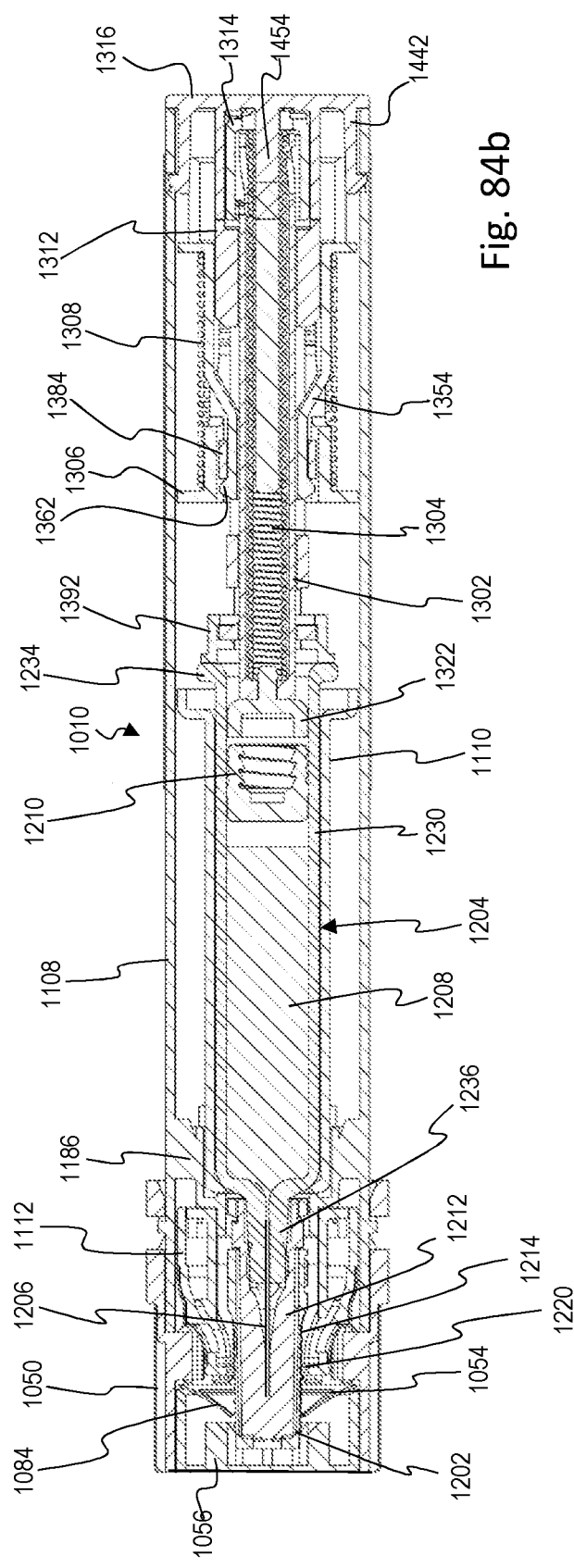
Figure 85A:
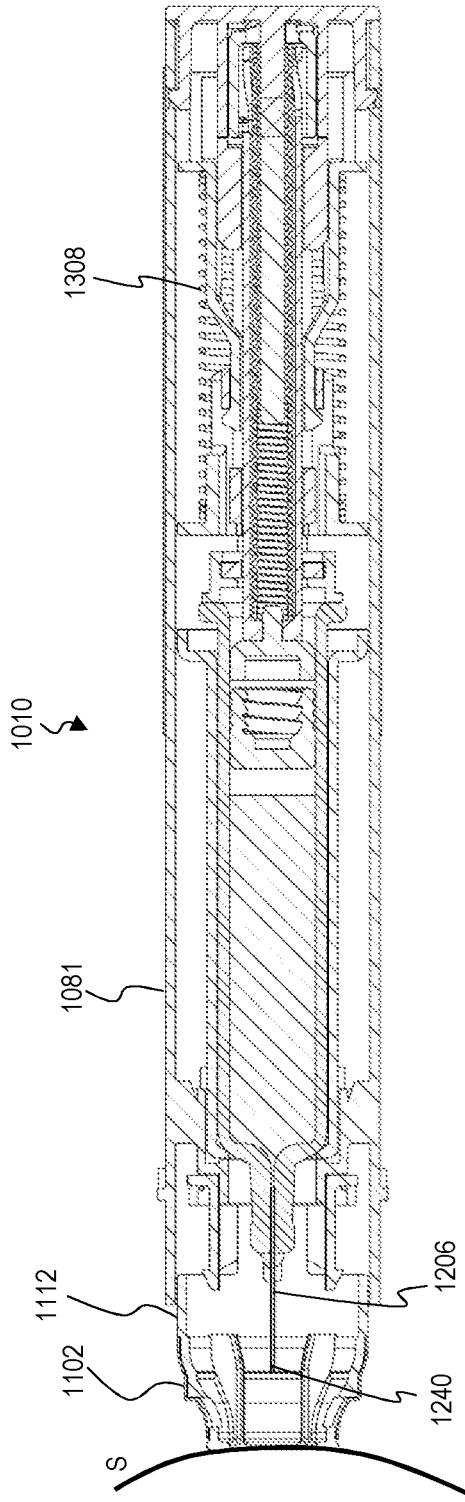
Figure 85B:
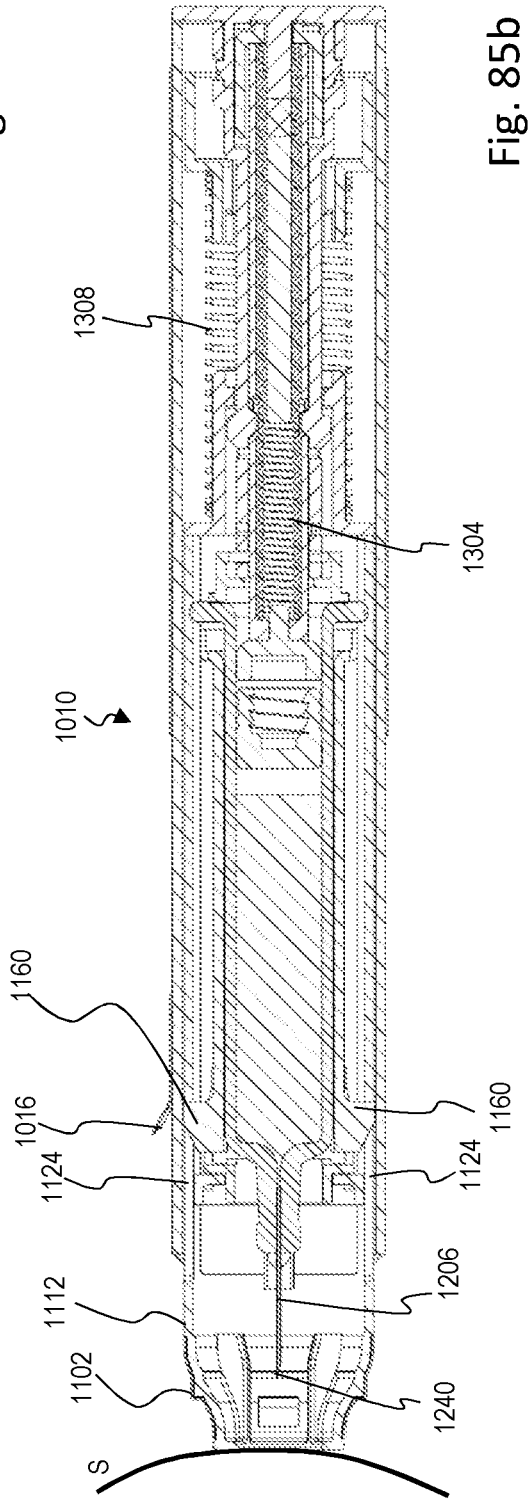
Figure 87A:
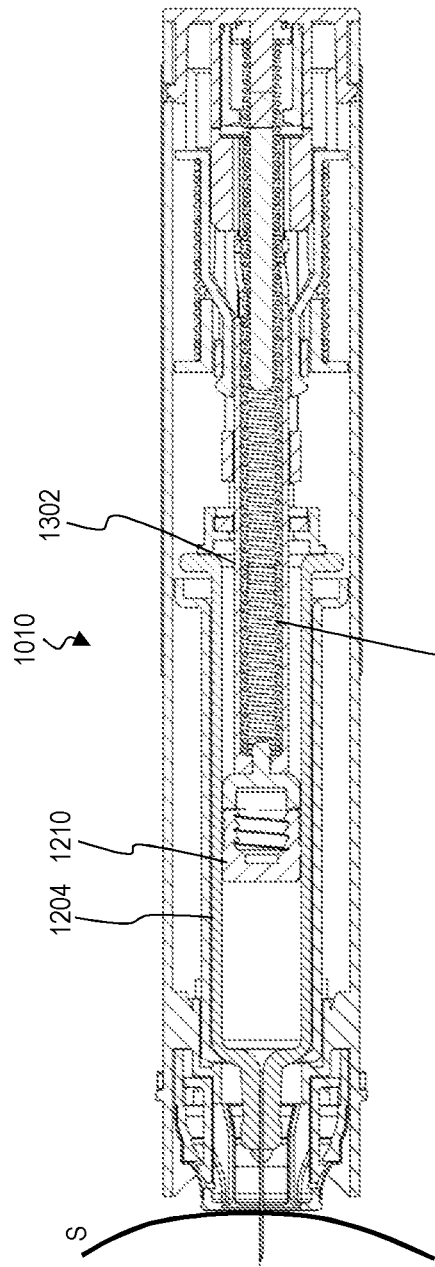
Figure 87B:
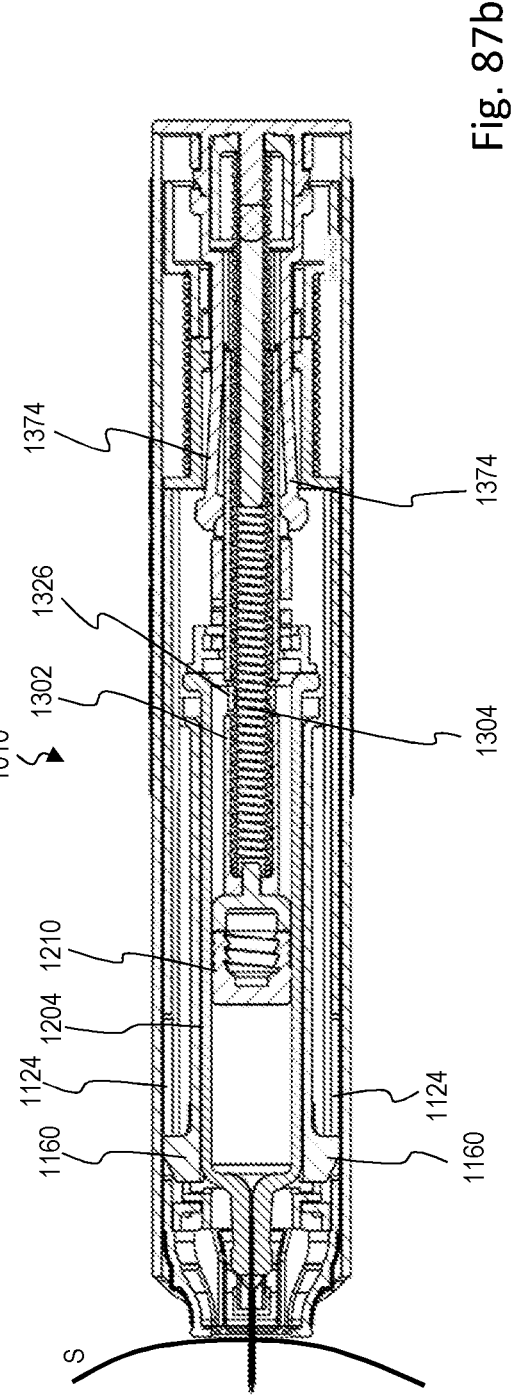
Figure 88A:
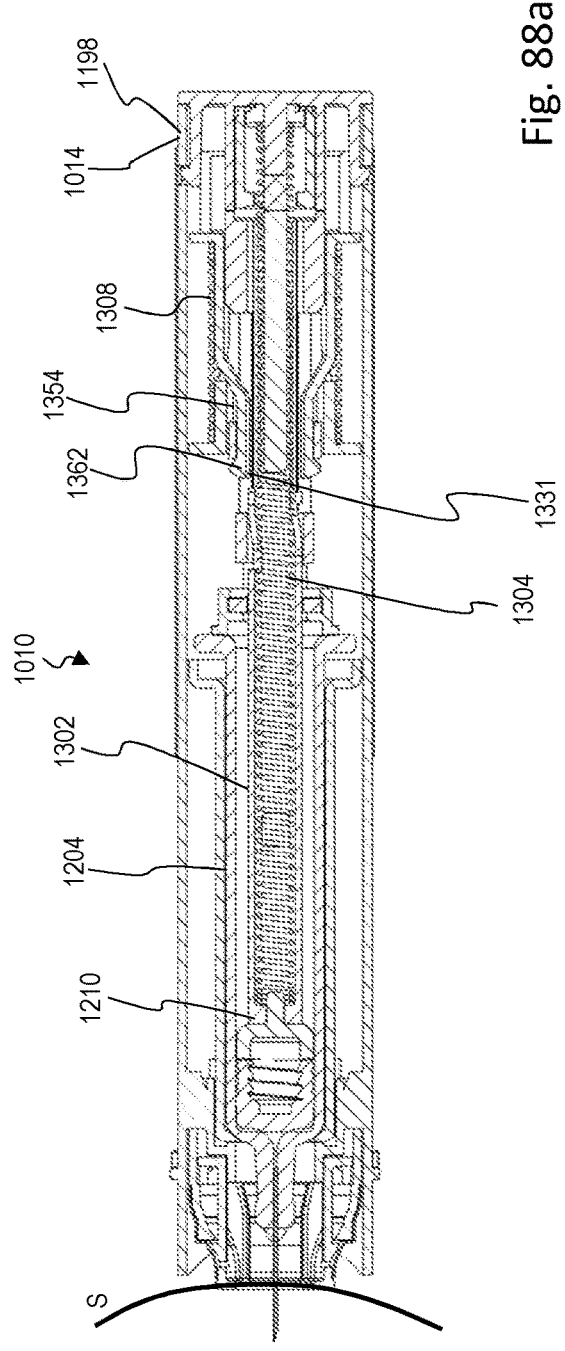
Figure 88B:
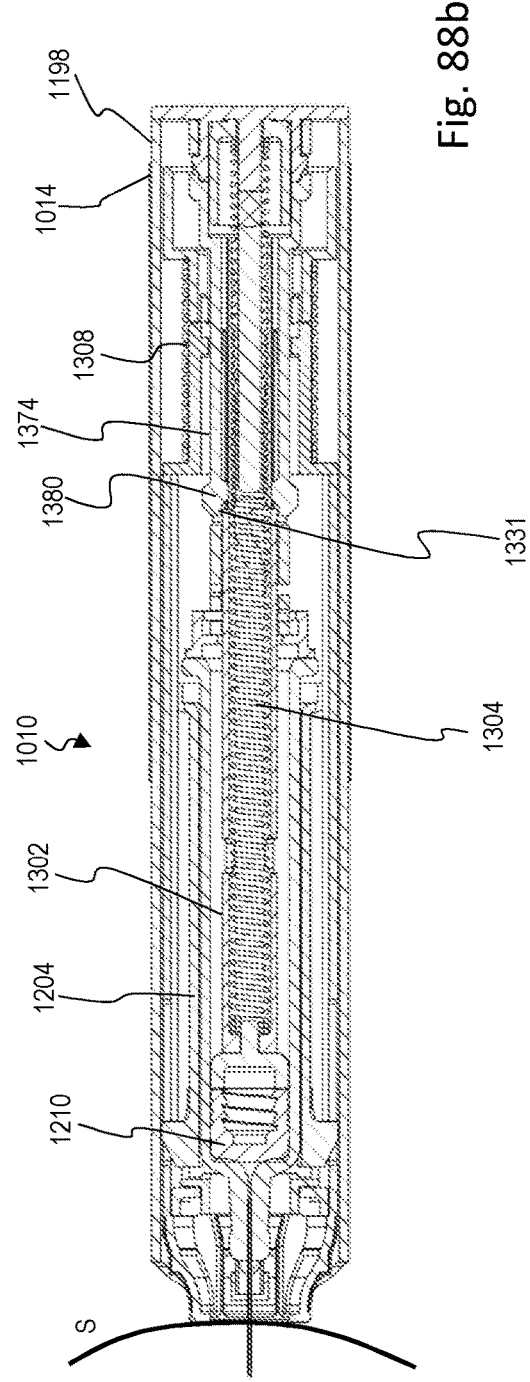
Figure 90A:
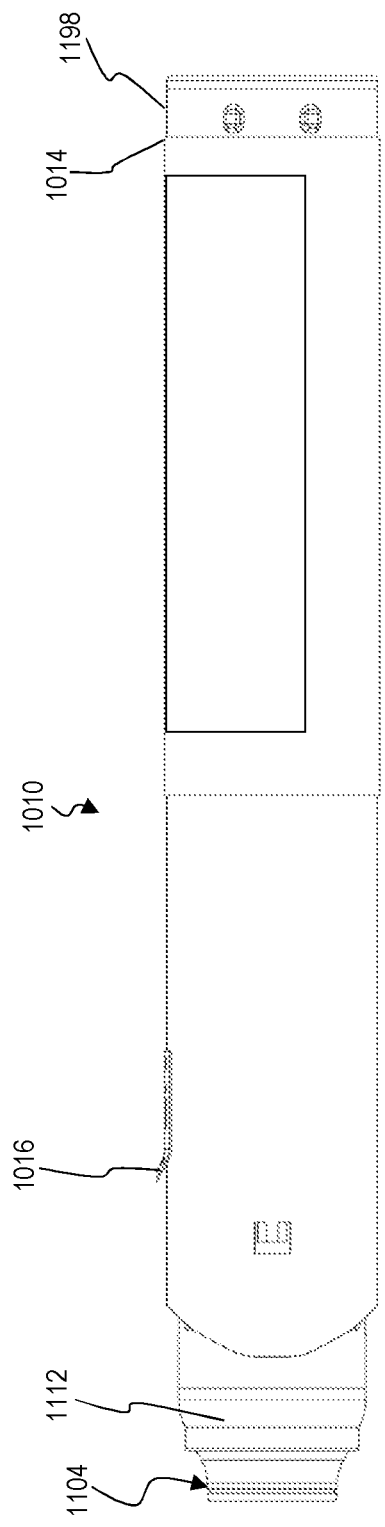
Figure 90B:
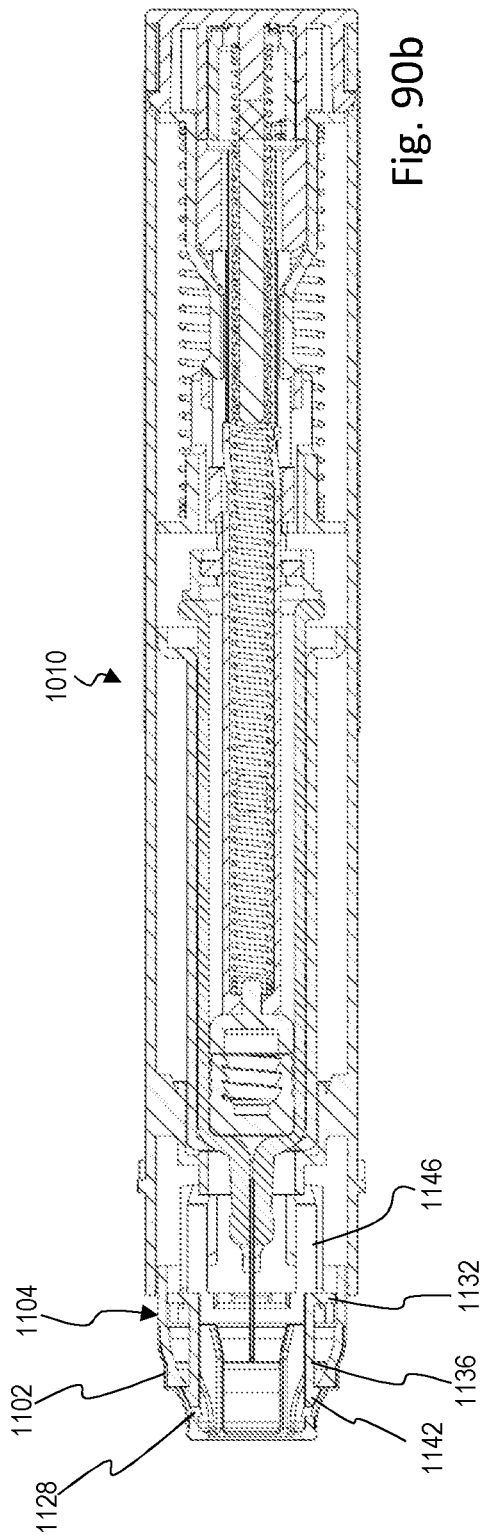
Figure 90C:
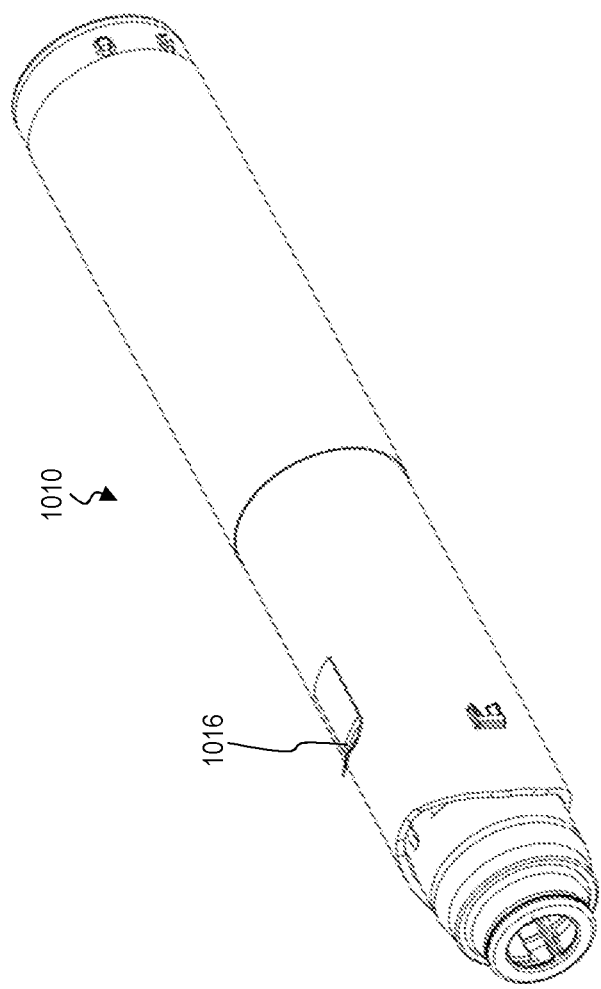

FIG. 3 an exploded view of the drug delivery device according to FIG. 1 showing subassemblies thereof, in particular the prefilled syringe;

FIG. 4 is an exploded view of the drug delivery device according to FIG. 1 showing subassemblies thereof, in particular a trigger element, a trigger spring, a shield retention indicator, a plunger and a power spring, a retainer, a shield retention indicator inner, and a distal end cap;

FIGS. 5 to 7 show different perspective views of a cap housing and FIGS. 8 and 9 show different perspective views of a cap insert;

FIGS. 10 to 13 show different perspective views of examples of a needle shield gripper;

FIGS. 14 to 18 show different views of the safety shield;

FIGS. 19 to 22 show different views of the longitudinal housing;

FIGS. 23 and 24 show perspective views of a syringe holder;

FIG. 25 shows the assembled prefilled syringe;

FIGS. 26 and 27 show an exploded perspective views of a rigid needle shield and an insert thereof;

FIG. 28 shows a perspective view of the syringe body;

FIG. 29 is a perspective view of the stopper;

FIGS. 30 to 33 are different views of the trigger element;

FIGS. 34 and 35 show different perspective views of the shield retention indicator;

FIGS. 36 and 37 are perspective views of a plunger;

FIG. 38 is a perspective view of the shield retention indicator inner;

FIGS. 39 to 41 are different views of the retainer;

FIGS. 42 and 43 are different perspective views of the a distal end cap;

FIGS. 44a to 44d is a side view (FIG. 44a) and different longitudinal sectional views of the device according to the invention in an initial state, wherein FIG. 44b is a longitudinal sectional view rotated by 90° relative to FIG. 44a, FIG. 44c is a longitudinal sectional view rotated by 180° relative to FIG. 44a, and FIG. 44d is a longitudinal sectional view rotated by 45° relative to FIG. 44a;

FIGS. 45a to 45d are views according to FIGS. 44a to 44d in a condition in which the removable cap is partially twisted-off from the longitudinal housing;

FIGS. 46a to 46d are views according to FIGS. 44a to 44d in a condition in which the removable cap is entirely removed from the longitudinal housing and the device is ready for dispensing the fluid product;

FIGS. 47a to 47d are views according to FIGS. 44a to 44d in a condition in which the device already pressed against a patient's skin, wherein the safety shield is partially pressed into the longitudinal housing;

FIGS. 48a to 48d are views according to FIGS. 44a to 44d in a condition in which the device is pressed against a patient's skin, wherein the injection needle is pierced into the patient's skin, the safety shield is fully depressed into the longitudinal housing and dispensing of the fluid product is initiated;

FIGS. 49a to 49d are views according to FIGS. 44a to 44d in a condition in which the fluid product is being partially dispensed;

FIGS. 50a to 50d are views according to FIGS. 44a to 44d in a condition in which the fluid product is being nearly entirely dispensed, wherein indicating mechanism is triggered;

FIGS. 51a to 51d are views according to FIGS. 44a to 44d in a condition in which the fluid indicator reaches its final position;

FIGS. 52a to 52d are views according to FIGS. 44a to 44d in a condition in which the fluid product is fully dispensed;

FIGS. 53a to 53d are views according to FIGS. 44a to 44d in a condition in which the device is in the process of being removed from the injection site on the patient's skin, wherein the needle is partially retracted out of the patient's tissue and the safety shield is partially released;

FIGS. 54a to 54d are views according to FIGS. 44a to 44d in a condition in which the device is in the process of being removed from the injection site on the patient's skin, wherein the needle is entirely retracted out of the patient's tissue and the safety shield is further released;

FIGS. 55a to 55d are views according to FIGS. 44a to 44d in a condition in which the device is entirely removed from the injection site on the patient's skin, wherein the needle is entirely retracted out of the patient's tissue and the safety shield is fully released;

FIGS. 56a to 56d are views according to FIGS. 44a to 44d in a condition in which the device is entirely removed from the injection site on the patient's skin, wherein the safety shield is blocked against a further axial depression;

FIGS. 57 to 60 are different views of further examples of syringe holders;

FIG. 61 is a perspective view of a different drug delivery device in an assembled state;

FIG. 62 is an exploded view of the drug delivery device according to FIG. 1 showing subassemblies thereof;

FIG. 63 is an exploded view showing the components of a syringe unit subassembly including a front cap according to FIG. 62;

FIG. 64 is an exploded view showing the components of a syringe subassembly according to FIG. 62;

FIG. 65 is an exploded view showing the components of a power pack subassembly according to FIG. 62;

FIGS. 66a and 66b are different perspective views of a distal end cap body;

FIG. 67 is a perspective view of a distal end cap cover;

FIG. 68 is a perspective view of a blade washer;

FIGS. 69a and 69b are perspective views of a safety shield of the syringe unit subassembly;

FIG. 70 is a perspective view of a safety shield indicator;

FIGS. 71a and 71b are perspective views of a lock ring of the syringe unit subassembly;

FIGS. 72a and 72b are perspective views of a syringe holder of the syringe unit subassembly;

FIGS. 73a and 73b are perspective views of a housing of the syringe unit subassembly;

FIG. 73c is a side view of the housing of the syringe unit subassembly from the right showing the inner structure;

FIG. 74 is a perspective side view of a rigid needle shield;

FIG. 75 is a perspective side view of a needle receiving insert for the rigid needle shield;

FIG. 76 is a perspective view of a glass body including a needle;

FIG. 77 is a perspective view of a stopper;

FIGS. 78a and 78b are different perspective views of a plunger rod of the power-pack subassembly;

FIGS. 79a and 79b are perspective views of a shield retention trigger of the power-pack subassembly;

FIGS. 80a and 80b are perspective views of a shield retention indicator of the power-pack subassembly;

FIGS. 81a and 81b are perspective views of a retainer of the power-pack subassembly;

FIGS. 82a and 82b are perspective views of a rotary click element of the power-pack subassembly;

FIGS. 83a and 83b are perspective views of a snap-fit distal end cap of the power-pack subassembly;

FIGS. 84a and 84b show a drug delivery device in a ready to use state, wherein FIG. 84a shows a side view and FIG. 84b shows a longitudinal sectional view;

FIGS. 85a and 85b are longitudinal sectional views of the drug delivery device in a state where the end cap has just been removed, wherein FIG. 85a is the longitudinal section along plane A indicated in FIG. 61 and wherein FIG. 85b is the longitudinal section along plane B indicated in FIG. 61;

FIGS. 86a and 86b are longitudinal sectional views according to FIGS. 85a and 85b in a state, when the drug delivery device is fully pressed against the patient's skin and the drug delivery is just started;

FIGS. 87*a* and 87*b* are longitudinal sectional views according to FIGS. 85*a* and 85*b* in an intermediate state, when the drug delivery device delivers the drug to the patient;

FIGS. 88*a* and 88*b* are longitudinal sectional views according to FIGS. 85*a* and 85*b* in an intermediate state, when the drug delivery is close to an end;

FIGS. 89*a* and 89*b* are longitudinal sectional views according to FIGS. 85*a* and 85*b* in a state, when the drug delivery device has fully delivered the drug to the patient;

FIGS. 90*a* and 90*b* are longitudinal sectional views according to FIGS. 85*a* and 85*b* in a state, when the drug delivery device is removed from the patient's skin and secured in a locked state after use; and FIG. 90*c* is a perspective view of the drug delivery device in the locked state after use.

FIG. 1*a* shows an automatic mechanical drug delivery device 10, formed as an auto-injector, according to the invention in a perspective side view. The device 10 comprises a longitudinal body 12 extending along an axis X and a removable end cap 50 at the proximal end of the device 10. The end of the device 10 to which the removable end cap 50 is located is called within this description the proximal end, which will be in contact with the patient. The opposite end, in FIG. 1 on the right side is called the distal end within this description.

FIG. 1 furthermore schematically shows two different view directions A, B, C and D representing views (top view A) and planes of longitudinal sections B, C and D. In the following, when describing the structure and the operation of the device 10, it is referred to these particular views A and planes of longitudinal sections B, C, D.

FIGS. 2, 3 and 4 show subassemblies 100, 200 and 300 of the device 10. In FIG. 2, one can see the proximal subassembly 100 including the end cap 50. In FIG. 3, one can see a subassembly including a prefilled syringe unit 200. In FIG. 4, one can see a power-pack subassembly 300. These three subassemblies 100, 200 and 300 are provided as separate pre-assembled modules when assembling the device 10 according to the invention. This allows to pre-assemble the syringe unit 200 and the power-pack 300 and to provide a corresponding prefilled syringe 204 with a demanded medicament provided therein in a sealed manner and with the predetermined volume for drug delivery.

As will be seen in the following, the three subassemblies 100, 200 and 300 can be assembled to the device 10 by plugging the prefilled syringe 200 into the receiving syringe unit 100 and thereafter plugging the power-pack 300 from the right side, i.e. distal side, into the open distal end of the body 12 of the syringe unit 100 until it locks into a predetermined non-separable position. By this modular structure, the device according to the invention can be easily assembled in an error-free manner.

It is to be noted that although in the following a particular example of the device 10 is described in its structure and functioning in regard to the figures, the components of the device 10 as described in the following can be used also independently from the respective structure. In particular, each of the three subassemblies 100, 200 and 300 and the components thereof can be used separately and independently from the other subassemblies. For example the proximal subassembly 100 and its components can be used separately in another autoinjector, independent from the specific design of the syringe unit 200 or the power-pack 300. Therefore, the following description is not to be understood as a limiting disclosure in a way that each and every component can only be used together with the further components described in the following context. Instead, the present disclosure is to be understood in a way that each and every component disclosed therein can be claimed with its respective features separately independent from the interacting components of the respective subassemblies.

In the following the components of the subassemblies are described in detail.

FIG. 2 shows an exploded view of the proximal subassembly 100. This proximal subassembly 100 comprises the removable end cap 50 formed by an end cap body 52, a blade washer 54 and a proximal end cap cover 56. Moreover, the proximal subassembly 100 comprises a safety shield 102, a longitudinal housing 104 and a syringe holder 106. These components will be described in detail in regard to FIGS. 4 to 24 in the following.

FIG. 3 shows an exploded view of the components of the subassembly forming the prefilled syringe 200. This syringe subassembly 200 includes a rigid needle shield 202 with an insert 207, a glass body 204 with an integrally provided needle 206, a medicament 208 shown as a liquid column and a stopper 210. These components of the prefilled syringe 200 will be described in detail in regard to FIGS. 25 to 29.

FIG. 4 shows an exploded view of the components of the subassembly forming the power-pack 300. This power-pack subassembly 300 includes a trigger element 302, a trigger spring 304, a shield retention indicator 306, a plunger 308, a drive spring 310, a retainer 312, a shield retention indicator inner element 314 and a distal end cap 316. These components will be described in detail in regard to FIGS. 30 to 43 in the following.

FIGS. 5 to 7 show the removable end cap body 52 from different perspective views. One can see the cylindrical body 58 integrally formed with an arch-like extension 60 such that the cylindrical body 58 forms a non-circular circumference providing an anti-roll shape when the end cap is placed on a flat or slightly inclined surface. The outer circumferential surface of the body 58 has a number of integrally formed radial gripping recesses 62 extending in a longitudinal direction between the proximal and distal ends of the body 58. The proximal part of the body 58 is formed by a smooth outer surface 64. This surface includes arrow-shaped surface offsets 66 which indicate the direction of movement for twisting-on or twisting-off the end cap 50 relative to the longitudinal housing 12.

In its interior, the end cap body 52 includes a circular cylindrical surface 68 forming an axially open receiving portion 70 with a smooth receiving surface. Next to the receiving portion 70 there is an integrally formed ring 72 portion. The ring portion 72 includes a substantially flat cylindrical upper front surface 74 faced in distal direction. Between the ring portion 72 and the inner circumferential surface 68 of the end cap body 52, there is an open gap 75 and a connecting structure 76 connecting both components. The ring portion 72 provides on its outer circumferential surface two projections 78 extending in radial outward direction into the gap 74. On both sides of the projections 78, the outer circumferential surface of the ring portion 72 is provided with inclined lifting formations 80 and 82 which have the most distal level close to the projections 78 and which are inclined in distal direction to meet on an apex 84.

As one can see in FIG. 6 right below each projection 78, the outer circumferential surface of the ring portion 72 has two chamfered projections 86 and 88, which form a receiving space 90 there between. This receiving space 90 is provided to receive and secure a projection 198 formed on the inner circumferential surface the longitudinal housing 104 on its proximal end, as will be described in regard to FIGS. 19 and 20.

On its radial inner surface, the ring body 72 includes two opposite projections 92, protruding radial inwards. These two projections 92 are provided for interacting with and securing corresponding radial outward projections 156 formed on the outer circumferential surface of the proximal end of the safety shield 102, as will be described in regard to FIGS. 14 to 18.

Focusing on FIG. 6, one can see that the end cap body 52 close to its proximal end is faced with two annular arches 94 arranged in opposite relation and fixed to the inner circumferential surface 68 of the end cap body 52 by means of a connection portion 96 and connecting ribs 98.

FIGS. 8 and 9 show the end cap cover 56. The end cap cover 56 has a proximal end cap portion 110 having the same basic surface with a slightly inclined projection 112 as the end cap body 52. An annular cylindrical body 114 extends from the proximal surface of the end cap portion 110. The annular cylindrical body 114 is provided on its outer circumferential surface 116 with a plurality of longitudinal ribs 118 which protrude over the distal end of the annular cylindrical body 114. At the free end of these longitudinal ribs 118, snap fit projections protruding radially outwardly can be provided, as far as necessary, which engage into a corresponding (annular) recess within the end cap body 52. In its interior the annular cylindrical body 114 is provided with chamfered radially extending ribs 120 running into an inner cylindrical body 122, which is also integrally formed with the distal surface of the end cap portion 110. The distal front surface of the arrangement formed by the cylindrical body 114, the projections of the ribs 118, the radially inner ribs 120 and the inner cylindrical body 122 form a conical profile.

FIGS. 10 to 13 show two different examples of the blade washer 54. The blade washer 54 has a circular outer circumference 130 surrounding a ring-shaped body 132. The blade washer 54 includes four radially inwardly extending lobes 134 integrally formed with the ring-shaped body 132 and ending in a circular radially inner gripping surface 136. In a side view, one can see that the blade washer 54 according to the example shown in FIGS. 10 and 11 is flat, whereas the blade washer 54 according to the example shown in FIGS. 12 and 13 has a frustoconical shape. In both examples the lobes 84 provide an axial spring action, i.e. the lobes 84 can be deflected elastically in axial direction.

In an assembled state of the end cap 50, the blade washer 54 is arranged on the proximal surface of the annular arches 94. The end cap cover 56 is pressed into the proximal end of the end cap body 52, whereby the protruding ends of the ribs 118 engage the ring-shaped body 132 of the blade washer 54 and presses it (as an optional feature) against the annular arches 94. The blade washer 54 is thereby fixedly held and biased, or it is arranged alternatively with some axial clearance, between the proximal front surface of the annular arches 94 and the conical structure formed on the distal side of the end cap cover 56. The conical structure formed on the distal side of the end cap cover 56 provides sufficient distance to the lobes 84 such that the lobes can flex proximally in axial direction within this assembly.

As an optional feature, one or two lobes 134 can have a different length than the other lobes 134 such that when engaging the rigid needle shield 202, there is asymmetric force load-balancing on the rigid needle shield 202. This leads to a tilting or turning action such that the rigid needle shield 202 is deflected from its original position. Thereby, recapping, i.e. re-plugging the cap 50 onto the housing once it has been removed, can be avoided.

FIGS. 14 to 18 show the safety shield 102 in different perspective views. The safety shield 102 includes a ring-shaped hollow cylindrical body 150 at its proximal end with two diametrically opposing longitudinal arms 152, 154. This arrangement of the body 150 and the longitudinal arms 152, 154 can be integrally formed or formed from separate pieces, i.e. the cylindrical body may include a separate cover which can be formed from a coloured material.

The ring-shaped body 150 has two projections 156 close to its distal end. The distal end of the ring-shaped body 150 is provided with an annular collar 158 having a rounded outer circumferential ring 160 with two opposite slots 162. A longitudinal hollow portion 164 extends from this annular collar 158 in distal direction, divided by the slots 162 in two separate halves. The two longitudinal arms 152, 154 are integrally formed with the distal end of the collar 158 and have a stepped course, such that a first transition 166 between the collar 158 and a first longitudinal arm portion 168 forms a first shoulder and wherein a second transition 170 between the first longitudinal arm portion 168 and a second longitudinal arm portion 172 forms a second inclined shoulder. Each of the second longitudinal arm portions 172 has on its outer circumferential surface a projection 174 protruding radially outwards and having a sharp radial surface facing in proximal direction and an inclined chamfered surface facing in distal direction. In line with the projection 174 the longitudinal arm portion 172 has a rectangle a through hole 176 close to its distal end.

The inner circumferential surface at the distal end of each second longitudinal arm portion 172 includes an inner guiding profile 178. Moreover, the inner circumferential surface of the cylindrical body 150 includes four guiding ribs 180 protruding radially inwards. These inner guiding ribs 180 are provided for guiding the rigid needle shield 202.

The cylindrical body 150 is smoothly formed and radiused on its front (proximal) end such that it does not injure or scrape on the patient's skin. As mentioned above, the cylindrical body 150 together with the longitudinal arms 152, 154 can be a single-piece arrangement or a multi-piece assembly.

FIGS. 19 to 22 show the housing 104 in different views. The housing 104 has the purpose of forming the main body 12 of the device 10. It is formed from a stable, rigid, transparent or opaque material. If not entirely transparent, the housing can be formed with drug viewing cutouts or transparent windows in order to make the drug, and the state of the device visible to a user. The housing 104 is formed by a longitudinal tubular member 190. At its proximal end, the tubular member 190 is provided with a hollow cylindrical portion 192 having a circular cross-section and a front surface 194. In a distance from the proximal end, the longitudinal member 190 is provided with a rounded hollow extension 196 having the same shape and cross-section as the extension 60 of the removable cap, in order to provide a geometry with an anti-roll function on a flat surface. At the proximal end, the cylindrical portion 192 is provided on its circumferential inner surface with two rib-like opposing projections 198, protruding radially inwards, which are thereby hidden to the outside and which are adapted to interact with the removable and cap 50. Moreover, in its middle section, the housing 104 is provided with two opposing longitudinal through holes 220, having the function of guiding slots. As an alternative, these through holes 220 can be replaced by guiding channels which open to the inside of the housing 104, but which are closed on the outer circumferential surface thereof. In line with the guiding slots 220 but closer to the distal end, the housing is provided with two further opposing through holes 222, which as an alternative can be also provided as internal recesses which are closed at the outer circumferential surface. Close to its distal end, the housing 104 is provided with a pair of opposing transverse through holes 224, which as an alternative can be also provided as internal recesses which are closed at the outer circumferential surface. The distal end is further provided with a distal front surface 226, which has two opposing short notches 228.

In its interior, the housing 104 is provided with a double-ring structure 230, which is integrally connected to the tubular member 190 in the region of the cylindrical portion 192 by means of pair of opposing rigid connecting arms 232. The connecting arms 232 are formed by a stable U-shaped structure with two lateral longitudinal connecting ribs 234 and one transverse connecting rib 236 running in circumferential direction. The size of the connecting ribs and the U-shaped sectional shape are to provide structural rigidity to the housing 104. This joining geometry is also important for the flow of the material when the component is molded.

Moreover, the double-ring structure 230 has an outer ring 238 running with a conical transition portion 240 into a hollow inner ring 242. To the proximal end, two strengthening ribs 244 stabilize the connection between the outer ring 238 and the inner ring 242. Faced to the distal end, the conical transition portion 240 is provided with two opposing cutouts 246 and one rib-like axial projection 248. The arrangement of the two opposing cutouts 246 and the axial projection 248 are provided for positioning the prefilled syringe 200 in connection with the syringe holder 106. For some variants projection 248 may or may not be included.

FIGS. 23 and 24 show one example for the syringe holder 106. Other examples of the syringe holder are described in regard to FIGS. 57 to 60.

The syringe holder 106 has the purpose to receive and hold the prefilled syringe 204 within the housing 104. It is adapted to receive different kinds of syringes with different volumes of medicament without the need of changing the dimensions of other components of the device 10. Therefore, different sizes for syringe holders 106 are to be provided in adaptation to the different kinds/volumes of syringes.

The syringe holder 106 provides a longitudinal body 260. At its proximal end, the syringe holder 106 is formed with a rigid and non-elastic U-shaped element 262, which is open in one radial direction, as can be seen in FIG. 23. This rigid U-shaped element 262 at the proximal end is reinforced by two parallel surrounding ribs 264, 266. At the proximal front surface, the U-shaped element 262 is provided with two transverse ribs or projections 268. At its distal end, the syringe holder 106 is provided with a rigid and non-elastic similar U-shaped element 270, reinforced with two parallel surrounding ribs 272, 274. The two surrounding ribs 272, 274 are provided with cutouts 276, 278, facing radially outwards on opposite positions. The two rigid U-shaped elements 262 and 272 are connected by two longitudinal and rigid connecting arms 280, 282. Each of the connecting arms extends in a straight manner and includes in its middle section in FIG. 23 on the upper end a projection 284, 286 projecting radially inwards such that they are faced to one another. The inner surface 288 of the projections 284, 286 is rounded, as can be seen in FIGS. 23 and 24, such that a glass body of the syringe 200 can be arranged and held therein.

When placed within the longitudinal housing 104, the syringe holder 106 holding a prefilled syringe 200, preferably in the rotational manner, is positioned such that the two projections 268 engage into the cutouts 246 of the double-ring structure 230 and the projection 248 engages into the hollow space provided by the proximal U-shaped element 262. Thereby, the syringe holder 106 is positioned by the double-ring structure 230 within the longitudinal housing 104 in an appropriate axial and rotational position around the longitudinal axis.

FIG. 25 shows the prefilled syringe 200 in an assembled state, wherein the rigid needle shield 202 is placed on the proximal front end of the syringe covering the injection needle 206.

FIGS. 26 and 27 show perspective views of the rigid needle shield 202 with the insert 207. The rigid needle shield 202 is formed by a tubular member 320 with an open distal end 322 and a closed proximal end 324. In its front portion it has a surface formed with transverse gripping ribs 326. Close to its distal end, it has two opposite rectangular through holes 328.

The insert 207 is formed by a soft deformable material and can be pressed into the rigid needle shield 202 such that it is fixedly held therein. It has an annular collar 330 close to its distal end which engages with the rectangular through holes 328 of the rigid needle shield 202.

FIG. 28 shows the syringe 204. The syringe 204 is formed by a hollow cylindrical glass body 332 having an open distal end 334, which is surrounded by a circumferential annular collar 336 with two flattened opposite side surfaces 338. At its proximal portion, the cylindrical glass body 332 is formed with a rounded taper 340 and transits into a hollow conical glass portion 342 ending in a stepped needle hub 344 with a spherical or rounded proximal head 346. The proximal head 346 fixedly holds said injection needle 206 with a sharpened needle tip 348.

FIG. 29 shows the stopper element 210 formed from a flexible material, e.g. a rubber. At its proximal portion, it has a smooth cylindrical outer circumferential surface 350, which has a diameter adapted to the inner diameter of the hollow cylindrical glass body 332 of the syringe 204 such that the stopper element 210 slidably engages the inner circumferential surface of the hollow cylindrical glass body 332 in a fluid tight manner. On the distal portion of the outer surface, the stopper element 210 is provided with four circumferential annular recesses forming three circumferential sealing ribs 352. The stopper element 210 has cup-shape with a closed proximal end 354 and an open distal end 356.

Turning now to the components of the power-pack or drive assembly, FIGS. 30 to 33 show the trigger element 302 in different views. The trigger element is formed by a tube-shaped hollow body 360. At its proximal end it has a front surface 362 surrounded by a chamfered rim 363 and provided with two opposite lateral tabs 364, 366 extending in radial direction. From the front surface 362 of these lateral tabs 364, 366 two rectangular projection plates 368, 370 extend in longitudinal axial direction. The projection plates 368, 370 are provided with chamfered projections 372, extending radially outwardly. The tube shaped hollow body 360 extends in distal direction and provides in its middle portion a surrounding annular reinforcement rib 374 connected to the reinforced proximal end by longitudinal ribs 376. Moreover, between the proximal end 362 and the reinforcement rib 374, two opposing rectangular hollow box elements 378 or recesses formed by other wall structures are provided at the outer circumferential surface of the trigger element 302, wherein these box elements 378 or recesses provide a hollow space 379, respectively, in which additional components, e.g. electronic sensors or the like can be provided.

Further in distal direction, the outer circumferential surface of the tubular hollow body 360 is provided with a further annular and circumferential reinforcement rib 380, having an L-shaped profile to support the spring 304. The distal end of the tubular hollow body 360 of the trigger element 302 is formed by a hollow cylindrical portion 382 having a front surface 384. In its interior, the trigger element 302 is provided with four longitudinal guiding ribs 386, wherein two pairs of these guiding ribs 386 are connected by an arch-like connecting rib 388, respectively, which extends in circumferential direction along the inner circumferential surface of the tubular hollow body 360.

FIGS. 34 and 35 show the shield retention indicator 306. The shield retention indicator 306 is formed by a hollow cylindrical body 400 having an annular cylindrical component 402, which is extended by a rounded extension 404 adapted to the geometry of the housing 104. It is receivable in a slidable but form-fitting manner within the extended portion 196 of the hollow cylindrical body 190 of the longitudinal housing 190. It has a smooth outer circumferential surface 406. At its proximal end, the shield retention indicator 306 is provided with four longitudinal flexible arms 408, each having a proximal free end 410. The free ends 410 of the flexible arms 408 are provided with protrusions 412 extending radially inwardly and reinforced by short longitudinal chamfered ribs 414. The distal end of the shield retention indicator 306 is provided with a circular opening 416.

The circumferential outer surface 406 of the shield retention indicator 306 has a signalling colour, i.e. yellow, orange or red, or a signalling pattern which is clearly visible by a user. Thereby, as will be discussed in detail in regard to the operation of the drug delivery device 10 according to the present invention, the user, i.e. the medical practitioner or the patient, of the device 10 can easily recognize when the shield retention indicator 306 is moved into a signalling position in which it is clearly visible through the longitudinal housing 104 from the outside.

FIGS. 36 and 37 depict the plunger 308 in different perspective views. The plunger 308 is formed by a longitudinal pipe-shaped hollow element 420 which has at its proximal end a plunger head 422. The plunger head 422 is provided with a front surface 424 and a transverse slot 426. The front surface 424 includes a small cylindrical through hole 428. The front surface with the transverse slot 426 and the cylindrical through hole 428 can be coupled with an additional plunger head element, if needed e.g. for syringes having a larger inner diameter interacting with a correspondingly large stopper 210. This additional enlarged plunger head can be used for larger syringes, e.g. having a drug volume of 2.25 ml. In case of smaller syringes, as shown in the example, e.g. syringes having a drug volume of 1 ml, the enlarged plunger head is omitted and the plunger 308 has just straight cylindrical shape on its proximal end.

In the middle portion of the plunger 308, a pair of opposing rectangular through holes 430 is provided in the wall of the hollow element 420. According to another example, the plunger may have additional pairs of through holes, comparable to the through holes 430, which allow an adaptation to different syringe sizes or filling volumes of the drug. At the distal end, the hollow element 420 is provided with a circular opening 432 providing access in longitudinal direction for receiving the drive spring 310.

FIG. 38 shows the shield retention indicator inner element 314. This element is formed by a stepped tubular body 440 having a first hollow cylindrical portion 442 with a smaller diameter and an enlarged second hollow cylindrical portion 444 with a larger diameter. At its proximal end, the shield retention indicator inner element 314 is provided with two opposing flexible longitudinal arms 446 extending in proximal direction, wherein a first portion 448 runs in longitudinal direction, a second portion 450 is slightly inclined radially inwards, and a third portion 452 extends in longitudinal direction, however, on a radial level which is further radially inwards than the first portion 448. At its proximal end, each of the arms 446 has an inclined retaining projection 454 extending radially outwards.

The distal portion of the shield retention indicator inner element 314 is provided with an end plate 456 having the same rounded and extended cross-sectional surface as the distal end of the shield retention indicator 306. The diameter of the outer circumferential surface of the second hollow cylindrical portion 444 is adapted to be received within the circular opening 416 provided in the distal end of the shield retention indicator 306.

FIGS. 39 to 41 depict the retainer 312 of the power-pack 300 or drive assembly. The retainer 312 acts as the control member including a plurality of control functions of the power-pack 300. The retainer 312 is formed from a hollow cylindrical body 470. On two opposing sides the cylindrical body 470 includes a U-shaped cutout 472 forming a longitudinal flexible arm 474, respectively. The longitudinal flexible arm 474 is integrally connected to the hollow cylindrical body 470 at its distal end 476. At its proximal end, the flexible arm 474 is provided with a chamfered radial outward projection 478 and, on the opposite side, i.e. on its radial inner side, with a corresponding chamfered radial inward projection 480. Moreover, the cylindrical body 470 is provided with two opposing longitudinal cutouts 482 in an area rotated by 90° relative to the flexible arms 474 formed by the cutouts 472. The longitudinal cutouts 482 extend approximately with the same longitudinal extension as the U-shaped cutout 472, however slightly farther in distal direction. In the region of about one third of the longitudinal length of the cutouts 482 close to their proximal end, the cylindrical body 470 comprises lateral projections 484 transversely bridging the cutouts 482. These lateral bridging projections 484 are continued close to the proximal end by additional projections 486 having the same outer circumferential shape.

At its proximal end, the cylindrical body 470 is provided with two flexible arms 490 integrally formed with the cylindrical body 470 and inclined by an angle of about 45° relative to the proximal front surface of the hollow cylindrical body 470. These flexible arms 490 are connected to a ring-shaped head portion 492. The ring-shaped head portion 492 is formed as a bushing with a cylindrical portion 494 and two opposing proximal arch-like projections 496. The head portion 492 can be integrally formed with the flexible arms 490 or formed as a separate piece fixedly connected to the flexible arms 490, e.g. by means of an intermediate connecting ring.

At its distal end, the cylindrical body 470 is formed with a circumferential groove 500. The distal end is provided with a distal end surface 502 having a central opening 504. In its interior close to the distal end, the cylindrical body 470 is provided with inner guiding ribs 498 running in axial or longitudinal direction between the distal end surface 502 and the longitudinal section having the circumferential groove 500.

FIGS. 42 and 43 depict the distal end cap 316 of the device 10. The distal end cap 316 has a distal end cap body 510 having the same cross-sectional profile as the distal end of the longitudinal housing 104, i.e. rounded with an extension. The distal end cap body 510 is formed from a transparent material and closed by a distal surface 512. A transition 516 between the circumferential surface 514 and the distal surface 512 is rounded or chamfered. At its proximal end, the distal end cap 316 is provided with a plug-in portion 520, which is form-fittingly received in an assembled state within the distal end of the longitudinal housing 104. Therefore, the plug-in portion 520 has a reduced outer diameter and transits to the distal end cap body 510 via a step surface 522.

In the region of the step surface 522 the distal end cap 316 provides longitudinal protrusions 524 corresponding to the notches 228 described in regard to FIGS. 19 to 22 for the longitudinal housing 104. By interaction of the protrusions 524 and the notches 228, the distal end cap 316 is positioned relative to the longitudinal housing 104. Moreover, the plug-in portion 520 provides two longitudinal projections 526 on the proximal end. The outer circumferential surface of these longitudinal projections 526 is formed with chamfered snap-fit projections 528, respectively. These projections 528 are provided to engage in a snap-fit manner with the corresponding through holes 224 provided in the longitudinal housing 104 when assembling the device.

It is to be mentioned that the snap-fit engagement between the projections 528 and the through holes 224—once assembled—is not separable. The device according to the present invention is a single use device and excludes that the distal end cap 316, after having been fixed to the longitudinal housing 104, is removed from the housing 104 again. It is not provided or intended to replace or refill the syringe 200 after use or to provide any other access to the interior and the components of the device 10, once it has been used.

Turning to the interior of the distal end cap 316, one can see in FIG. 43 that the end cap is provided with a hollow cylindrical body 530 integrally formed with a bottom surface 532 of the distal end cap 316.

In the following, the assembled state of the device 10 is described in regard to FIGS. 44a and 44d. FIGS. 44a shows a side view and FIGS. 44b to 44d show different longitudinal sectional views of the device according to the invention in an initial state, wherein FIG. 44b is a longitudinal sectional view rotated by 90° relative to FIG. 44a, FIG. 44c is a longitudinal sectional view rotated by 180° relative to FIG. 44a, and FIG. 44d is a longitudinal sectional view rotated by 45° relative to FIG. 44a. Reference is made to the planes and arrows A, B, C, D depicted in FIG. 1. The shown state is also the initial state of the device 10, i.e. the state of the device how it is delivered to the user.

In the assembled or initial state of the device 10, the end cap 50 is screwed onto the longitudinal housing 104, wherein the end cap 50 is held in circumferential direction by an engagement of each of the inner protrusions 198 formed on the proximal end of the housing 104 within a corresponding receiving space 90 between the two projections 86 and 88 formed inside the end cap body 52. Moreover, the end cap 50 is held in longitudinal direction by an engagement of each of the inner protrusions 198 formed in the proximal end of the housing 104 located behind the projections 78 formed on the inner ring portion 72 of the end cap body 52, respectively. Thereby, the removable cap 50 is held on the housing against an axial withdrawing force by the projections 78 as well as against small twist-off forces, which are below a twist-off force threshold value, by the opposing projections 86 and 88 forming the receiving space 90.

Moreover, the safety shield 102 is held in the assembled initial state according to FIGS. 44a to 44d by the removable cap 50 in the axial position shown in FIGS. 44b to 44d. In particular this has the purpose to avoid unintended movement in distal direction, i.e. if the device 10 is dropped and experiences a shock when it falls on the ground. This is achieved by an engagement between the projections 156 formed on the outer circumferential surface of the cylindrical body 150 at the proximal end of the safety shield 102 and the two projections 92 formed on the inner circumferential surface of the inner ring portion 72 of the removable cap body 52. Thereby, the projections 92 block any axial movement of the safety shield 102 in distal direction relative to the removable cap 50 mounted to the housing 104 and thereby relative to the housing 104.

At the distal end, the distal end cap 316 is fixedly and inseparably attached by the snap-fit arrangement to the longitudinal housing 104, wherein the projections 526 formed on the outer circumferential surface of the plug-in portion 520 of the distal end cap 316 engage into the through holes 224 formed on the distal end of the housing 104.

Moreover, in the assembled state, the syringe 204 is held within the syringe holder 106, which is received in the ring structure 230 of the housing 104. As described above, the syringe holder is positioned relative to the housing 104 by means of the ring structure 230, wherein the transverse projections 268 engage into the respective cutouts 246 and the projection 248 projects into the hollow space provided by the U-shaped element 262 of the syringe holder (see above). The syringe 204 is pressed in axial direction into the syringe holder 106. The U-shaped elements 262 and 272 are rigid and do not flex-out during assembly or during operation. It is to be noted that the syringe 204 is held rotationally within the syringe holder 106.

Moreover, the syringe 204 together with the syringe holder 106 are pressed via the syringe flange 336 by means of the head portion 494 of the retainer 312 in proximal direction against the conical and stepped ring structure 230 of the housing 104, wherein the flexible arms 490 of the retainer act as axial spring means providing a spring force in axial proximal direction in order to hold the syringe 204 in place within the syringe holder 106 and positioned thereby. The rigid needle shield 202 engages the hollow conical glass portion 344 by means of the insert 207. The soft insert 207 safely covers the needle 206 and maintains sterility of the injection needle 206 and the medicament contained within the syringe 204 and the needle 206. As one can see in FIG. 44b, the outer surface of the tubular member 320 with the transverse gripping ribs 326 or as an alternative just with a soft outer surface is engaged by the flexible lobes 134 of the blade washer 54 which has a conical shape in this example. As mentioned above, the flexible lobes 134 can have different radial lengths to provide an unbalanced force onto the rigid needle shield 202. The blade washer 54 is held within the removable end cap 50 by means of the cap cover 56.

Moreover, FIGS. 44b to 44d show the ring-shaped cylindrical body 150 of the safety shield 102. The safety shield 102 is pressed by the end cap 50 via the longitudinal arms 152, 154 against the force of the shield spring 308 in distal direction partially into the housing 104. The trigger element 302 acts as an intermediate element between the longitudinal arms 152, 154 and the shield spring 304. As one can see in FIG. 44c, the trigger element 302 is in the assembled state permanently coupled via its projection plates 368, 370 with the distal ends of the arms 152, 154 of the safety shield 102. The projection plates 368, 370 are received within the inner guiding profile 178 at the distal end of the arms 152, 154. Moreover, the chamfered projections 372 engage into the through holes 176, respectively, and thereby prevent in the assembled state that the arms 152, 154 of the safety shield 102 are separated under an axial force from the projection plates 368, 370 of the trigger element 302. The chambers of the projections 372 and a guiding profile 178 of the distal end of the arms 152, 154 facilitate the assembling process.

The proximal end of the shield spring 304 engages against the distal portion 382 of the trigger element 302 and abuts against the circumferential rib 380 of the trigger element 302, wherein circumferential rib 380 having an L-shaped profile holds tightly the proximal end of the shield spring 304. The distal end of the shield spring 304 presses via the distal end of the shield retention indicator 306 against the flanged proximal surface of the plate 456 of the shield retention indicator inner element 314.

Furthermore, the shield retention indicator 306 with its cylindrical body 406 receives and surrounds the shield retention indicator inner element 314 as well as the shield spring 308. The four longitudinal arms 408 of the shield retention indicator 306 extend in proximal direction through the gaps provided between the lateral tabs 364, 366 and the box structures 378, each of them projecting in radial outward direction from the trigger element 302. The four longitudinal arms 408 pass the trigger element 302, such that the protrusions 412 of the arms 408 engage the outer circumferential surface of the retainer 314, as can be seen in FIGS. 44b and 44c.

The retainer 312 is fixedly held within the distal end cap 316 by the hollow cylindrical body 530 gripping with an inner circumferential projection into the outer circumferential groove 500 of the retainer in a form-fitting manner. Thereby, the retainer 312 is fixed within the device 10 against any movement in axial direction as well as against tilting.

The shield retention indicator 306 together with the shield retention indicator inner element 314 are held in the axial position by means of the arms 446 in spite of the compressed shield spring 304 and the resulting axial drive forces. This is achieved due to the fact that the arms 446 reach through the longitudinal cutouts 482 of the retainer 312 and engage with their radial retaining projections 454 behind the lateral projections 484 of the retainer 312 bridging the cutouts 382 of the retainer 312. Moreover, in this state, the outer circumferential surface of the plunger 308 arranged radially inside the arms 446 prevents that the arms 446 flex radially inwards and escape from the holding function on the lateral projections 484.

The plunger 308 retains the main spring 310 in a compressed state, as described in the following. The proximal end of the compressed main spring 310 presses against the proximal end of the plunger 308. One can see that the proximal end 422 of the plunger 308 is slidably received within the hollow glass body 332 of the syringe 204 close to the stopper element 210. Moreover, one can see the medicament 208 as a liquid column included within the syringe 204. The distal end of the main spring 310 protrudes out of the plunger 308 and is received within the hollow interior of the retainer 310 where it is supported against its distal end. The plunger 308 is held in its axial position against the drive force of the main spring 310 due to engagement between the flexible arms 474 with the radial inward projections 480, which engage into the through holes 430 provided in the plunger 308. As noted in the description above it is possible to provide additional through holes 430, or slots, with which the projections 480 engage. The longitudinal position of the projections 480 is fixed within the device and so the longitudinal position of the through holes 430 determined the initial position of the plunger within the device. As shown, the plunger head 422 is reasonably close to the stopper 210, but with a smaller fill volume the stopper 210 may be closer to the proximal end and so further from the plunger head 422. This could lead to an undesirably large impact between the plunger head 422 and the 210. In such cases additional through holes 430 longitudinally offset from the original through holes 430 could be included on the plunger 308 to offset the initial position of the plunger 308. As the flexible arms 474 are kept in position by a contact between their radial outward projections 478 and the inner circumferential surface of the trigger element 302, the flexible arms 474 cannot flex radially outwardly in reaction to the drive force of the compressed main spring 310. Thereby, the plunger 308 is held by the flexible arms and their radial inward projections 480 in place.

From this fully assembled initial position, the device 10 according to this example of the invention is used as follows:

Twisting of the Removable End Cap 50

FIGS. 45a to 45d show views according to FIGS. 44a to 44d in a condition in which the removable cap is partially twisted-off from the longitudinal housing. The removable end cap 50 has been slightly rotated relative to the housing 104. No axial movement has taken place. The relative rotation was performed to such a degree that the engagement between the projections 198 formed inside the proximal end of the housing 104 and the projections 86 and 88 formed on the inner ring portion 72 of the end cap body 52 is dissolved. In order to achieve this, a certain threshold value for the twist-off force must be provided to overcome the engagement between the projections 198 of the housing 104 and the projections 86, 88 of the removable end cap 50. Moreover, the engagement between the projections 156 on the proximal end 150 of the safety shield 102 and the projections 92 on the end cap body 52 is also dissolved during this relative movement. In this state, there is no axial engagement between the removable end cap 50 and the housing 104.

Under further rotation between the removable end cap 50 and the housing 104, the projections 198 are guided along the inclined surfaces of the lifting formations 80, 82. Moreover, during the further relative rotation between the removable end cap 50 and the housing 104 performed by a user by applying the twist-off force, the safety shield 102 is pressed out by the safety shield spring 304 in proximal axial direction. While the safety shield 102 with its proximal portion 150 is pressed out of the longitudinal housing 104, this force supports the removal of the removable end cap 50 and also supports by using the mechanical benefit the relative rotation between the removable end cap 50 and the housing 104. Thus, by experiencing the force provided by the spring 304, the user is guided to further rotate the end cap 50 relative to the housing 104 and to separate the two components from one another.

The proximal portion 150 of the safety shield 102 moving out of the housing 104 covers the needle. The relative movement between the safety shield 102 and the housing 104 is guided by an interaction between the projections 174 formed on each arm 152, 154 of the safety shield and the longitudinal through holes 220, which act as longitudinal guiding channels.

Moreover, during the removal of the end cap 50, the rigid needle shield 202 which is gripped by the lobes 134 of the blade washer 54, is withdrawn together with its insert 207 from the hollow conical glass portion 344 of the syringe 204. Due to the fact that the syringe 204 is rotationally supported within the syringe holder, unwanted coring can be avoided and the syringe is not harmed by the removal of the rigid needle shield 202. Finally the needle 206 with its needle tip 348 is exposed within the ring-shaped proximal body 150 of the safety shield 102.

Removable End Cap 50 Separated from the Housing 102

FIGS. 46a to 46d show views according to FIGS. 44a to 44d in a condition in which the removable cap is entirely removed from the longitudinal housing and the device is ready for dispensing the fluid product. One can see, that the removable end cap 50 is fully separated from the housing 104. The proximal portion 150 of the safety shield 102 fully projects out of the housing 104 and covers the injection needle 206 with its needle tip 348.

Initiating Injection by Pressing the Device Against Patient'S Skin

FIGS. 47a to 47d show views according to FIGS. 44a to 44d in a condition in which the device 10 is already pressed against a patient's skin, wherein the safety shield is partially pressed into the longitudinal housing 104.

As one can see, the proximal front surface of the proximal portion 150 of the safety shield 102 is in contact with the patient's skin S. The device 10 by holding the housing 104 is pressed against the patient's skin S. Thereby, the safety shield 102 is pressed into the housing 104, resulting in a relative movement between these two components. Once again, the projections 174 formed on the arms 152, 154 of the safety shield 102 and engaging into the longitudinal holes 220 of the housing 104 guide the safety shield 102 along its relative linear movement relative to the housing 104.

Due to the movement of the safety shield 102 into the housing 104, the arms 152, 154 press the trigger element 302 in distal direction. Thereby, the trigger element 302 is moved with its chamfered proximal rim 363 under the arms 408 of the shield retention indicator 306. As a consequence, the arms 408 are flexed out, as shown in FIG. 47d.

Starting Dispensing of the Drug by Further Pressing the Device Against Patient's Skin When the device 10 is further being pressed against the patient's skin S, such that the safety shield 102 is further moved in distal direction into the housing 104, the needle 206 is pierced into the patient's skin and finally the situation as shown in FIGS. 48a to 48d is reached. FIGS. 48a to 48d show views according to FIGS. 44a to 44d in a condition in which the device is pressed against a patient's skin, wherein the injection needle is pierced into the patient's skin, the safety shield 102 is fully depressed into the longitudinal housing 104 and dispensing of the fluid product is initiated.

Due to the relative movement between the safety shield 102 and the housing 104, the needle 206 is exposed and protrudes into the patient's skin S. The safety shield 102 is pressed to such an extent into the housing 104, that under compression of the spring 304, it has moved the trigger element 302 with its front surface 362 beyond the projections 478 of the flexible arms 474 of the retainer 314. Under the action of the main spring 310, the plunger 308 is pressed by the surrounding surface of the through holes 430 in axial direction. The surrounding surface of the through holes 430 engaging with the chamfer of the radial inner projections 480 of the flexible arms 474 presses under the force of the main spring 310 the flexible arms 474 of the retainer 312 in radial outward direction. This is possible, as the retainer has moved beyond the outer projections 478 of the flexible arms 474, as shown in FIG. 48c. As a result, the flexible arms 474 flex out and release the plunger 308 for axial movement in proximal direction.

Dispensing the Drug Into the Patient's Tissue

FIGS. 49a to 49d show views according to FIGS. 44a to 44d in a condition in which the fluid product is already partially dispensed. As the plunger 308 is no longer held in axial position by the flexible arms 374 of the retainer 312, the plunger 308 moves in proximal direction, engages the stopper element 210 and presses the stopping element 210 in proximal direction under the action of the main spring 310. Thereby, the drug is pressed out of the glass body 332 of the syringe 204 through the injection needle 206 into the patient's tissue, as indicated by three thin arrows.

This process continues for a full dispensing of the drug into the patient's tissue.

Reaching end of Dispensing Process and Triggering Indicating Mechanism

FIGS. 50a to 50d show views according to FIGS. 44a to 44d in a condition in which the fluid product is being nearly entirely dispensed. In this stage of the device, the indicating mechanism is being triggered. As one can see, the stopper element 210 has nearly reached the proximal bottom surface of the cylindrical glass body 332 of the syringe 204. The plunger 308 has moved correspondingly far in proximal direction under the expansion of the main spring 310. Thereby, the distal end of the plunger 308 has moved in proximal direction beyond the end of the flexible longitudinal arms 446 of the shield retention indicator inner element 314. Thus, the outer circumferential surface of the plunger 308 no longer blocks a radial inward flexing of the longitudinal arms 446.

Due to the compressed state of the spring 304, which is supported via the trigger element 302 against the safety shield 104 and which tends to expand in distal direction, the distal end of the spring 304 presses against the distal end of the shield retention indicator 306 and pushes the combined arrangement of the shield retention indicator 306 together with the shield retention indicator inner element 314 in distal direction. Thereby the longitudinal flexible arms 446 due to the inclined retaining projections 454 are flexed radially inwards and pass the lateral projections 484 bridging the cutouts 482. Thus, the combined arrangement of the shield retention indicator 306 together with the shield retention indicator inner element 314 is free to move in distal direction.

As outlined above, the outer circumferential surface 406 of the shield retention indicator 306 has a signalling colour or pattern. As soon as it enters the transparent region of the distal end cap 316, which is transparent around the whole circumference, the user can see the signalling colour or pattern.

Indicator Reaches Final Position

FIGS. 51a to 51d show views according to FIGS. 44a to 44d in a condition in which the shield retention indicator 306 reaches its final position. One can see, that from the condition according to FIGS. 50a to 50d to the condition according to FIGS. 51a to 51d the shield retention indicator 306 is pressed entirely into the distal end cap 316 under the action of the expanding spring 304.

When reaching the distal inner bottom surface of the end cap 316, the shield retention indicator inner element 314 hits with its endplate 456 the inner bottom surface 532 of the distal end cap 316 and thereby generates an audible and/or tactile signal. This hitting contact achieved under the action of the relaxing spring 304 acts in axial direction and is clearly tangible by the user. Moreover, the sound generated thereby is loud enough to be heard by the user on the normal conditions as a clearly audible click signal. Thus, the user gets a feedback from the device 10 right after achieving the situation close to the end of the fluid dispensing process.

It is to be mentioned, that the spring force of the spring 304 when releasing the combination of the combination of the shield retention indicator 306 together with the shield retention indicator inner element 314 in distal direction is strong enough to initiate this trigger function within a very short period of time, e.g. milliseconds or tenths of a second.

Reaching the End of the Dispensing Process

As mentioned above, the signalling mechanism is triggered shortly before the end of the dispensing process has reached. This is due to the fact that the stopper element 210 has just not reached its end position within the syringe glass body 332, as shown in FIG. 51a, when the signalling mechanism is triggered.

FIGS. 52a to 52d show views according to FIGS. 44a to 44d in a condition in which the fluid product is fully dispensed. In this situation, the stopper element 210 has reached the proximal end of the glass body 332 of the syringe 204. As a consequence, the complete dose of the drug is pressed out of the syringe 204.

Starting Removing the Device 10 from the Patient's Skin

When the dose has been fully dispensed into the patient's tissue, the device 10 can be removed from the injection site. FIGS. 53a to 53d show views according to FIGS. 44a to 44d in a condition in which the device is in the process of being removed from the injection site on the patient's skin, wherein the needle is partially retracted out of the patient's tissue and the safety shield is partially released.

One can see, that the housing 104 of the device 10 has been partially withdrawn from the patient's skin, wherein the proximal front portion 150 of the safety shield 102 is still in contact with the patient's skin S. This is due to the fact that the still compressed spring 304 acts via the trigger element 302 on the longitudinal arms 152, 154 of the safety shield 102 and thereby presses under the action of the compressed spring 304 the safety shield 102 out of the housing 104. Thereby, the injection needle 206, which is retracted together with the housing 104 out of the patient's skin S is permanently covered during this retraction process.

This can be seen in FIGS. 53a to 53d. While retracting the housing 104, the safety shield 102 with its proximal end portion 150 remains in contact with the patient's skin S such that the needle is permanently covered.

Entirely Removing the Device 10 from the Patient's Skin

Finally, the housing 104 has been lifted so far from the patient's skin, that the needle is fully covered by the proximal end portion 150 of the safety shield 102 and the proximal end portion 150 extends beyond the sharpened needle tip 348 of the injection needle. In other words, due to the action of the expanding spring 304, the safety shield 102 is pressed to such an extent out of the housing 104, that it fully covers the needle and protrudes over the needle tip 348.

FIGS. 54a to 54d show views according to FIGS. 44a to 44d in an intermediate condition in which the device is in the process of being removed from the injection site on the patient's skin, wherein the needle is entirely retracted out of the patient's tissue and the safety shield is further released.

FIGS. 55a to 55d show views according to FIGS. 44a to 44d in a condition in which the device is entirely removed from the injection site on the patient's skin, wherein the needle is entirely retracted out of the patient's tissue and the safety shield is fully released. The axial end position of the safety shield 102, i.e. its final position after being pressed out of the housing 104 by the action of the expanding spring 304, is determined by an abutment of the sharp proximal edges of the projections 174 against the proximal end of the longitudinal through holes 220. In this position, in spite of the spring force still applied by the spring 304 in proximal direction, the safety shield 102 cannot moved further in proximal direction. The proximal portion 150 of the safety shield 102 has reached its position in which it protrudes out of the housing 104 at maximum. In this position, the sharpened needle tip 348 is positioned well behind the proximal end of the portion 150 and safety covered therein.

Blocking Distal Movement of Safety Shield 102 After Use

When pushing the safety shield 102 out of the housing 104, as described above, the combined arrangement formed by the shield retention indicator 306 and the shield retention indicator inner element 314 is kept at the distal end position within the distal end cap 316. However, as described above, due to the spring action of the spring 304, the trigger element 302 is moved in proximal direction. Thus, the trigger element 302 is pressed under the spring force of the spring 304 out of the engagement of the arms 408 of the shield retention indicator 306. In other words, the arms 408 once again flex-out, as can be seen in FIGS. 52a to 52d two overcome the proximal chamfered rim 363 of the trigger element 302.

During further movement of the trigger element 302 in proximal direction, the radially inward projections 412 of the arms 408 slide along the outer circumference of the trigger element 302 until they reach the chamfered annular reinforcement rib 374 of the trigger element 302. This can be seen in FIGS. 53a to 53d. In reaction to the further movement, as can be seen in FIGS. 54a to 54d, the arms 408 flex-out in radial outward direction once again, in order to overcome the chamfered annular reinforcement rib 374.

Having passed the chamfered annular reinforcement rib 374, the arms 408 due to the inherent elasticity snap radially inwards and grip distally right behind the chamfered annular reinforcement rib 374. The distal surface of the chamfered annular reinforcement rib 374 is slightly inclined such that it has a concave conical profile. In addition, the projections 412 are correspondingly inclined, such that they engage into this concave conical profile in a form-fitting manner. This engagement prevents any unintended further flexing out of the arms 408. Instead it keeps the arms 408 engaging the concave conical distal surface of the annular reinforcement rib 374. Thereby, the shield retention indicator 306 blocks any distal movement of the trigger element 302. As a consequence any distal movement of the safety shield 102 is also blocked. This means, that the safety shield 102 having reached the condition as shown in FIGS. 55a to 55d cannot be pressed into the longitudinal housing 104.

This is shown in FIGS. 56a to 56d, which depict views according to FIGS. 44a to 44d in a condition in which the device is entirely removed from the injection site on the patient's skin, wherein the safety shield is blocked against a further axial depression. Once a force is applied in this condition onto the proximal portion 150 of the safety shield 102, the arms 408 of the shield retention indicator 306 block any distal movement. The shield retention indicator 306 in this situation is supported by means of the shield retention indicator inner element 314, in particular its endplate 456 against the bottom surface 532 of the distal end cap 316. The letter, as mentioned above, is inseparably connected to the housing 104.

As a result, the safety shield 104 with its proximal portion 150 safely and irreversibly covers the needle 206 against any misuse.

Benefits

The device 10 according to the above described example of the present invention inter alia has the following beneficial features:

The device 10 can be assembled easily from the three different pre-assembled subassemblies syringe unit 100, pre-filled syringe 200 and power-pack 300.

The prefilled syringe 200 can be provided in different shapes and sizes, which just requires an adaptation of the syringe holder 106.

The distal end cap 50 can be easily removed from the housing 104, wherein the twisting-off operation is supported by the action of the shield spring 304.

During the use of the device, the device gives an audible and/or tactile and/or visible signal of the different states of operation.

As long as the drug has not been delivered, the user can recognize this state through the transparent housing 104 or a window provided therein.

The device does not show any visible indicator until the drug delivery is finished.

When the drug delivery has started by triggering the device by means of pressing it against the patient's skin, there is no possibility of stopping the delivery of the drug. This prevents that the device is used plural times.

The device is easy and intuitively to use as it has no separate trigger element, e.g. a button or the like. The triggering is just caused by pressing the device with its safety shield 104 against the patient's skin.

The device has no rotating parts and no correspondingly complicated rotational movements. This makes device simple to manufacture and easy as well as reliable in use.

In summary, the device provides an easy to assemble structure with the possibility of using different kinds of syringes. The device can be easily and intuitively used in a failsafe manner. The device provides several feedback signals to the user.

Alternative Examples for Syringe Holder

Figure 57:
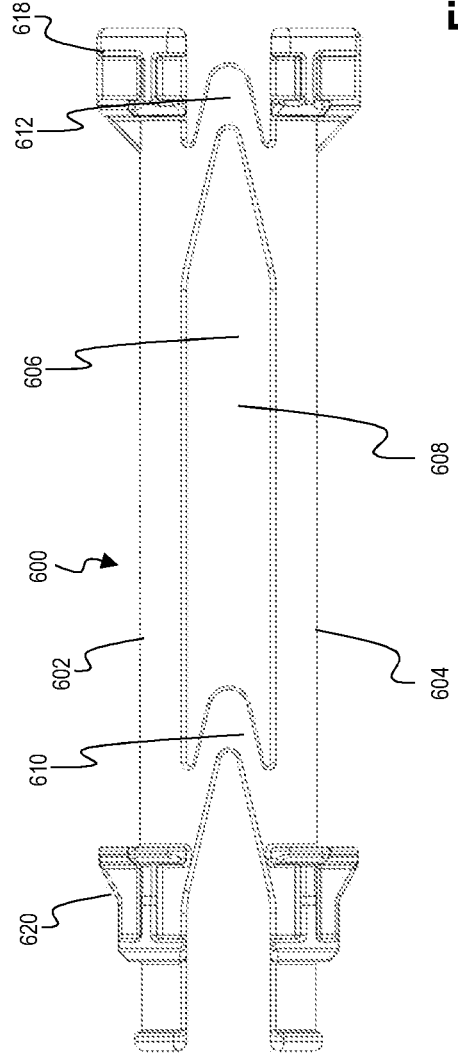
Figure 58:
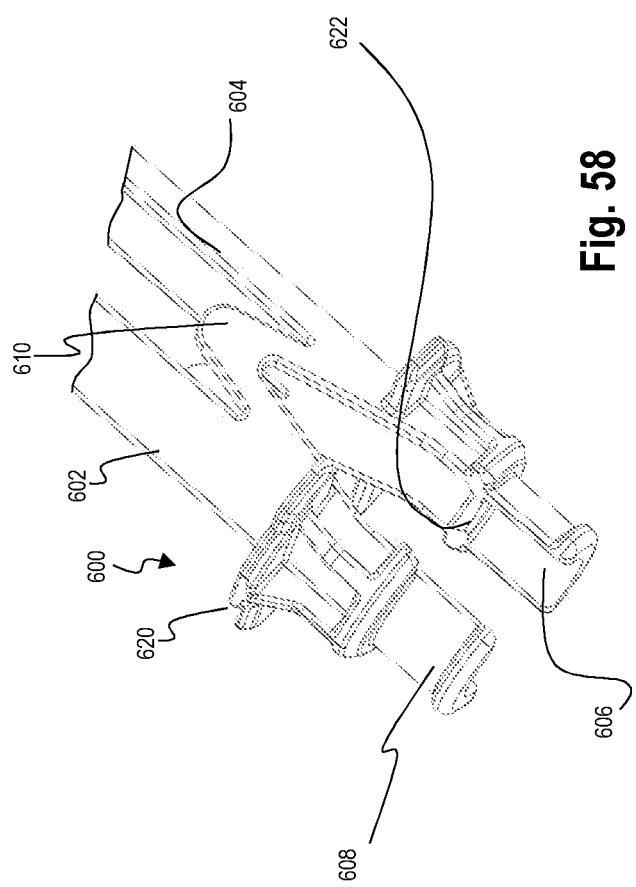

FIGS. 57 and 58 show an alternative example for a syringe holder 600. The syringe holder 600 is formed by two longitudinal shells 602, 604, which form a longitudinal slit 606, 608 there between. The two shells 602, 604 are connected by two flexible V-shaped arms 610, 612, on the distal end the proximal portion, respectively, which provide flexibility in circumferential direction to the syringe holder 600 and thereby allow that the shells 602, 604 move elastically apart when introducing a syringe. The syringe holder 600 further comprises at its distal end 614 and close to its proximal end 616 radial outward projecting structures 618, 620 for fixing the syringe holder within a housing of an autoinjector.

In FIG. 58, one can see a radial inner projection 622, which is formed within both shells 602, 604, for supporting the syringe in axial direction once plugged in from distal direction and received within the syringe holder 600.

FIGS. 59 and 60 show a further alternative example of a syringe holder 640. This syringe holder has a hollow cylindrical receiving tube 642 with a distal end 644 and a proximal end 646. Similar to the example according to FIGS. 57 and 58, this syringe holder 640 also includes radial outward projecting structures 648, 650 in order to hold the syringe holder within a housing of an autoinjector.

Close to its proximal end, the syringe holder is provided with two double-z portions 652, 654, which include inclined flexible arms 656, 658 interconnected by a circumferential rib 660. At its inner circumferential surface, the syringe holder includes a radially inward projection 662, which is formed circumferentially within both flexible double-z portions 652, 654 for supporting the syringe in axial direction once plugged-in from distal direction and received therein. In this syringe holder 640, the syringe is pushed-in from its distal end 644 with minor radial play within the hollow cylindrical receiving tube 642. For gripping the proximal front end of the glass body of the syringe, due to the elastic flexibility of the two double-z portions 652, 654, the arms 656, 658 slightly flex-out such that the circumferential ribs 660 move in radial outward direction.

Both alternative examples for a syringe holder according to FIGS. 57 to 60 have a circumferentially closed structure with features providing some flexibility in radial or circumferential direction. Thereby, it is possible to provide an easy assembling of the prefilled syringe with the syringe holder. The syringe is held simply by flexing elements which give-in in radial outward direction. Thereby, tolerance variations of the glass syringe can be compensated both in radial outward direction as well as axially. Nevertheless, the syringe holder has a robust structure by the shells or the cylindrical receiving tube.

FIG. 61a shows an automatic mechanical drug delivery device 1010, formed as an auto-injector, according to the invention in a perspective side view. The device 1010 comprises a longitudinal body 1012 extending along an axis X and a removable end cap 1050 at the proximal end of the device. The end of the device 1010 to which the removable end cap 1050 is located is called within this description the proximal end, which will be in contact with the patient. The opposite end, in FIG. 61 on the right side is called the distal end within this description.

A part of the body 1012 is covered by a label 1014, which extends from a middle portion towards a distal end portion of the device 1010. In the ready to use state shown in FIG. 61, one can see a tamper label 1016, which sticks to the body 1012 as well as the distal part of the end cap 1050. When the end cap 1050 is removed, the tamper label 1016 breaks and thereby indicates that the end cap 1050 has been removed.

FIG. 61 furthermore schematically shows two different planes A and B representing planes of longitudinal sections. In the following, when describing the structure and the operation of the device 1010, it is referred to these particular planes of longitudinal sections.

FIG. 62 shows three subassemblies of the device 1010. On the left side, one can see the syringe unit subassembly 1100 including the end cap 1050. Next to the syringe unit subassembly 1100, one can see a subassembly including a prefilled syringe unit 1200. On the right side, one can see a power-pack subassembly 1300. These three subassemblies 1100, 1200 and 1300 are provided as separate preassembled modules when assembling the device 1010 according to the invention. This allows to pre-assemble the syringe unit 1100 and the power-pack 1300 and to provide a corresponding prefilled syringe 1200 with a demanded medicament provided therein in a sealed manner and with the predetermined volume for drug delivery.

As will be seen in the following, the three subassemblies 1100, 1200 and 1300 can be assembled to the device by plugging the prefilled syringe 1200 into the receiving syringe unit 1100 and thereafter plugging the power-pack 1300 from the right side into the open distal end of the body 1012 of the syringe unit 1100 until it locks into a predetermined position. By this modular structure, the device according to the invention can be easily assembled in an error-free manner.

It is to be noted that although in the following a particular example of the device 1010 is described in its structure and functioning in regard to the figures, the components of the device 1010 as described in the following can be used also independently from the respective structure. In particular, each of the three subassemblies 1100, 1200 and 1300 and the components thereof can be used separately and independently from the other subassemblies. For example the proximal subassembly 1100 and its components can be used separately in another autoinjector, independent from the specific design of the syringe unit 1200 or the power-pack 1300. Therefore, the following description is not to be understood as a limiting disclosure in a way that each and every component can only be used together with the further components described in the following context. Instead, the present disclosure is to be understood in a way that each and every component disclosed therein can be claimed with its respective features separately independent from the interacting components of the respective subassemblies.

In the following the components of the subassemblies are described in detail.

FIG. 3 shows an exploded view of the syringe unit subassembly 1100. This syringe unit subassembly 1100 comprises the end cap 1050 formed by an end cap body 1052, a blade washer 1054 and a proximal end cap cover 1056. Moreover, the syringe unit subassembly 1100 comprises a safety shield indicator 1102, a safety shield 1104, a lock ring 1106, a longitudinal housing 1108 and a syringe holder 1110. These components will be described in detail in regard to FIGS. 66a to 73 in the following.

FIG. 64 shows an exploded view of the components of the subassembly forming the prefilled syringe 1200. This syringe subassembly includes a rigid needle shield 1202, a glass body 1204 with an integrally provided needle 1206, the medicament 1208 shown as a liquid column and a stopper 1210. These components of the prefilled syringe 1200 will be described in detail in regard to FIGS. 74 to 77.

FIG. 65 shows an exploded view of the components of the subassembly forming the power-pack 1300. This power-pack subassembly 1300 includes a plunger 1302, a drive spring 1304, a shield retention trigger element 1306 and a shield spring 1308. Moreover, the power-pack subassembly 1300 comprises a shield retention indicator 1310, a retainer 1312, a rotary click element 1314 and a distal end cap 1316. These components will be described in detail in regard to FIGS. 78a to 83b in the following.

FIGS. 66a and 66b show the end cap body 1052 from different perspective views. One can see the cylindrical body having a number of integrally formed radial gripping ridges 1058 extending in a longitudinal direction from the proximal end of the body 1052 to its middle portion. The distal part is formed by a cylindrical body having smooth outer surface 1060. This surface includes arrow-shaped through holes 1059 which indicate the direction of movement for twisting-off the end cap 1050 relative to the body 1012. Moreover, one can see in FIGS. 66a and 66b two opposite retaining ribs 1061 which are provided on the inner peripheral surface of the end cap body 1052 and which are interrupted by the through holes 1059, respectively. These retaining ribs 1061 are provided to retain the end cap body 1052 on the housing 1108 when engaging into a U shaped projection 1178, as will be discussed below in regard to FIG. 73.

In its interior, the end cap body 1052 includes an axially open receiving portion 1062 with a smooth receiving surface. Next to the receiving portion 1062 there is a portion having a formation of radial inwardly extending ribs 1064. Following to the portion including the ribs 1064, the end cap body 1052 includes a step surface 66 abruptly increasing the inner diameter of the end cap body 1052. The step surface 1066 follows in axial direction a closed sinus shape acting as a driving curve when it comes into engagement with a corresponding driving projection of the housing 1108 for twisting-on or twisting-off the end cap 1050 relative to the body 1012. In the distal portion the interior of the end cap body 1052 includes further radially inwardly extending ribs 1068 acting as contact means, which interact with the outer circumferential surface of the housing 1108.

FIG. 67 shows the cap cover 1056. It includes a cylinder with an outer circumferential surface 1070 in order to be introduced into the actually open receiving portion 1062 of the end cap body 1052 with a press-fit engagement. The cap cover 1056 has a closed proximal end wall 1072. Axially extending from this end wall 1072 in distal direction, the cap cover 1056 provides an inner cylindrical ring 1074 with a formation of radially inner ribs 1076. The distal end surfaces 1078 of the inner ribs 1076 are slightly sloped inwardly to form a circumferential bevel.

FIG. 68 shows the blade washer 1054. The blade washer 1054 has a circular outer circumference 1080 surrounding a ring-shaped body 1082. The blade washer 1054 includes four radially inwardly extending lobes 1084 integrally formed with the ring-shaped body 1082 and ending in a circular radially inner gripping surface 1086. In a side view, one can see that the blade washer 1054 has a frusto-conical shape, wherein the lobes 1084 provide an axial spring action, i.e. the lobes 1084 can be deflected elastically in axial direction.

Generally, the external geometry 1080 of the blade washer 1054 may be of circular or any other geometry to suit assembly loads or packaging space available. There may be two or more extending lobes 1084 and the blade geometry may be of any format to achieve certain insertion forces and of any ability to hold forces from the rigid needle shield when the end cap is removed from the housing. Generally, the blade washer 1054 may have a planar or flat shape. In other examples the blade washer could also have some non-planar pre-forming, e.g. it can be formed conical or wave-like. It may be possible in an example to form a rib around the outer rim of the blade washer to enforce it. This may be to allow rotation of the blade washer during cap removal. If the cap rotates and the blade washer is only pulled longitudinally a detrimental condition called coring can be eliminated. Coring occurs where the rubber of the rigid needle shield is rotated around the needle. It may then be possible for a plug of rubber to remain inside the needle, which is undesired. This may cause a blockage stopping the device from functioning correctly.

In an assembled state of the end cap 1050, the blade washer 1054 is arranged on the proximal surface of the ribs 1064 and is clamped against the ribs 1064 by pressing the cap cover 1056 into the receiving portion 1062. The blade washer 1054 is thereby fixedly held or arranged with some axial clearance between a front surface 1086 of the cylindrical radially outer portion of the cap cover 1056 and the ribs 1064, in order to allow axial resilient deflection for gripping the rigid needle shield 1202 described below. The inner ring 1074 is arranged in sufficient distance to the lobes 1084 such that the lobes can flex proximally in axial direction.

FIGS. 69a and 69b show the safety shield 1104 in different perspective views. The safety shield 1104 includes a ring-shaped body 1112 with two diametrically opposing longitudinal arms 1114, 1116. The ring-shaped body has a stepped and rounded outer surface profile such that it decreases in diameter from a cylindrical portion 1118 to a projecting rounded front end portion 1120 having an axial opening 1122. The inner diameter of axial opening is slightly larger than the outer diameter of the rigid needle shield 1202 in order to allow a frictionless movement of the syringe together with the rigid needle shield 1202 therethrough. The front end portion 1120 of the safety shield 1104 is rounded and free of sharp edges and provided for getting in contact with the patient's skin. Moreover, the safety shield 1104 of the device 1010 according to the present invention forms the trigger element when being pressed with a required triggering force against the patient's skin. Therefore, this front end portion 1120 is smoothly formed such that it does not injure or scrape on the patient's skin.

The two longitudinal arms 1114 and 1116 have a slightly rounded shape and include next to the cylindrical portion 1118 a longitudinal slotted through hole 1124, respectively. Hence, the two through holes 1124 are provided in opposing position relative to one another. These through holes 1124 act as guiding means for guiding a longitudinal movement of the needle shield 1104 within the device 1010.

The ring-shaped body 1112 of the needle shield 1104 includes four radially inwardly extending ribs 1126. These inner ribs 1126 are provided in order to support the rigid needle shield 1202 against deflections and thereby support the position of the prefilled syringe 1200 in an assembled state, i.e. during transportation. Moreover, the ring-shaped body 1112 of the needle shield 1104 includes two opposed through holes 1128 with a proximal wall 1129 and a distal wall 1130, each running in substantially perpendicular direction to the main axis X.

FIG. 70 shows the safety shield indicator 1102. The safety shield indicator 1102 is formed as a thin-walled element which is connectable to the proximal ring-shaped body 1112 of the needle shield 1104 by a press-fit and/or snap-fit engagement. As an alternative, the safety shield indicator can be just provided as a colored coating on the front surface of the needle shield 1104 or may be integrally molded as a colored portion of the needle shield 1104. To this purpose, the safety shield indicator 1102 has an inner surface profile corresponding to the outer surface profile of the ring-shaped body 1112 of the needle shield 1104. The safety shield indicator 1102 is provided with a circumferential outer surface having a signalling color, i.e. yellow, orange or red, which is clearly visible by a user. Thereby, as will be discussed in detail in regard to the operation of the drug delivery device 1010 according to the present invention, the user, i.e. the medical practitioner or the patient, of the device 1010 can easily recognize when the safety shield indicator 1102 protrudes out of the housing 1108 and covers the needle 1206.

FIGS. 71a and 71b show the structure of the lock ring 1106. The lock ring 1106 is provided to engage with the safety shield 1104 during use as the safety shield 1104 is fully pressed into the housing 1108 when the device 1010 is triggered to deliver the medicament to the patient. After engagement with the safety shield 1104, the lock ring 1106 is permanently coupled to the safety shield 1104 and prevents the safety shield 1104 from being pushed back a second time into the housing 1108 when the device has been used and after the drug has been fully delivered.

The lock ring 1106 includes a closed ring 1132 with two opposing recesses 1134. Radially inside of these recesses 1134, the lock ring 1106 is provided with two flexible arms 1136, formed on opposing lobes 1138 protruding radially inwardly from the lock ring. In addition, the lock ring includes two further radially inwardly projecting lobes 1140. The two flexible arms 1136 protrude in proximal direction and have a radially outwardly extending snap lug 1142, respectively. Moreover, at the proximal end, flexible arms 1136 have a front surface running substantially in radial direction.

In other examples the ring may be of a different sectional geometry and the number of legs may be singular to multiple.

On the distal side of the closed ring 1132, the lock ring 1106 is provided with four slightly flexible arms 1146 extending in distal direction. Each of the flexible arms 1146 has a snap lug 1148 on its distal end extending radially inwardly with a slightly inclined distal wall 1150.

Thereby, each flexible arm 1146 provides a sharp tooth profile on its distal end. It is important to mention that the degree of flexibility of the arms 1146 is to be adapted to the spring rate of the spring 1308, such that the slide over forces of these arms 1146 are less than the safety shield spring force. This is to ensure that the lock out after injection and the removal of the device from the skin always works. This will be discussed in the following when the functioning is described.

FIGS. 72a and 72b show one example for the syringe holder 1110. The syringe holder 1110 has the purpose to receive and hold the prefilled syringe 1204 within the housing 1108. It is adapted to receive different kinds of syringes with different volumes of the medicament without the need of substantially changing the dimensions of other components of the device 1010. Therefore, different sizes for syringe holders 1110 are to be provided in adaptation to the different kinds of syringes.

The syringe holder 1110 provides a longitudinal tube-like body 1152. At its proximal end, the tubular body 1152 has four projecting flexible arms, wherein each arm 1154 of a first pair of two opposing arms 1154 has a radially inwardly projecting lug 1156 forming a gripping element. Each arm 1158 of a second pair of the two opposing arms 1158 as a bevelled lug 1160 which is supported by means of a crossing transverse support rib 1162. The bevelled lug 1160 is provided with an inclined surface 1164 on its proximal portion. The distal end of the syringe holder 1110 has an angled collar 1166 with two recesses 1168 on opposite sides thereof. The collar 1166 has a radial portion 1170 and a longitudinal portion 1172 which are connected by a rounded the transition. The radial portion 1170 can be rounded or chamfered at its transition to the longitudinal portion 1172 in order to facilitate the assembly, in particular the introduction of the syringe holder 1110 together with the syringe 1200 into the housing 1108.

FIGS. 73a to 73c show the housing 1108 in different views. The housing 1108 has the purpose of forming the main body 1012 of the device 1010. It is formed from a stable, rigid, transparent or opaque material. If not entirely transparent, the housing can be formed with drug viewing cutouts or transparent windows in order to make the drug and the actual state of the device visible to a user. The housing 1108 is formed by a longitudinal tubular member 1174. At its proximal end, the tubular member is provided with a front surface 1176 having a closed sinus shaped contour. Close to the proximal end and the front surface 1176, the housing 1108 is provided with two U-shaped lateral projections 1178, which are arranged opposite to one another and project radially outwardly. The U-shaped lateral projections 1178 are provided to receive the retainer ribs 1061 of the end cap body 1052, described in regard to FIG. 66a, in order to retain the end cap body 1052 before use in position on the housing 1108. At its distal end, the housing has a circular front surface 1180. Close to the end surface and in substantially longitudinal alignment with the projections 1178, the housing 1108 has two opposing transverse slits 1182. In the region between the distal end and the slits 1182, the housing is integrally formed with two pairs of projecting knobs 1184. The projecting knobs 1184 can also have an alternative shape. They have the function to provide anti-rolling features of the device 1010 on a flat surface. Each pair of knobs 1184 is aligned with the respective transverse slit 1182.

In its interior, the housing 1108 is provided with a ring structure 1186, which is integrally connected with the tubular member 1174 by means of pair of opposing rigid connecting arms 1188. The connecting arms 1188 are formed by a stable E-like structure with three longitudinal connecting ribs and one transverse connecting rib. The size of the connecting ribs and the E like sectional shape are to provide structural rigidity to the housing 1108. This joining geometry is also important for the flow of the material when the component is molded. Moreover, the ring structure 1186 has a longitudinal crest 1190, with two V-shaped cutouts 1192 opening in distal direction and terminating in proximal direction at a radial circular base surface 1194. The V-shaped cutouts 1192 provided for receiving the bevelled lugs 1160 with the transverse support ribs 1162 of the syringe holder 1110. A longitudinal collar 1196 extends in proximal direction from the base surface 1194. This geometry guides the movement of the safety shield 1104 during the operation of the device 1010 and, furthermore, locates the syringe holder 1110 in place within the housing 1108. The collar 1196 has a level of rigidity to restrain the loads applied through the syringe 1200 when the device is activated, as will be discussed below.

FIGS. 74 and 75 show perspective views of the rigid needle shield 1202 and an insert 1212 thereof. The rigid needle shield 1202 is formed by a tubular member 1214 with an open distal end 1216 and a closed proximal end 1218. In its front portion it has a surface formed with transverse gripping ribs 1220. Close to its distal end, it has two opposite rectangular through holes 1222.

The insert 1212 shown in FIG. 75 is formed by a soft deformable material and can be pressed into the rigid needle shield 1202 such that it is fixedly held therein. It has an annular collar 1224 close to its distal end which engages with the rectangular through holes 1222 of the rigid needle shield 1202.

FIG. 76 shows the syringe 1204. The syringe 1204 is formed by a hollow cylindrical glass body 1230 having an open distal end 1232, which is surrounded by a circumferential annular collar 1234 with two flattened opposite side surfaces 1235. At its proximal portion, the cylindrical glass body 1230 is formed with a rounded taper 1233 and transits into a hollow conical glass portion 1236. The hollow conical glass portion 1236 terminates in a proximal head 1238, in which said needle 1206 with a sharpened needle tip 1240 is fixedly received.

FIG. 77 shows the stopper element 1210 formed from a flexible material, e.g. a rubber. At its proximal portion, it has a smooth cylindrical outer circumferential surface 1242, which has a diameter adapted to the inner diameter of the hollow cylindrical glass body 1230 of the syringe such that the stopper element 1210 slidably engages the inner circumferential surface of the hollow cylindrical glass body 1230 in a fluid tight manner. On the distal portion of the outer surface, the stopper element 1210 is provided with four circumferential annular recess is forming three circumferential sealing the ribs 1244. The stopper element 1210 has cup-shape with a closed proximal end 1246 and an open distal end 1248.

Turning now to the components of the power-pack, FIGS. 78a and 78b depict the plunger 1302 in different perspective views. The plunger 1302 is formed by a longitudinal pipe shaped hollow element 1320 which has at its proximal end a plunger head 1322. The plunger head 1322, which can be formed integrally with the hollow element 1320 or as a separate piece, has a cylindrical portion 1324 with an enlarged outer diameter in the example shown. This enlarged plunger head 1322 is used for larger syringes, e.g. having a drug volume of 2.25 ml instead of only 1 ml. In case of smaller syringes, e.g. having a drug volume of 1 ml, the enlarged plunger head 1322 can be omitted and the plunger 1302 has just straight cylindrical shape on its proximal end. In the middle portion of the plunger 1302, a pair of opposing rectangular through holes 1326 is provided in the wall of the hollow element 1320. At the distal end, the hollow element 1320 is provided with four longitudinal ribs 1328, equidistantly arranged around the circumference of the hollow element 1320. Moreover, the distal end of the plunger 1302 provides two slotted pathways 1330 opening to the distal end face 1331, each having an inclined portion 1332 and a longitudinal end portion 1334.

FIGS. 79a and 79b depict the shield retention trigger element 1306. The shield retention trigger element 1306 is formed by a hollow bushing 1340 having a radial annular collar 1342 integrally formed at its proximal end. The bushing 1340 is provided with two opposite slits 1344 opening to its distal end. The two opposite slits 1344 provide longitudinal guiding surfaces 1346 extending through the entire bushing 1340.

FIGS. 80a and 80b depict the shield retention indicator 1310. The shield retention indicator 1310 has the purpose of providing a visible indicator for the actual state of use, in particular an indicator showing that the device 1010 was already used for delivering a drug. It comprises an annular cylindrical body 1350, having at its proximal inner circumferential surface radially inwardly protruding ribs 1352. Moreover, the annular cylindrical body 1350 has two opposing flexible arms 1354 extending in proximal direction, wherein a first portion 1356 runs in longitudinal direction, a second portion 1358 is inclined radially inwards, and a third portion 1360 extends in longitudinal direction, however, on a level which is further radially inward then the first portion 1356. At its proximal end, each of the arms 1354 has a retaining projection 1362 extending radially outwards.

In its middle portion, the annular cylindrical body 1350 has an annular flange 1364 extending in radial outward direction. Two opposite arcuate wall members 1366 extend in distal direction from the flange 1364. The outer circumferential surfaces 1368 of these arcuate wall members 1366 are provided with a signalling color and/or a signalling visible pattern.

FIGS. 81a and 81b depict the retainer 1312 of the power-pack 1300. The retainer 1312 acts as the control member including a plurality of control functions of the power-pack 1300. The retainer is formed from a hollow cylindrical body 1370. On two opposing sides the cylindrical body 1370 includes a U-shaped cutout 1372 forming a longitudinal flexible arm 1374. The longitudinal flexible arm 1374 is integrally connected with the hollow cylindrical body 1370 at its distal end 1376. At its proximal end, the flexible arm 1374 is provided with a chamfered radial outward projection 1378 and, on the opposite side, with a corresponding chamfered radial inward projection 1380. Moreover, the cylindrical body 1370 is provided with two opposing longitudinal cutouts 1382 in an area rotated by 90° relative to the flexible arms 1374 formed by the cutouts 1372. The longitudinal cutouts 1382 extend approximately with the same longitudinal extension as the U-shaped cutout 1372. In the region of about one third of the longitudinal length of the cutouts 1382 close to their proximal end, the cylindrical body 1370 comprises lateral projections 1384 transversely bridging the cutouts 1382.

At its proximal end, the cylindrical body 1370 is provided with two flexible arms 1390 integrally formed with the cylindrical body 1370 and inclined by an angle of about 45° relative to the proximal front surface of the hollow cylindrical body 1370. These flexible arms 1390 are connected with a ring-shaped head portion 1392. The ring-shaped head portion 1392 is formed as a bushing with a cylindrical portion 1394 and a proximal flange portion 1396. The head portion 1392 can be integrally formed with the flexible arms 1390 or formed as a separate piece fixedly connected to the flexible arms 1390, e.g. by means of an intermediate connecting ring.

At its distal end, the cylindrical body 1370 is formed with two opposing groups of outer longitudinal ridges 1400, 1402, 1404, extending in radial outward direction from the cylindrical body 1370. Distally from the ridges 1400, 1402, 1404, the cylindrical body 1370 includes a cylindrical portion 1406 with increased diameter. This cylindrical portion 1406 with increased diameter includes two opposing rounded lateral cutouts 1408, which are aligned in longitudinal direction with the cutouts 1382 of the cylindrical body 1370. The remaining non-cutout wall sections of the cylindrical portion 1406 are provided with two longitudinal projections 1410 extending slightly in radial outward direction and having a rectangular shape when viewed in a side view. These projections 1410 are provided with a transverse slot 1412 in their middle portion, respectively.

FIGS. 82a and 82b depict the rotary click element 1314. The rotary click element is provided for changing the driving force of the main spring 1304. It is formed by a hollow cylindrical bushing 1420, having a smooth proximal front surface 1422 and a distal surface formed with an annular crest of shark teeth 1424. Radially inward from the crest of shark teeth 1424, the rotary click element 1314 includes two opposing cylindrically shaped wall portions 1426 which are divided by a transverse slit 1428. On the inner circumferential surface, the bushing 1420 is provided with projections for engaging the main spring 1304 for a common rotation therewith.

FIGS. 83a and 83b depict the distal end cap 1316 of the device 1010. The distal end cap 1316 has a distal plate-formed end cap body 1440 closing the distal opening of the housing 1108. For that purpose, the end cap body 1440 is formed with two projecting flexible arms 1442 having engagement projections 1444 on their proximal ends. These flexible arms 1442 act as snap hooks engaging with the corresponding openings 1182 of the housing 1174. Moreover, radially inwards from the flexible arms 1442, the end cap body 1440 is formed with a hollow cylindrical body 1446. The hollow cylindrical body 1446 is provided with two opposing nose elements 1448, which extend in radial outward direction. Moreover, the hollow cylindrical body 1446 is provided with two proximal slopes 1450 extending in longitudinal direction. Inside the hollow cylindrical body 1446, on the surface of the end cap body 1440, there is provided a further crest of shark teeth 1452 adapted to engage the crest of shark teeth 1424 formed on the rotary click element 1314. A longitudinal cylindrical rod member 1454 extends in the centre of the crest of shark teeth 1452 from the surface of the end cap body 1440 in proximal direction.

In the following, the assembled state of the device 1010 is described in regard to FIGS. 84a and 84b. This is also the initial state of the device 1010, i.e. the state of the device how it is delivered to the user. In the assembled state of the device 1010 the end cap 1050 is removably fixed to the longitudinal housing 1108, wherein the end cap 1050 is held with its retaining ribs 1061 and the corresponding recess within the U-shaped projections 1178 of the housing 1108. The syringe 1204 is held within the syringe holder 1110, which is received in the ring structure 1186 of the housing 1108. Moreover, the syringe 1204 is pressed via its annular collar 1234 or flange by means of the head portion 1392 in proximal direction against the ring structure 1186 of the housing 1108, wherein the flexible arms 1390 act as a spring means providing a spring force in axial direction in order to hold the syringe 1204 in place within the syringe holder 1110. The rigid needle shield 1202 engages the hollow conical glass portion 1236 by means of the insert 1212. The soft insert 1212 safely covers the needle 1206 and maintains sterility of the contact needle and contained medicament. As one can see, the outer surface of the tubular member 1214 with the transverse gripping ribs 1220 is engaged by the flexible lobes 1084 of the blade washer 1054. The blade washer 1054 is held within the 1050 by means of the cap cover 1056.

Moreover, FIG. 84b shows the ring-shaped body 1112 of the safety shield 1104. The safety shield 1104 is pressed by the end cap 1050 via the longitudinal arms 1114, 1116 against the force of the shield spring 1308, wherein the shield retention trigger element 1306 acts as an interface between the longitudinal arms 1114, 1116 and the shield spring 1308. The proximal end of the shield spring 1308 engages against the flange 1342 of the shield retention trigger element 1306, wherein the distal end of the shield spring 1308 presses against the flange 1364 of the shield retention indicator 1310.

The shield retention indicator 1310 is held by means of its arms 1354 in its axial position in spite of the compressed shield spring 1308 and the resulting forces. This is achieved due to the fact that the arms 1354 reach through the longitudinal cutouts 1382 of the retainer 1312 and engage with their radial retaining projections 1362 behind the lateral projections 1384 bridging the cutouts 1382 of the retainer 1312. Moreover, in this state, the plunger 1302 arranged radially inside the arms 1354 prevents that the arms 1354 flex radially inwards.

The plunger 1302 retains the main spring 1304 in a compressed state. The proximal end of the main spring 1304 presses against the proximal end of the plunger 1302 to which the plunger head 1322 is fixed. One can see that the plunger head 1322 is slidably received within the hollow glass body 1230 of the syringe 1204 close to the stopper element 1210. Moreover, FIG. 84b shows the medicament 1208 as a liquid column included within the syringe 1204.

The distal end of the main spring 1304 protrudes out of the plunger 1302 and is received within the hollow interior of the rotary click element 1314, where it is also engaged in a non-rotatable manner. The rotary click element 1314 in turn is received within the hollow cylindrical body 1446 of the distal end cap 1316, wherein the two shark teeth formations 1424 and 1452 engage with one another. A relative rotation of the rotary click element 1314 and the distal end cap 1316 causes clicking sounds, which are audible or sensible by the user.

As can be seen in FIG. 84b on the right side, the cylindrical pole member 1454 extends in proximal direction into the hollow interior of the main spring 1304 and acts as an axial guiding element for the compressed main spring 1304. The distal end cap 1316 is plugged into the housing 1108, wherein the flexible arms 1442 with their radially outwardly pointing engagement projections 1444 are engaged with the transverse slits 1182 of the housing and they thereby hold the distal end cap 1316 in place against resulting spring forces.

From this fully assembled initial position, the device 1010 according to this example of the invention is used as follows:

In order to remove the end cap 1050, it is twisted-off from the housing 1108 according to the direction of the arrow-shaped opening 1059. Thereby, the temper label 1016 is ruptured. The twisting-off force must be large enough in order to overcome the interaction between the U shaped projections 1178 on the housing 1108 receiving the retaining ribs 1061 provided on the inner surface of the end cap body 1052. The twisting-off movement follows the profile of the sinus shaped front surface 1176 of the housing 1108. Due to the fact that the safety shield 1104 in the ready to use state is biased by the shield spring 1308 against the end cap 1050, the twisting-off movement out of the end cap 1050 is supported by this biasing force of the shield spring 1308. Thereby, after overcoming an initial resistance also provided by the tamper label 1016, the twisting-off movement of the end cap 1050 is supported by the spring force and the user experiences a supported removal of the end cap 1050. During the removal of the end cap 1050, while it supports the twisting-off movement of the end cap 1050, the shield spring 1308 expands in axial direction and presses the safety shield 1104 out of the housing 1108 until it finally reaches its fully extended position, where it covers the needle 1206. Moreover, during the removal of the end cap 1050, the rigid needle shield 1202 which is gripped by the lobes 1084 of the blade washer 1054, is withdrawn together with its insert 1212 from the hollow conical glass portion 1236 of the syringe 1204. Thereby the needle 1206 with its needle tip 1240 is exposed within the ring-shaped body 1112 of the safety shield 1104.

In other words, the removable end cap 1050 is retained to the housing 1108 by the U shaped projection 1178. This is shown as a U in shape but may be of a number of other geometrical formats. Its function is a restraint on the middle of the U. This sets the pull-off force for the removable end cap 1050 if pulled. The removable end cap 1050 has the ribs 1061 in the middle of the arrow cut out that contacts the middle of the U-shaped projection 1178. The respective angle aligned which stops pull-off and to angles which, when larger, require less pull-off forces. The ability of the plastic region of the arrow cut-out 1059 and the angle in combination allow tuning the pull-off force to the required levels. Rotationally the sides of the U-shaped projection 1178 are angled to tune the initial torque required to start removal of the removable end cap 1050. The longitudinal and rotational restraints of the U-shaped projection 1178 and restraining rib 1061.

FIGS. 85*a* and 85*b* show longitudinal sectional views of the drug delivery device according to the example of the present invention in a state where the end cap 1050 has just been completely removed, wherein FIG. 85*a* is the longitudinal section along plane A indicated in FIG. 61 and wherein FIG. 85*b* is the longitudinal section along plane B indicated in FIG. 61.

In this state, the safety shield 1104 projects with its ring-shaped body 1112 out of the housing 1108. The user can see the safety shield indicator 1102 with its signalling color protruding out of the housing. The shield spring 1308 is in a partially relaxed but still substantially constrained state. The main spring 1304 is still fully compressed and it is kept in this fully compressed state due to the fact that the flexible arms 1374 of the retainer 1312 engage with the chamfered radial inward projections 1380 into the opposing rectangle of through holes 1326 of the plunger 1302. Thereby, the plunger 1302 is held against the spring force of the main spring 1304 in axial position preventing an expansion of the main spring 1304. The power-pack 1300 is preloaded.

The possible range of axial movement of the safety shield 1104 is determined by the length of the longitudinal slotted through holes 1124 in each of the longitudinal arms 1114, 1116, which receive the bevelled lugs 1160 of the syringe holder 1110. This can also be achieved in an alternative way, i.e. by projections guided in longitudinal slots within the housing 1108 or the like. As discussed above, in the assembled state the syringe holder 1110 is fixedly retained within the housing 1108.

For using the device 1010, as shown in FIGS. 85*a* and 85*b*, the device is positioned on the patient's skin S at a location, where the patient intends to inject the medicament, e.g. against a thigh of the patient. The device 1010 is then pushed by the user in proximal direction onto the patient's skin S. Thereby, the safety shield 1104 is pressed into the housing 1108 against the biasing force of the shield spring 1308, while—due to the pushing movement of the device—the needle tip 1240 penetrates the patient's skin S and the needle 1206 is pushed through the patient's skin S into the patient's tissue. Finally, when it is fully depressed into the housing 1108, the safety shield 1104 hits with the distal end surface of its ring-shaped body 1112 against the proximal front surface of the connecting arms 1188, which connect the housing 1108 with the ring structure 1186. At this point, no further axial movement of the safety shield 1104 into the housing 1108 is possible and the safety shield 1104 is blocked.

This position of a fully depressed safety shield 1104 is shown in FIGS. 86*a* and 86*b* depicting longitudinal sectional views of a state, when the drug delivery device is just fully pressed against the patient's skin and the drug delivery through is just started.

In this state, the two flexible arms 1136 of the lock ring 1106 engage with their snap lugs 1142 into the corresponding openings 1128 of the ring-shaped body 1112 of the safety shield 1104. Thereby, the lock ring 1106 is fixedly coupled to the safety shield 1104 providing a common movement in axial direction during further use. Moreover, in this state, the safety shield indicator 1102 is mainly covered by the housing 1108, as the ring-shaped body 1112 is substantially received within the housing 1108.

As can be seen in FIG. 86*b*, by pushing the safety shield 1104 into the housing, the two longitudinal arms 1114, 1116 are moved in distal direction while they are guided by the engagement of the bevelled lugs 1160 and the slots 1124. Thereby the shield retention trigger 1306 is moved against the compression force of the shield spring 1308 in distal direction. The shield retention trigger 1306 is moved in distal direction to such an extent that it unblocks the chamfered radial outward projections 1378 of the flexible arms 1374 of the retainer 1312. As a consequence, the flexible arms 1372 are free to flex in radial outward direction. Due to the biasing of the main spring 1304 pressing the plunger 1302 in proximal direction and due to the chamfered design of the radial inward projections 1380 interacting with the correspondingly chamfered rim of the through holes 1326 of the plunger 1302, the flexible arms 1374 are forced radially outwardly by the plunger 1302 and thereby disengage from the openings 326. In the following, the plunger 1302 can move in proximal direction, contact the stopper element 1210, shift the stopper element 1210 in proximal direction within the glass body of the syringe 1204 and start delivering, i.e. pressing out, the medicament through the needle 1206 into the patient's tissue.

FIGS. 87a and 87b show longitudinal sectional views in an intermediate state, when the drug delivery device delivers the drug to the patient, wherein the plunger 1302 has contacted the stopper element 1210 and has moved it within the syringe 1204 over a certain distance to press out the medicament through the needle. In FIG. 87b, one can clearly see that the flexible arms 1374 have been bent radially outwardly and released the openings 1326. As a matter of course, the plunger 1302 is moved in proximal direction under the spring force of the main spring 1304, which tends to expand.

Finally, the main spring 1304 has driven the plunger 1302 and thereby the stopper element 1210 in immediate proximity to the rounded taper 1233 of the syringe 1204. FIGS. 88a and 88b show longitudinal sectional views depicting this state, when the drug delivery is close to an end. In this state, the distal end of the plunger 1302 with its end face 1331 just passes the proximal side of the radial inwardly extending projections 1380 of the flexible arms 1374 of the retainer 1312. When the end face 1331 of the plunger 1302 passes the proximal side of the projections 1380, the flexible arms 1374 can flex radially inwards behind the end face 1331. Moreover, this radially inward movement of the flexible arms 1374 may provide a certain audible and or tactile signal to the user, as the proximal front portion of the flexible arms 1374 hits the circumferential outer surface of the distal end of the plunger 1302.

Moreover, as can be seen in FIG. 88b, in this state close to the end of the drug delivery with the plunger 1302 nearly fully advanced in proximal direction within the syringe 1204, the plunger 1302 has also passed with its distal end surface 1331 the proximal end of the flexible arms 1354 of the shield retention indicator 1310. Thus, the plunger 1302 unblocks in radial inward direction the flexible arms 1354 of the shield retention indicator 1310. As a consequence, due to the biasing force of the compressed shield spring 1308, the chamfered retaining projections 1362 of the arms 1354 slide along the proximal front surface of the lateral projections 1384 transversely bridging the cutouts 1382 of the retainer 1312. Thereby, the flexible arms 1354 are forced radially inwardly and flex inwards. The flexible arms 1354 are now free to pass the lateral projections 1384 in distal direction. As the compressed shield spring 1308 tends to expand, it moves the shield retention indicator 1310 in distal direction until it hits the distal end cap 1316 resulting in an audible and/or tactile signal being given to the user.

Moreover, the opposite arcuate wall members 1366 with their outer circumferential surfaces colored with a signal color enter into the free circumferential space between the flexible arms 1442. As mentioned above, the housing 1108 is formed from a transparent material. The label 1014 ends in a substantial distance, e.g. a distance of more than 6 to 20 mm, from the proximal end of the housing 1108 providing thereby a circular transparent window 1198 allowing the user to see the interior of the housing 1108.

In the states shown in FIGS. 84a, 84b to 87a, 87b, the window is clear. However, as shown in FIG. 89b, as soon as the shield retention indicator 1310 is released by the radial inward movement of the arms 1354 and pressed by the shield spring 1308 in distal direction, the accurate wall members 1366 with the colored or patterned circumferential surfaces 1368 enter into the circumferential free space and are visible through said circular transparent window 1198. Thereby, the user also receives a visible indication in the window 1198 indicating that the drug delivery has come to an end. In another example this could be one or a plurality of windows if the label or housing created opaque and clear regions.

FIGS. 89a and 89b show longitudinal sectional views in a state, when the drug delivery device has fully delivered the drug to the patient. One can see, that the main spring 1304 is substantially relaxed and has pressed the plunger 1302 together with the stopper element 1210 fully against the inner surface of the rounded taper 1233 of the syringe 1204. The medicament is fully pressed out through the needle 1206 into the patient's tissue. The shield retention indicator 1310 this pressed by the shield spring 1308 fully to the distal end and can be seen through the window 1198 by the user.

The user knows by the audible and/or tactile signal as well as by the visual indication through the window 1198 that the drug delivery has come to an end. The user then removes the device 1010 from its skin by retracting it in axial direction, thereby withdrawing the needle out of its tissue. While removing the device 1010 from its skin, i.e. while withdrawing the needle out of its tissue, the a safety shield 1104 remains in permanent contact with the patient's skin S until it fully covers and protrudes over the needle 1206 with its needle tip 1240. This is due to the fact that the needle shield is pressed by the shield spring 1308 together with the shield retention trigger element 1306 in proximal direction out of the housing 1108.

FIGS. 90a to 90c show different views of a state, when the drug delivery device was removed from the patient's skin and secured in a locked state after use. The safety shield 1104 which is permanently coupled to the lock ring 1106 (see FIG. 86a) protrudes out of the housing 1108. The lock ring 1106 engaging by means of its flexible arms 1136 with the corresponding openings 1128 in the ring-shaped body 1112 blocks the safety shield 1104 against any further distal movement within the housing 1108. In other words, the lock ring 1106 prevents that the safety shield 1104 is pressed back into the housing. Thereby, the safety shield 1104 safely covers the needle 1206 with its needle tip 1240, which is contaminated with patient's blood, against any manipulation or any contact with a patient or practitioner.

The blocking of the safety shield 1104 against any movement in distal direction is achieved by the four flexible arms 1146 formed on the distal side of the lock ring 1106. When the safety shield 1104 is pressed out of the housing 1108 under the force of the shield spring 1308 while the device 1010 is removed from the insertion site on the patient's skin, due to the permanent coupling of the arms 1136 with the safety shield 1104 the safety shield 1104 entrains the lock ring 1106 with this movement. Thereby, the lock ring 1106 is moved with its four flexible arms 1146 across the outer circumferential surface of the ring structure 1186 integrally formed within the housing 1108. Finally, the flexible arms 1146 pass with their distal wall 1150 the proximal front edge of the ring structure 1186 of the housing 1108 and flex radially inwards. Thereby, the four flexible arms 1146 with their distal wall 1150 snap radially inwards in front of the proximal surface of the ring structure 1186. As a consequence, the flexible arms 1146 act as fixed spacers between the safety shield 1104 and the proximal front surface of the ring structure 1186. By means of the lock ring 1106, the safety shield 1104 is secured against any relative distal movement into the housing 1108. Moreover, the safety shield 1104 is also secured against any further proximal movement out of the housing 1104, i.e. against being withdrawn out of the housing, as it is blocked by means of the radial distal surface of the bevelled lugs 1160 engaging into the longitudinal slots 1124 of the arms 1114, 1116.

Thereby, any further use of the device 1010 is prevented. It is also not possible to screw or push the end cap 1050 onto the housing 1108, as it is blocked by the protruding and lock safety shield 1104. The user can see the colored shield indicator 1102 as well as the colored wall segments 1366 of the shield retention indicator 1310 through the window 1198.

The device 1010 according to the above described example of the present invention inter alia has the following beneficial features:

The device 1010 can be assembled easily from the three different pre-assembled subassemblies syringe unit 1100, pre-filled syringe 1200 and power-pack 1300.

The prefilled syringe 1200 can be provided in different shapes and sizes, which just requires an adaptation of the syringe holder 1110.

The distal end cap 1050 can be easily removed from the housing 1108, therein the twisting-off operation is supported by the action of the shield spring 1308.

During the use of the device, the device provides plural possibilities of giving an audible and/or tactile and/or visible signal of the different states of operation.

As long as the drug has not been delivered, the user can recognize this state through the window 1198 which does not show any visible indicator until the drug delivery is finished.

When the drug delivery has started by triggering the device by means of pressing it against the patient's skin, there is no possibility of stopping the delivery of the drug. This prevents that the device is used plural times.

The device is easy and intuitively to use as it has no separate trigger element, e.g. a button or the like. The triggering is just caused by pressing the device with its safety shield 1104 against the patient's skin.

In summary, the device provides an easy to assemble structure with the possibility of using different kinds of syringes. The device can be easily and intuitively used in a failsafe manner.

The device provides several feedback signals to the user.

The invention claimed is:

1. An automatic drug delivery device for dispensing a fluid product, the automatic drug delivery device comprising:
   (a) a longitudinal housing extending along a longitudinal axis and having a proximal end close to a dispensing site, a distal end opposite to the proximal end and a hollow interior;
   (b) a removable cap mountable to the proximal end of the housing;
   (c) a syringe assembly arranged in a mounting position inside the housing and having a hollow syringe body and an injection needle formed with the hollow syringe body including the fluid product;
   (d) a drive mechanism configured to be triggered by a trigger element in order to initiate dispensing of the fluid product;
   wherein the drive mechanism is operatively coupled with a safety shield movable within the longitudinal housing,
   wherein the safety shield is biased by a safety shield spring into a proximal position in which the safety shield protrudes out of the proximal end of the longitudinal housing in order to cover a needle tip of the injection needle, and wherein the safety shield is movable into a distal position in which the injection needle is exposed for injection;
   the automatic drug delivery device further including a feedback mechanism configured to provide a visual feedback to a user indicating an actual state of operation, wherein the feedback mechanism includes a visual indicator configured to appear in a transparent window on the distal end of the housing,
   wherein the visual indicator comprises a shield retention indicator member releasably held in a non-visible position in which an indication surface is not visible through the transparent window of the housing, wherein the shield retention indicator member is biased in a distal direction by the safety shield spring such that the shield retention indicator member is configured to move, when released, into a visible position in which the indication surface is visible through the transparent window of the housing.

2. The automatic drug delivery device as claimed in claim 1, wherein the visual indicator is configured to appear in the transparent window on the distal end of the housing to indicate an end of injection.

3. The automatic drug delivery device as claimed in claim 1, wherein the visual indicator is configured to move distally to appear in the transparent window.

4. The automatic drug delivery device as claimed in claim 1, wherein a lock ring is provided within the longitudinal housing in an initial position, wherein the lock ring is configured to be locked to the safety shield during operation and wherein the lock ring is configured to block movement of the safety shield in a distal direction, when the safety shield covers the injection needle after the fluid product is finally dispensed and the automatic drug delivery device has been removed from an injection site.

5. The automatic drug delivery device as claimed in claim 1,
   wherein the safety shield has at least one longitudinal arm extending in a distal direction guided within the longitudinal housing, wherein the safety shield is configured to interact with the safety shield spring biasing the safety shield in a proximal direction via the at least one longitudinal arm and wherein the safety shield spring is supported between a shield retention trigger member and the shield retention indicator member, wherein the shield retention trigger member supports a proximal end of the safety shield spring and is configured to apply a biasing force to a distal end of the at least one longitudinal arm of the safety shield, and wherein the shield retention indicator member supports a distal end of the safety shield spring.

6. The automatic drug delivery device as claimed in claim 5, wherein the safety shield is configured to move the shield retention trigger member in the distal direction when the safety shield is being pushed in the distal direction for the purpose of initiating dispensing the fluid product, such that the shield retention trigger member compresses the safety shield spring, wherein after a predetermined stroke of the safety shield, the shield retention trigger member is configured to cause a release of the plunger from a retainer to move under the biasing force of the drive spring in the proximal direction in order to dispense the fluid product from the syringe body through the injection needle.

7. The automatic drug delivery device as claimed in claim 6, wherein the shield retention indicator includes at least one longitudinal holding arm, wherein the shield retention indicator is held by the at least one longitudinal holding arm in a non-visible position by the retainer, in which an indication surface is not visible through the housing, wherein the at least one longitudinal holding arm is held as long as the plunger has not reached a predetermined dispensing position, wherein the plunger is configured to cause the release of the at least one longitudinal holding arm from the retainer when reaching a predetermined dispensing position, and wherein after release of the at least one longitudinal holding arm the shield retention indicator is configured to be pushed by the safety shield spring to a visible position, in which the indication surface is visible through the housing.

8. The automatic drug delivery device as claimed in claim 7, wherein the shield retention indicator is configured to prevent distal movement of the shield retention trigger member and the shield retention trigger member is configured to prevent distal movement of the safety shield when the shield indicator member is released and has moved to the visible position and the safety shield has been biased to a position in which the safety shield covers the needle tip.

9. The automatic drug delivery device as claimed in claim 6, wherein proximal movement of the safety shield is prevented after release of the plunger from the retainer until the plunger reaches a predetermined dispensing position.

10. An automatic drug delivery device for dispensing a fluid product, the automatic drug delivery device comprising:
(a) a longitudinal housing extending along a longitudinal axis and having a proximal end close to a dispensing site, a distal end opposite to the proximal end and a hollow interior;
(b) a removable cap mountable to the proximal end of the housing;
(c) a syringe assembly arranged in a mounting position inside the housing and having a hollow syringe body and an injection needle formed with the hollow syringe body including the fluid product;
(d) a drive mechanism configured to be triggered by a trigger element in order to initiate dispensing of the fluid product;
wherein the drive mechanism is operatively coupled with a safety shield movable within the longitudinal housing,
wherein the safety shield is biased into a proximal position in which the safety shield protrudes out of the proximal end of the longitudinal housing in order to cover a needle tip of the injection needle, and wherein the safety shield is movable into a distal position in which the injection needle is exposed for injection;
the automatic drug delivery device further including a feedback mechanism configured to provide a visual feedback to a user indicating an actual state of operation, wherein the feedback mechanism includes a visual indicator configured to appear in a transparent window on the distal end of the housing,
wherein the visual indicator is formed by a radial inner indicator component and a radial outer indicator component biased by an indicator spring into an indicator position, wherein the indicator is configured to be released into the indicator position shortly before a predetermined dose of the drug is finished being delivered to a patient.

11. The automatic drug delivery device as claimed in claim 10, wherein the radial outer indicator component includes a visible surface and wherein the radial inner indicator component is configured to interact with the housing or an additional housing part for providing an audible and/or tactile signal.

12. An automatic drug delivery device for dispensing a fluid product, the automatic drug delivery device comprising:
(a) a longitudinal housing extending along a longitudinal axis and having a proximal end close to a dispensing site, a distal end opposite to the proximal end and a hollow interior;
(b) a removable cap mountable to the proximal end of the housing;
(c) a syringe assembly arranged in a mounting position inside the housing and having a hollow syringe body and an injection needle formed with the hollow syringe body including the fluid product;
(d) a drive mechanism configured to be triggered by a trigger element in order to initiate dispensing of the fluid product;
wherein the drive mechanism is operatively coupled with a safety shield movable within the longitudinal housing,
wherein the safety shield is biased into a proximal position in which the safety shield protrudes out of the proximal end of the longitudinal housing in order to cover a needle tip of the injection needle, and wherein the safety shield is movable into a distal position in which the injection needle is exposed for injection;
the automatic drug delivery device further including a feedback mechanism configured to provide a visual feedback to a user indicating an actual state of operation, wherein the feedback mechanism includes a visual indicator configured to appear in a transparent window on the distal end of the housing,
wherein the window is transparent around an entire circumference of the automatic drug delivery device such that the visual indicator is configured to appear in an angular range of up to 360°.

13. The automatic drug delivery device as claimed in claim 12, further comprising a distal endcap closed by a distal surface, wherein the distal endcap is formed from a transparent material to define the transparent window.

14. The automatic drug delivery device as claimed in claim 13, wherein the distal surface is formed from a transparent material.

15. An automatic drug delivery device for dispensing a fluid product, the automatic drug delivery device comprising:
(a) a longitudinal housing extending along a longitudinal axis and having a proximal end close to a dispensing site, a distal end opposite to the proximal end and a hollow interior;
(b) a removable cap mountable to the proximal end of the housing;
(c) a syringe assembly arranged in a mounting position inside the housing and having a hollow syringe body and an injection needle formed with the hollow syringe body including the fluid product;
(d) a drive mechanism configured to be triggered by a trigger element in order to initiate dispensing of the fluid product;
wherein the drive mechanism is operatively coupled with a safety shield movable within the longitudinal housing,
wherein the safety shield is biased into a proximal position in which the safety shield protrudes out of the proximal end of the longitudinal housing in order to cover a needle tip of the injection needle, and wherein the safety shield is movable into a distal position in which the injection needle is exposed for injection;

the automatic drug delivery device further including a feedback mechanism configured to provide a visual feedback to a user indicating an actual state of operation, wherein the feedback mechanism includes a visual indicator configured to appear in a transparent window on the distal end of the housing, wherein a lock ring is provided within the longitudinal housing in an initial position, wherein the lock ring is configured to be locked to the safety shield during operation and wherein the lock ring is configured to block movement of the safety shield in a distal direction, when the safety shield covers the injection needle after the fluid product is finally dispensed and the automatic drug delivery device has been removed from an injection site, wherein the lock ring in the initial state is held by a receiving component holding the syringe holder, wherein the lock ring is configured to engage with the safety shield, after the safety shield has been pushed in the distal direction, wherein the lock ring is configured to be moved with the safety shield in a proximal direction when removing the automatic drug delivery device from the injection site, and wherein the lock ring is configured to block any movement of the safety shield against the receiving component in the distal direction when covering the injection needle after use.

16. An automatic drug delivery device for dispensing a fluid product, the automatic drug delivery device comprising:
(a) a longitudinal housing extending along a longitudinal axis and having a proximal end close to a dispensing site, a distal end opposite to the proximal end and a hollow interior;
(b) a removable cap mountable to the proximal end of the housing;
(c) a syringe assembly arranged in a mounting position inside the housing and having a hollow syringe body and an injection needle formed with the hollow syringe body including the fluid product;
(d) a drive mechanism configured to be triggered by a trigger element in order to initiate dispensing of the fluid product;
wherein the drive mechanism is operatively coupled with a safety shield movable within the longitudinal housing,
wherein the safety shield is biased into a proximal position in which the safety shield protrudes out of the proximal end of the longitudinal housing in order to cover a needle tip of the injection needle, and wherein the safety shield is movable into a distal position in which the injection needle is exposed for injection;
the automatic drug delivery device further including a feedback mechanism configured to provide a visual feedback to a user indicating an actual state of operation, wherein the feedback mechanism includes a visual indicator configured to appear in a transparent window on the distal end of the housing,
wherein the safety shield has at least one longitudinal arm extending in a distal direction guided within the longitudinal housing, wherein the safety shield is configured to interact with a safety shield spring biasing the safety shield in a proximal direction via the at least one longitudinal arm and wherein the safety shield spring is supported between a shield retention trigger member and a shield retention indicator member, wherein the shield retention trigger member supports a proximal end of the safety shield spring and is configured to apply a biasing force to a distal end of the at least one longitudinal arm of the safety shield, and wherein the shield retention indicator member supports a distal end of the safety shield spring.

17. The automatic drug delivery device as claimed in claim 16, wherein the safety shield is configured to move the shield retention trigger member in the distal direction when the safety shield is being pushed in the distal direction for the purpose of initiating dispensing the fluid product, such that the shield retention trigger member compresses the safety shield spring, wherein after a predetermined stroke of the safety shield, the shield retention trigger member is configured to cause a release of the plunger from a retainer to move under the biasing force of the drive spring in the proximal direction in order to dispense the fluid product from the syringe body through the injection needle.

18. The automatic drug delivery device as claimed in claim 17, wherein the shield retention indicator includes at least one longitudinal holding arm, wherein the shield retention indicator is held by the at least one longitudinal holding arm in a non-visible position by the retainer, in which an indication surface is not visible through the housing, wherein the at least one longitudinal holding arm is held as long as the plunger has not reached a predetermined dispensing position, wherein the plunger is configured to cause the release of the at least one longitudinal holding arm from the retainer when reaching a predetermined dispensing position, and wherein after release of the at least one longitudinal holding arm the shield retention indicator is configured to be pushed by the safety shield spring to a visible position, in which the indication surface is visible through the housing.

19. The automatic drug delivery device as claimed in claim 18, wherein the shield retention indicator is configured to prevent distal movement of the shield retention trigger member and the shield retention trigger member is configured to prevent distal movement of the safety shield when the shield indicator member is released and has moved to the visible position and the safety shield has been biased to a position in which the safety shield covers the needle tip.

20. The automatic drug delivery device as claimed in claim 17, wherein proximal movement of the safety shield is prevented after release of the plunger from the retainer until the plunger reaches a predetermined dispensing position.

* * * * *

UNITED STATES PATENT AND TRADEMARK OFFICE
CERTIFICATE OF CORRECTION

Page 1 of 1

PATENT NO. : 12,161,843 B2
APPLICATION NO. : 17/057558
DATED : December 10, 2024
INVENTOR(S) : Appy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 942 days.

Signed and Sealed this
Eighth Day of July, 2025

Coke Morgan Stewart
*Acting Director of the United States Patent and Trademark Office*